(12) United States Patent
Medoff et al.

(10) Patent No.: US 10,501,761 B2
(45) Date of Patent: *Dec. 10, 2019

(54) PROCESSING BIOMASS TO OBTAIN HYDROXYLCARBOXYLIC ACIDS

(71) Applicant: Xyleco, Inc., Wakefield, MA (US)

(72) Inventors: Marshall Medoff, Brookline, MA (US); Thomas Craig Masterman, Rockport, MA (US); Andrew Papoulis, Canton, MA (US); Jaewoong Moon, Andover, MA (US); Jihan Khan, Cambridge, MA (US); Robert Paradis, Burlington, MA (US)

(73) Assignee: Xyleco, Inc., Wakefield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/786,388

(22) PCT Filed: Apr. 25, 2014

(86) PCT No.: PCT/US2014/035467
§ 371 (c)(1),
(2) Date: Oct. 22, 2015

(87) PCT Pub. No.: WO2014/176508
PCT Pub. Date: Oct. 30, 2014

(65) Prior Publication Data
US 2016/0076062 A1    Mar. 17, 2016

Related U.S. Application Data

(60) Provisional application No. 61/816,664, filed on Apr. 26, 2013.

(51) Int. Cl.
C12P 7/56 (2006.01)
C12P 7/42 (2006.01)
(Continued)

(52) U.S. Cl.
CPC ............. *C12P 7/56* (2013.01); *B01J 19/24* (2013.01); *C07C 67/28* (2013.01); *C08G 63/06* (2013.01); *C08G 63/08* (2013.01); *C08G 63/78* (2013.01); *C08K 3/04* (2013.01); *C08K 3/34* (2013.01); *C08K 3/346* (2013.01); *C08K 3/36* (2013.01); *C08K 3/38* (2013.01); *C08K 5/06* (2013.01); *C08K 5/11* (2013.01); *C08L 1/02* (2013.01); *C08L 3/00* (2013.01); *C08L 67/04* (2013.01); *C08L 97/02* (2013.01); *C12P 7/42* (2013.01); *C12P 7/46* (2013.01); *C12P 7/48* (2013.01); *C12P 7/625* (2013.01); *B01J 2219/24* (2013.01);
(Continued)

(58) Field of Classification Search
CPC .... B22D 18/06; C08K 3/04; C08K 2003/387; C08K 3/34; C08K 3/346; C08K 3/36; C08K 3/38; C08K 5/06; C08K 5/11; C08K 5/0016; C08K 5/0041; C08K 5/005; C08L 67/04; C08L 1/02; C08L 3/00; C08L 97/02; C08L 2312/00; B01J 19/24; B01J 2219/24; B01J 19/247; C07C 67/28; C07C 309/04; C07C 309/30; C07C 309/44; C07C 53/02; C07C 53/08; C07C 53/18; C07C 59/255; C08G 63/06; C08G 63/08; C08G 63/78; C08G 63/785; C12P 2201/00; C12P 7/42; C12P 7/46; C12P 7/48; C12P 7/56; C12P 7/625; A61K 2800/10; A61K 2800/56; A61K 2800/591; A61K 31/415; A61K 31/416; A61K 31/4178; A61K 31/4184; A61K 31/4439; A61K 31/496; A61K 31/5377; A61K 8/85; A61K 8/97; A61K 8/99; A61Q 13/00; A61Q 19/00; C07D 231/38; C07D 401/12; C07D 403/12; C08H 8/00; C08J 2367/04; C08J 3/24; C10G 2300/1014; C10G 2300/1018; Y02P 30/20
See application file for complete search history.

(56) References Cited

U.S. PATENT DOCUMENTS 3,844,890 A   10/1974   Horikoshi et al.
4,435,307 A    3/1984   Barbesgaard et al.
(Continued)

FOREIGN PATENT DOCUMENTS

CN      1299393 A    6/2001
CN    101402723 A    4/2009
(Continued)

OTHER PUBLICATIONS

Buyondo et al. (2011) Journal of Science and Technology for Forest Products and Processes 1(3): 38-47.*
(Continued)

*Primary Examiner* — Lisa J Hobbs
(74) *Attorney, Agent, or Firm* — Wolf, Greenfield & Sacks, P.C.

(57) ABSTRACT

Biomass (e.g., plant biomass, animal biomass, and municipal waste biomass) is processed to produce useful intermediates and products, such as hydroxy-carboxylic acids and hydroxy-carboxylic acid derivatives. A method includes treating a reduced recalcitrance lignocellulosic or cellulosic material with one or more enzymes and/or organisms (such as *lactobacillus, Pediococcus, Rhizopus, Enterococcus*) to produce an alpha, beta, gamma and/or delta hydroxycarboxylic acid (such as lactic acid, glycolic acid); and converting the alpha, beta, gamma and/or delta hydroxy-carboxylic acid to the product (such as esters, polymers, and copolymers).

42 Claims, 10 Drawing Sheets

US 10,501,761 B2

Page 2

(51) Int. Cl.

| | | |
|---|---|---|
| C12P 7/46 | (2006.01) | |
| C12P 7/48 | (2006.01) | |
| C08G 63/06 | (2006.01) | |
| C08G 63/08 | (2006.01) | |
| C08G 63/78 | (2006.01) | |
| B01J 19/24 | (2006.01) | |
| C07C 67/28 | (2006.01) | |
| C08K 3/04 | (2006.01) | |
| C08K 3/34 | (2006.01) | |
| C08K 3/36 | (2006.01) | |
| C08K 3/38 | (2006.01) | |
| C08K 5/06 | (2006.01) | |
| C08K 5/11 | (2006.01) | |
| C08L 1/02 | (2006.01) | |
| C08L 3/00 | (2006.01) | |
| C08L 67/04 | (2006.01) | |
| C08L 97/02 | (2006.01) | |
| C12P 7/62 | (2006.01) | |

(52) U.S. Cl.
CPC .... C08K 2003/387 (2013.01); C12P 2201/00 (2013.01)

(56) References Cited

U.S. PATENT DOCUMENTS

| 5,258,297 | A | 11/1993 | Akiba et al. |
| 5,574,129 | A | 11/1996 | Miyoshi et al. |
| 5,594,095 | A | 1/1997 | Gruber et al. |
| 6,262,226 | B1 | 7/2001 | Moore et al. |
| 6,353,086 | B1 | 3/2002 | Kolstad et al. |
| 6,534,679 | B2* | 3/2003 | Eyal ................ C07C 51/48 |
| | | | 435/139 |
| 7,652,167 | B2 | 1/2010 | Miller et al. |
| 7,900,857 | B2 | 3/2011 | Medoff |
| 7,931,784 | B2 | 4/2011 | Medoff |
| 7,932,065 | B2 | 4/2011 | Medoff |
| 7,971,809 | B2 | 7/2011 | Medoff |
| 8,074,910 | B2 | 12/2011 | Medoff |
| 8,083,906 | B2 | 12/2011 | Medoff |
| 8,142,620 | B2 | 3/2012 | Medoff |
| 8,318,453 | B2 | 11/2012 | Medoff |
| 8,377,668 | B2 | 2/2013 | Medoff et al. |
| 8,415,122 | B2 | 4/2013 | Medoff et al. |
| 8,465,956 | B2 | 6/2013 | Medoff et al. |
| 8,492,128 | B2 | 7/2013 | Medoff |
| 8,691,526 | B2 | 4/2014 | Medoff et al. |
| 8,911,833 | B2 | 12/2014 | Medoff |
| 9,453,250 | B2 | 9/2016 | Medoff et al. |
| 9,631,208 | B2 | 4/2017 | Medoff et al. |
| 10,174,160 | B2 | 1/2019 | Medoff et al. |
| 2004/0024111 | A1 | 2/2004 | Husemann et al. |
| 2004/0157967 | A1 | 8/2004 | Ito |
| 2008/0206541 | A1 | 8/2008 | Medoff |
| 2009/0325854 | A1 | 12/2009 | Funk et al. |
| 2010/0064746 | A1 | 3/2010 | Medoff |
| 2010/0089289 | A1 | 4/2010 | Mahiat et al. |
| 2010/0105119 | A1 | 4/2010 | Medoff |
| 2010/0112242 | A1 | 5/2010 | Medoff |
| 2010/0124539 | A1 | 5/2010 | Hanson |
| 2010/0124583 | A1 | 5/2010 | Medoff |
| 2010/0159569 | A1 | 6/2010 | Medoff et al. |
| 2010/0203495 | A1 | 8/2010 | Medoff et al. |
| 2010/0203607 | A1 | 8/2010 | Medoff et al. |
| 2010/0249362 | A1 | 9/2010 | Kamikawa et al. |
| 2011/0262985 | A1 | 10/2011 | Medoff |
| 2012/0045793 | A1 | 2/2012 | Shock et al. |
| 2012/0052536 | A1 | 3/2012 | Medoff et al. |
| 2012/0091035 | A1 | 4/2012 | Medoff et al. |
| 2012/0100577 | A1* | 4/2012 | Medoff ................ C12P 7/10 |
| | | | 435/72 |
| 2012/0100586 | A1 | 4/2012 | Medoff et al. |
| 2012/0308991 | A1 | 12/2012 | Eiteman et al. |
| 2012/0315675 | A1* | 12/2012 | Medoff ................ C08H 8/00 |
| | | | 435/99 |
| 2013/0017586 | A1* | 1/2013 | Ropars ................ C12P 7/10 |
| | | | 435/150 |
| 2013/0052682 | A1 | 2/2013 | Medoff et al. |
| 2013/0052687 | A1 | 2/2013 | Medoff et al. |
| 2014/0004570 | A1 | 1/2014 | Medoff et al. |
| 2014/0004573 | A1 | 1/2014 | Medoff et al. |
| 2014/0284277 | A1 | 9/2014 | Medoff et al. |
| 2014/0284494 | A1 | 9/2014 | Medoff et al. |
| 2014/0284501 | A1 | 9/2014 | Medoff et al. |
| 2014/0286714 | A1 | 9/2014 | Medoff et al. |
| 2014/0287469 | A1 | 9/2014 | Medoff et al. |
| 2014/0287470 | A1 | 9/2014 | Medoff et al. |
| 2014/0318969 | A1 | 10/2014 | Medoff et al. |
| 2015/0166786 | A1* | 6/2015 | Harvey ................ A61K 47/42 |
| | | | 514/772.1 |
| 2015/0279618 | A1 | 10/2015 | Peters et al. |
| 2015/0284907 | A1 | 10/2015 | Medoff et al. |
| 2015/0361457 | A1 | 12/2015 | Medoff et al. |
| 2015/0368684 | A1 | 12/2015 | Medoff et al. |
| 2016/0053047 | A1 | 2/2016 | Medoff et al. |
| 2016/0060386 | A1 | 3/2016 | Medoff et al. |
| 2016/0083754 | A1 | 3/2016 | Medoff et al. |

FOREIGN PATENT DOCUMENTS

| EP | 2218714 | 8/2010 |
| JP | H06-306149 A | 11/1994 |
| JP | 2000-297143 A | 10/2000 |
| JP | 2006-333847 A | 12/2006 |
| JP | 2009-035706 A | 2/2009 |
| JP | 2010-126643 A | 6/2010 |
| WO | WO 93/17993 A1 | 9/1993 |
| WO | WO-99/50345 | 10/1999 |
| WO | WO-2006/053936 | 5/2006 |
| WO | WO-2010/085380 | 7/2010 |
| WO | WO 2011/149774 A1 | 12/2011 |
| WO | WO-2013/010087 A1 | 1/2013 |
| WO | WO-2013/096698 | 6/2013 |

OTHER PUBLICATIONS

Cui et al. (2011) Bioresource Technology 102(2): 1831-1836 (Year: 2011).*
Ali et al., "Production of Lactic Acid from Corn Cobs Hydrolysate through Fermentation by Lactobaccillus Delbrukii", African Journal of Biotechnology, 8(17):4175-4178, Sep. 1, 2009 (4 pages).
Buyondo et al., "Lactic Acid Production by Lactobacillus Pentosus from Wood Extract Hydrolysates", Journal of Science & Technology for Forest Products and Processes, 1(3):38-47, 2011 (10 pages).
European Supplementary Search Report issued in European Patent Application No. 14788244.3, dated Apr. 19, 2016 (10 pages).
European Supplementary Search Report issued in European Patent Application No. 14788290.6, dated Mar. 4, 2016 (8 pages).
Fleury et al., "Comparison of Devolatilization Technologies for Viscous Polymers," Conference Proceedings, ANTEC, May 1-5, 2005 (6 pages).
European Supplementary Search Report issued in European Patent Application No. 14 78 8290, completed Jun. 15, 2016 (4 pages).
International Search Report and Written Opinion issued in PCT/US2014/035467, dated Dec. 2, 2014 (13 pages).
Latinen, "Devolatilization of Viscous Polymer Systems," Advances in Chemistry Series, American Chemical Society, Jan. 1962, pp. 235-246 (12 pages).
Romani, et al., "SSF Production of Lactic Acid from Cellulosic Biosludges", Bioresource Technology, 99:4247-4254, 2008 (8 pages).
Widmer, "Behavior of Viscous Polymers during Solvent Stripping or Reaction in an Agitated Thin Film," Advances in Chemistry; American Chemical Society, Jun. 1973, pp. 51-67 (17 pages).
English language translation of Japanese Patent Application No. JP-07-002983, published Jan. 6, 1995 (12 pages).
Avérous, "Polylactic acid: synthesis, properties and applications," Monomers, Polymers and Composites from Renewable Resources, pp. 433-450 (2008).

(56) References Cited

OTHER PUBLICATIONS

Hou and Shaw, eds. "Gram-Positive Bacteria as Biocatalysts to Convert Biomass Derived Sugars into Biofuel and Chemicals," Biocatalysis and Bioenergy, pp. 249-264 (2008).
International Search Report and Written Opinion for PCT/US2014/035469 dated Sep. 2, 2014.
Thomas, Production of Lactic Acid from Pulp Mill Solid Waste and Xylose Using Lactobacillus delbrueckii (NRRL B445). Applied Biochemistry and Biotechnology. 2000;84-86:455-68.
Yarullina et al., Bacteria of the genus *Lactobacillus*: General Characteristics and Working With Them. Tutorial Kasan. 2014. 51 pages.

\* cited by examiner alpha-hydroxy carboxylic acid
(2-hydroxy acetic acid)

D-lactic acid beta-hydroxy carboylic acid
( 3-hydroxy propionic acid)

L-lactic acid gamma-hydroxy carboxylic acid
(3 hydroxyl butyric acid)

tartaric acid (alpha and beta; no
stereochemistry indicated)

delta-hydroxy carboxylic acid
(4 hydroxy valeric acid)

gluconic acid
(alpha, beta, gamma and delta)

PROCESSING BIOMASS TO OBTAIN HYDROXYLCARBOXYLIC ACIDS

CROSS REFERENCE TO RELATED APPLICATIONS

This application is a National Stage Entry of PCT International Application No. PCT/US2014/035467 filed on Apr. 25, 2014, which claims priority to U.S. Provisional Application No. 61/816,664 filed Apr. 26, 2013, the contents of which are hereby incorporated by reference in their entirety.

BACKGROUND OF THE INVENTION

Many potential lignocellulosic feedstocks are available today, including agricultural residues, woody biomass, municipal waste, oilseeds/cakes and seaweed, to name a few. At present, these materials are often under-utilized, being used, for example, as animal feed, biocompost materials, burned in a co-generation facility or even landfilled.

Lignocellulosic biomass includes crystalline cellulose fibrils embedded in a hemicellulose matrix, surrounded by lignin. This produces a compact matrix that is difficult to access by enzymes and other chemical, biochemical and/or biological processes. Cellulosic biomass materials (e.g., biomass material from which the lignin has been removed) is more accessible to enzymes and other conversion processes, but even so, naturally-occurring cellulosic materials often have low yields (relative to theoretical yields) when contacted with hydrolyzing enzymes. Lignocellulosic biomass is even more recalcitrant to enzyme attack. Furthermore, each type of lignocellulosic biomass has its own specific composition of cellulose, hemicellulose and lignin.

SUMMARY

Generally, this invention relates to methods and processes for converting a material, such as a biomass feedstock, e.g., cellulosic, starchy or lignocellulosic materials, to useful products, for example, hydroxy-carboxylic acids (e.g., alpha, beta, gamma and delta hydroxy-carboxylic acids) and derivatives of hydroxy-carboxylic acids (e.g., esters). Such hydroxy-carboxylic acids can be poly-hydroxy-carboxylic acids, e.g. di-, tri-, tetra-, penta-, hexa-hepta- and octa-hydroxy carboxylic acids. The poly-hydroxy-carboxylic acid can be substituted with other groups, e. g. alkyl groups. The carbon chain of the carboxylic acid can be straight chained, branched, cyclic, or alicyclic.

In one aspect the invention relates to a method for making a product including treating a reduced recalcitrance biomass (e.g., lignocellulosic or cellulosic material) with one or more enzymes and/or organisms to produce a hydroxy-carboxylic acid (e.g., an alpha, beta, gamma or delta hydroxy-carboxylic acid) and converting the hydroxy-carboxylic acid to the product. Optionally, the feedstock is pretreated with at least one method selected from irradiation (e.g., with an electron beam), sonication, oxidation, pyrolysis and steam explosion, for example, to reduce the recalcitrance of the lignocellulosic or cellulosic material. Some examples of hydroxy-carboxylic acids that can be produced and then further converted include glycolic acid, lactic acid, malic acid, citric acid, and tartaric acid(di substituted), 3-hydroxybutyric acid (beta substituted), 4-hydroxybutyric acid (gamma substituted), 3 hydroxyvaleric acid (beta substituted), gluconic acid (tetra substituted at alpha, beta, gamma, and delta carbons with an additional hydroxy at the epsilon carbon).

In some implementation of the method, the hydroxycarboxylic acid is converted chemically, for example, by converting lactic acid to esters by treating with an alcohol and an acid catalyst. Other methods of chemically converting that can be utilized include polymerization, isomerization, esterification, oxidation, reduction, disproportionation and combinations of these.

In some other implementation, the lignocellulosic or cellulosic material is treated with one of more enzymes to release one or more sugars; for example, to release glucose, xylose, sucrose, maltose, lactose, mannose, galactose, arabinose, fructose, dimers of these such as cellobiose, heterodimers of these such as sucrose, oligomers of these, and mixtures of these. Optionally, treating can further include (e.g., subsequently to releasing sugars) utilizing (e.g., by contacting with the sugars and/or biomass) one or more organisms to produce the hydroxy-carboxylic acid. For example, the sugars can be fermented by a sugar fermenting organism to the hydroxyl acid. Sugars that are released from the biomass can be purified (e.g., prior to fermenting) by, for example, a method selected from electrodialysis, distillation, centrifugation, filtration, cation exchange chromatography and combinations of these in any order.

In some implementation, converting comprises polymerizing the lactic acid to a polymer (e.g., polymerizing in a melt such as without an added solvent). For example, polymerizing methods can be selected from direct condensation of the lactic acid, azeotropic dehydrative condensation of the lactic acid, and dimerizing the lactic acid to lactide followed by ring opening polymerization of the lactide. The polymerization can be in a melt (e.g., without a solvent and above the melting point of the polymer) or can be in a solution (e.g., with an added solvent).

Optionally, when the polymerization method is direct condensation, the polymerization can include utilizing coupling agents and/or chain extenders to increase the molecular weight of the polymer. For example, the coupling agents and/or chain extenders can include triphosgene, carbonyl diimidazole, dicyclohexylcarbodiimide, diisocyanate, acid chlorides, acid anhydrides, epoxides, thiirane, oxazoline, orthoester, and mixtures of these. Alternatively, the polymer can have a co monomer which is a polycarboxylic acid or polyols or a combination of these.

Optionally, polymerizations can be done utilizing catalysts and/or promoters. For example, Lewis and Bronsted (protonic) acids can be used. Examples of the acids include $H_3PO_4$, $H_2SO_4$, methane sulfonic acid, p-toluene sulfonic acid, NAFION® NR 50 H+ form From DuPont, Wilmington Del., Acids supported on polymers, metals, Mg, Al, Ti, Zn, Sn, metal oxides, $TiO_2$, ZnO, $GeO_2$, $ZrO_2$, SnO, $SnO_2$, $Sb_2O_3$, metal halides, $ZnCl_2$, $SnCl_2$, $SnCl_4$, $Mn(AcO)_2$, $Fe_2(LA)_3$, $Co(AcO)_2$, $Ni(AcO)_2$, $Cu(OA)_2$, $Zn(LA)_2$, $Y(OA)_3$, $Al(i-PrO)_3$, $Ti(BuO)_4$, $TiO(acac)_2$, $(Bu)_2SnO$, tin octoate, solvates of any of these and mixtures of these can be used.

The polymerizations or at least a portion of the polymerizations can be done at a temperature between about 100 and about 200° C., such as between about 110 and about 170° C. or between about 120 and about 160° C. Optionally at least a portion of the polymerizations can be performed under vacuum (e.g., between about 0.1 mm Hg to 300 mm Hg).

In the implementations wherein the polymerization method includes dimerizing the lactic acid to lactide followed by ring opening polymerization of the lactide, the dimerization can include heating the lactic acid to between 100 and 200° C. under a vacuum of about 0.1 to about 100 mmHg. Optionally, the dimerization (e.g., dimerization reaction) can include utilizing a catalyst. Catalysts can, for example, include Sn octoate, Li carbonate, Zn diacetate dehydrate, Ti tetraisopropoxide, potassium carbonate, tin powder and mixtures of these. Optionally, a ring opening polymerization catalyst is utilized. For example, the ring opening polymerization catalyst can be chosen from protonic acids, HBr, HCl, triflic acid, Lewis acids, $ZnCl_2$, $AlCl_3$, anions, potassium benzoate, potassium phenoxide, potassium t-butoxide, and zinc stearate, metals, Tin, zinc, aluminum, antimony, bismuth, lanthanide and other heavy metals, Tin (II) oxide and tin (II) octoate (e.g., 2-ethylhexanoate), tetra phenyl tin, tin (II) and (IV) halogenides, tin (II) acetylacetonoate, distannoxanes (e.g., hexabutyldistannoxane, $R_3SnOSnR_3$ where R groups are alkyl or aryl groups), $Al(OiPr)_3$, other functionalized aluminum alkoxides (e.g., aluminum ethoxide, aluminum methoxide), ethyl zinc, lead (II) oxide, antimony octoate, bismuth octoate, rare earth catalysts, yttrium tris(methyl lactate), yttrium tris(2-N-N-dimethylamino ethoxide), samarium tris(2-N-N-dimethyl-amino ethoxide), yttrium tris(trimethylsilyl methyl), lanthanum tris(2,2,6,6-tetramethylheptanedionate), lanthanum tris (acetylacetonate), yttrium octoate, yttrium tris (acetylacetonate), yttrium tris(2,2,6,6-tetramethylheptanedionate), combinations of these (e.g., ethyl zinc/aluminum isopropoxide) and mixtures of these.

In the implementations wherein polymers are made from the lactic acid, the methods can further include blending the polymer with a second polymer. For example, a second polymer can include polyglycols, polyvinyl acetate, polyolefins, styrenic resins, polyacetals, poly(meth)acrylates, polycarbonate, polybutylene succinate, elastomers, polyurethanes, natural rubber, polybutadiene, neoprene, silicone, and combinations of these.

In other implementations wherein polymers are made from the lactic acid, a co-monomer can be co-polymerized with the lactic acid or lactide. For example, the co-monomer can include elastomeric units, lactones, glycolic acid, carbonates, morpholinediones, epoxides, 1,4-benzodioxepin-2,5-(3H)-dione glycosalicylide, 1,4-benzodioxepin-2,5-(3H, 3-methyl)-dione lactosalicylide, dibenzo-1,5 dioxacin-6-12-dione disalicylide, morpholine-2,5-dione, 1,4-dioxane-2,5-dione glycolide, oxepane-2-one ε-caprolactone, 1,3-dioxane-2-one trimethylene carbonate, 2,2-dimethyltrimethylene carbonate, 1,5-dioxepane-2-one, 1,4-dioxane-2-one p-dioxanone, gamma-butyrolactone, beta-butyrolactone, beta-methyl-delta-valerolactone, 1,4-dioxane-2,3-dione ethylene oxalate, 3-[benzyloxycarbonyl methyl]-1,4-dioxane-2,5-dione, ethylene oxide, propylene oxide, 5,5'(oxepane-2-one), 2,4,7,9-tetraoxa-spiro[5,5]undecane-3,8-dione, spiro-bis-di-methylene carbonate and mixtures of these.

In any implementation wherein polymers are made, the polymers can be combined with fillers (e.g., by extrusion and/or compression molding). For example, some fillers that can be used include silicates, layered silicates, polymer and organically modified layered silicate, synthetic mica, carbon, carbon fibers, glass fibers, boric acid, talc, montmorillonite, clay, starch, corn starch, wheat starch, cellulose fibers, paper, rayon, non-woven fibers, wood flours, whiskers of potassium titanate, whiskers of aluminum borate, 4,4'-thiodiphenol, glycerol and mixtures of these.

In any implementation wherein polymers are made, the method can further include branching and/or cross linking the polymer. For example, the polymers can be treated with a cross linking agent including 5,5'-bis(oxepane-2-one)(bis-ε-caprolactone)), spiro-bis-dimethylene carbonate, peroxides, dicumyl peroxide, benzoyl peroxide, unsaturated alcohols, hydroxyethyl methacrylate, 2-butene-1,4-diol, unsaturated anhydrides, maleic anhydride, saturated epoxides, glycidyl methacrylate, irradiation and combinations of these. Optionally, a molecule (e.g., a polymer) can be grafted to the polymer. For example, grafting can be done treating the polymer with irradiation, peroxide, crossing agents, oxidants, heating or any method that can generate a cation, anion or radical on the polymer.

In any implementation wherein polymers are processed, processing can include injection molding, blow molding and thermoforming.

In any implementation wherein polymers are processed, the polymers can be combined with a dye and/or a fragrance. For example, dyes that can be used include blue 3, blue 356, brown 1, orange 29, violet 26, violet 93, yellow 42, yellow 54, yellow 82 and combinations of these. Examples of fragrances include wood, evergreen, redwood, peppermint, cherry, strawberry, peach, lime, spearmint, cinnamon, anise, basil, bergamot, black pepper, camphor, chamomile, citronella, eucalyptus, pine, fir, geranium, ginger, grapefruit, jasmine, juniper berry, lavender, lemon, mandarin, marjoram, musk, myrrh, orange, patchouli, rose, rosemary, sage, sandalwood, tea tree, thyme, wintergreen, ylang ylang, vanilla, new car or mixtures of these fragrances. Fragrances can be used in any amount, for example, between about 0.005% by weight and about 20% by weight (e.g., between about 0.1% and about 5 wt. %, between about 0.25 wt. % and about 2.5%).

In any implementation wherein polymers are processed, the polymer can be blended with a plasticizer. For example, plasticizers include triacetin, tributyl citrate, polyethylene glycol, GRINDSTED® SOFT-N-SAFE (from Danisco, DuPont, Wilmington Del., diethyl bishydroxymethyl malonate) and mixtures of these.

In any of the implementations wherein polymers are made, the polymers can be processed or further processed by shaping, molding, carving, extruding and/or assembling the polymer into the product.

In another aspect, the invention relates to products made by the methods discussed above. For example, the products include a converted hydroxy-carboxylic acid wherein the hydroxy-carboxylic acid is produced by the fermentation of biomass derived sugars (e.g., glycolic acid, D-lactic acid and/or L-lactic acid, D-malic acid, L-malic, citric acid and D-tartaric acid, L-tartaric acid and meso-tartaric acid). The biomass includes cellulosic and lignocellulosic materials and these can release sugars by acidic or enzymatic saccharification. In addition, the biomass can be treated, e.g., by irradiation.

The products, for example, include polymers, including one or more hydroxyl acids in the polymer backbone and optionally non-hydroxy carboxylic acids in the polymer backbone. Optionally the polymers can be cross-linked or graft co-polymers. Optionally the polymer can be, blended with a second polymer, blended with a plasticizer, blended with an elastomer, blended with a fragrance, blended with a dye, blended with a pigment, blended with a filler or blended with a combination of these.

In yet another embodiment, the invention relates to a system for polymerization including a reaction vessel, a screw extruder and a condenser. The system also includes a recirculating fluid flow path from an outlet of the reaction vessel to an inlet of the screw extruder and from an outlet of the screw extruder to an inlet to the reaction vessel. In addition, the system includes a fluid flow path from a second outlet of the reaction vessel to an inlet of the condenser. Optionally, the system further includes a vacuum pump in fluid connection with the second fluid flow path for producing a vacuum in the second fluid flow path. Also optionally, the system can include a control valve that in a first position provides a non-disrupted flow in the recirculating fluid flow path and in a second position provides a second fluid flow path. In some implementations, the second fluid flow path is from the outlet of the reaction vessel to an inlet of a pelletizer. In other implementations, the second fluid flow path is from the outlet of the reaction vessel to the inlet of the extruder and from the outlet of the extruder to the inlet of a pelletizer.

Some of the products described herein, for example, lactic acid, can be produced by chemical methods. However, fermentative methods can be much more efficient, providing high biomass conversion, selective conversion and high production rates. In particular, fermentative methods can produce D or L isomers of hydroxy-carboxylic acids (e.g., lactic acid) at chiral purity of near 100% or mixtures of these isomers, whereas the chemical methods typically produce racemic mixtures of the D and L isomers. When a hydroxy-carboxylic acid is listed without its stereochemistry it is understood that D, L, meso, and/or mixtures are assumed.

The methods describe herein are also advantageous in that the starting materials (e.g., sugars) can be completely derived from biomass (e.g., cellulosic and lignocellulosic materials). In addition, some of the products described herein such as polymers of hydroxy-carboxylic acids (e.g., poly lactic acid) are compostable, biodegradable and/or recyclable. Therefore, the methods described herein can provide useful materials and products from renewable sources (e.g., biomass) wherein the products themselves can be re-utilized or simply safely returned to the environment.

For example, some products that can be made by the methods, systems or equipment described herein include personal care items, tissues, towels, diapers, green packaging, compostable pots, consumer electronics, laptop casings, mobile phone casings, appliances, food packaging, disposable packaging, food containers, drink bottles, garbage bags, waste compostable bags, mulch films, controlled release matrices, controlled release containers, containers for fertilizers, containers for pesticides, containers for herbicides, containers for nutrients, containers for pharmaceuticals, containers for flavoring agents, containers for foods, shopping bags, general purpose film, high heat film, heat seal layer, surface coating, disposable tableware, plates, cups, forks, knives, spoons, sporks, bowls, automotive parts, panels, fabrics, under hood covers, carpet fibers, clothing fibers, fibers for garments, fibers for sportswear, fibers for footwear, surgical sutures, implants, scaffolding and drug delivery systems.

Other features and advantages of the invention will be apparent from the following detailed description, and from the claims.

DESCRIPTION OF THE DRAWING

The foregoing will be apparent from the following more particular description of example embodiments of the invention, as illustrated in the accompanying. The drawings are not necessarily to scale, emphasis instead being placed upon illustrating embodiments of the present invention.

DETAILED DESCRIPTION

Using the equipment, methods and systems described herein, cellulosic and lignocellulosic feedstock materials, for example, that can be sourced from biomass (e.g., plant biomass, animal biomass, paper, and municipal waste biomass) and that are often readily available but difficult to process, can be turned into useful products such as sugars and hydroxy-carboxylic acids. Included are equipment, methods and systems to chemically convert the primary products produced from the biomass to secondary product such as polymers (e.g., poly lactic acid) and polymer derivatives (e.g., composites, elastomers and co-polymers).

Biomass is a complex feedstock. For example, lignocellulosic materials include different combinations of cellulose, hemicellulose and lignin. Cellulose is a linear polymer of glucose. Hemicellulose is any of several heteropolymers, such as xylan, glucuronoxylan, arabinoxylan and xyloglucan. The primary sugar monomer present (e.g., present in the largest concentration) in hemicellulose is xylose, although other monomers such as mannose, galactose, rhamnose, arabinose and glucose are present. Although all lignins show variation in their composition, they have been described as an amorphous dendritic network polymer of phenyl propene units. The amounts of cellulose, hemicellulose and lignin in a specific biomass material depend on the source of the biomass material. For example, wood-derived biomass can be about 38-49% cellulose, 7-26% hemicellulose and 23-34% lignin depending on the type. Grasses typically are 33-38% cellulose, 24-32% hemicellulose and 17-22% lignin. Clearly lignocellulosic biomass constitutes a large class of substrates.

Enzymes and biomass-destroying organisms that break down biomass, such as the cellulose, hemicellulose and/or the lignin portions of the biomass as described above, contain or manufacture various cellulolytic enzymes (cellulases), ligninases, xylanases, hemicellulases or various small molecule biomass-destroying metabolites. A cellulosic substrate is initially hydrolyzed by endoglucanases at random locations producing oligomeric intermediates. These intermediates are then substrates for exo-splitting glucanases such as cellobiohydrolase to produce cellobiose from the ends of the cellulose polymer. Cellobiose is a water-soluble 1,4-linked dimer of glucose. Finally, cellobiase cleaves cellobiose to yield glucose. In the case of hemicellulose, a xylanase (e.g., hemicellulase) acts on this biopolymer and releases xylose as one of the possible products.

Figure 1:
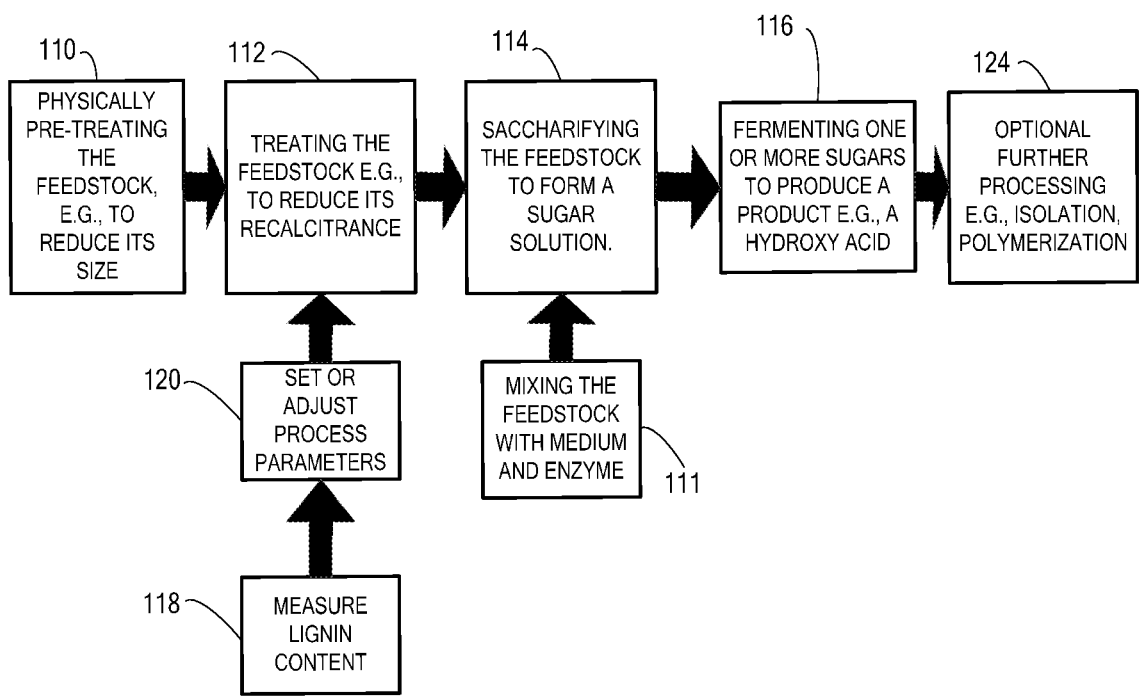
FIG. 1 is a flow diagram showing processes for manufacturing products from a biomass feedstock

FIG. 1 is a flow diagram showing processes for manufacturing is a flow diagram showing processes for manufacturing hydroxy-carboxylic acids from a feedstock (e.g., cellulosic or lignocellulosic materials). In an initial step (110) the method includes optionally mechanically treating a cellulosic and/or lignocellulosic feedstock, for example, to comminute/size reduce the feedstock. Before and/or after this treatment, the feedstock can be treated with another physical treatment (112), for example, irradiation, sonication, steam explosion, oxidation, pyrolysis or combinations of these, to reduce or further reduce its recalcitrance. A sugar solution e.g., including glucose and/or xylose, is formed by saccharifying the feedstock (114). The saccharification can be, for example, accomplished efficiently by the addition of one or more enzymes, e.g., cellulases and/or xylanases (111) and/or one or more acids. A product or several products can be derived from the sugar solution, for example, by fermentation to a hydroxy-carboxylic acid (116). Following fermentation, the fermentation product (e.g., or products, or a subset of the fermentation products) can be purified or they can be further processed, for example, polymerized and/or isolated (124). Optionally, the sugar solution is a mixture of sugars and the organism selectively ferments only one of the sugars. The fermentation of only one of the sugars in a mixture can be advantageous as described in International App. No. PCT/US2014/021813 filed Mar. 7, 2014, the entire disclosure of which is incorporated herein by reference. If desired, the steps of measuring lignin content (118) and setting or adjusting process parameters based on this measurement (120) can be performed at various stages of the process, for example, as described in U.S. Pat. No. 8,415,122, issued Apr. 9, 2013 the entire disclosure of which is incorporated herein by reference. Optionally, enzymes (e.g., in addition to cellulases and xylanases) can be added in step (114), for example, a glucose isomerase can be used to isomerize glucose to fructose. Some relevant uses of isomerase are discussed in PCT Application No. PCT/US12/71093, filed on Dec. 20, 2012, published as WO 2013/096700 the entire disclosure of which is incorporated herein by reference.

In some embodiments the liquids after saccharification and/or fermentation can be treated to remove solids, for example, by centrifugation, filtration, screening, or rotary vacuum filtration. For example, some methods and equipment that can be used during or after saccharification are disclosed in International App. No. PCT/US2013/048963 filed Jul. 1, 2013, and International App. No. PCT/US2014/021584, filed on Mar. 7, 2014, the entire disclosures of which are incorporated herein by reference. In addition other separation techniques can be used on the liquids, for example, to remove ions and de-colorize. For example, chromatography, simulated moving bed chromatograph and electrodialysis can be used to purify any of the solutions and/or suspensions described herein. Some of these methods are discussed in International App. No. PCT/US2014/021638, filed on Mar. 7, 2014, and International App. No. PCT/US2014/021815, filed on Mar. 7, 2014, the entire disclosures of which are incorporated herein by reference. Solids that are removed during the processing can be utilized for energy co-generation, for example, as discussed in International App. No. PCT/US2014/021634, filed on Mar. 7, 2014, the entire disclosure of which is herein incorporated by reference.

Optionally, the sugars released from biomass as described in FIG. 1, for example, glucose, xylose, sucrose, maltose, lactose, mannose, galactose, arabinose, homodimers and heterodimers of these (e.g., cellobiose, sucrose), trimers, oligomers and mixtures of these, can be fermented to hydroxy-carboxylic acids such as alpha, beta or gamma hydroxyl acids (e.g., lactic acid). In some embodiments, the saccharification and fermentation are done simultaneously, for example, using the thermophilic organism such as *Bacillus coagulans* MXL-9 as described by S. L. Walton in J. Ind. Microbiol. Biotechnol. (2012) pg. 823-830.

Figure 10:
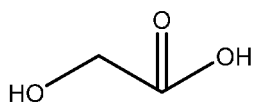
FIG. 10 shows the chemical structures of some exemplary hydroxyl acids.
Figure 10:
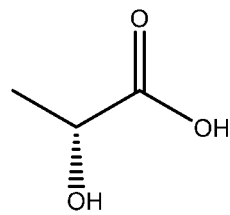
Figure 10:
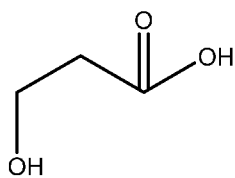
Figure 10:
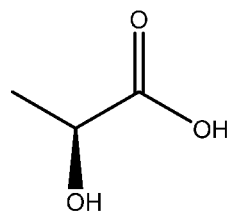
Figure 10:
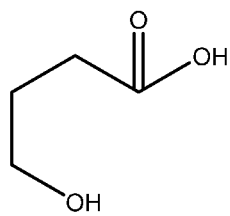
Figure 10:
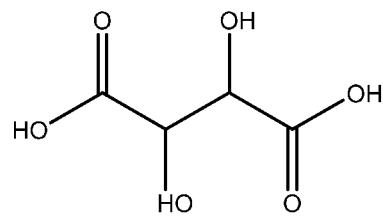
Figure 10:
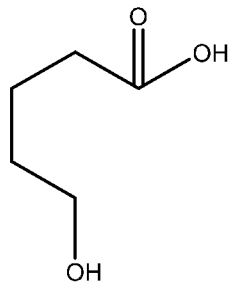
Figure 10:
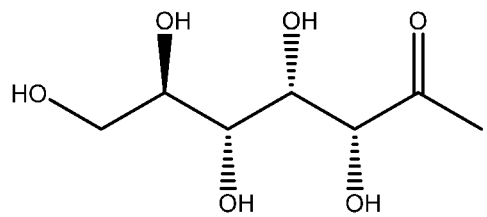

Hydroxy-carboxylic acids that can be produced by the methods systems and equipment described herein include, for example, of alpha, beta, gamma, and delta hydroxy-carboxylic acids. FIG. 10 shows the chemical structures of some hydroxyl acids. That is, if there is only one hydroxyl group it can be at any of the alpha, beta, gamma or delta carbon atoms in the carbon chain. The carbon chain may be a straight chain, branched or cyclic system. The hydroxy carboxylic acid may also include fatty acids of carbon chain lengths of 10 to 22 with the hydroxy substituent at the alpha, beta, gamma, or delta carbon.

The hydroxy-carboxylic acids include those with multiple hydroxy substituents, or in alternative description a poly hydroxy substituted carboxylic acid. Such hydroxy-carboxylic acids can be poly-hydroxy-carboxylic acid, e.g. di-, tri-, tetra-, penta-, hexa- hepta- and octa-hydroxy substituted carboxylic acid. The carbon chain of the carboxylic acid may be straight chained, branched, cyclic, or alicyclic. Examples of this are tartaric acid and its isomers, dihydroxy-3-methylpentanoic acid, 3,4-dihydroxymandelic acid, gluconic acid, glucuronic acid and the like.

For example, the hydroxy-carboxylic acids include glycolic acid, lactic acid (e.g., D, L or mixtures of D and L), malic acid, citric acid, tartaric acid, carmine, cyclobutyrol, 3-dehydroquinic acid, diethyl tartrate, 2,3-dihydroxy-3-methylpentanoic acid, 3,4-dihydroxymandelic acid, glyceric acid, homocitric acid, homoisocitric acid, beta-hydroxy beta-methylbutyric acid, 4-hydroxy-4-methylpentanoic acid, hydroxybutyric acid, 2-hydroxybutyric acid, beta-hydroxybutyric acid, gamma-hydroxybutyric acid, alpha-hydroxyglutaric acid, 5-hydroxyindoleacetic acid, 3-hydroxy-isobutyric acid, 3-hydroxypentanoic acid, 3-hydroxypropionic acid, hydroxypyruvic acid, gluconic acid, glucuronic acid, alpha, beta, gamma or delta-hydroxyvaleric acid; isocitric acid, isopropylmalic acid, kynurenic acid, mandelic acid, mevalonic acid, monatin, myriocin, pamoic acid, pantoic acid, prephenic acid, shikimic acid, tartronic acid, threonic acid, tropic acid, vanillylmandelic acid, xanthurenic acid and mixtures of these. For those hydroxy-carboxylic acids listed all of the stereo isomers are included in the list. For instance, tartaric acid includes, the D, L, and meso isomers and mixtures thereof.

Preparation of Lactic Acid

Figure 2:
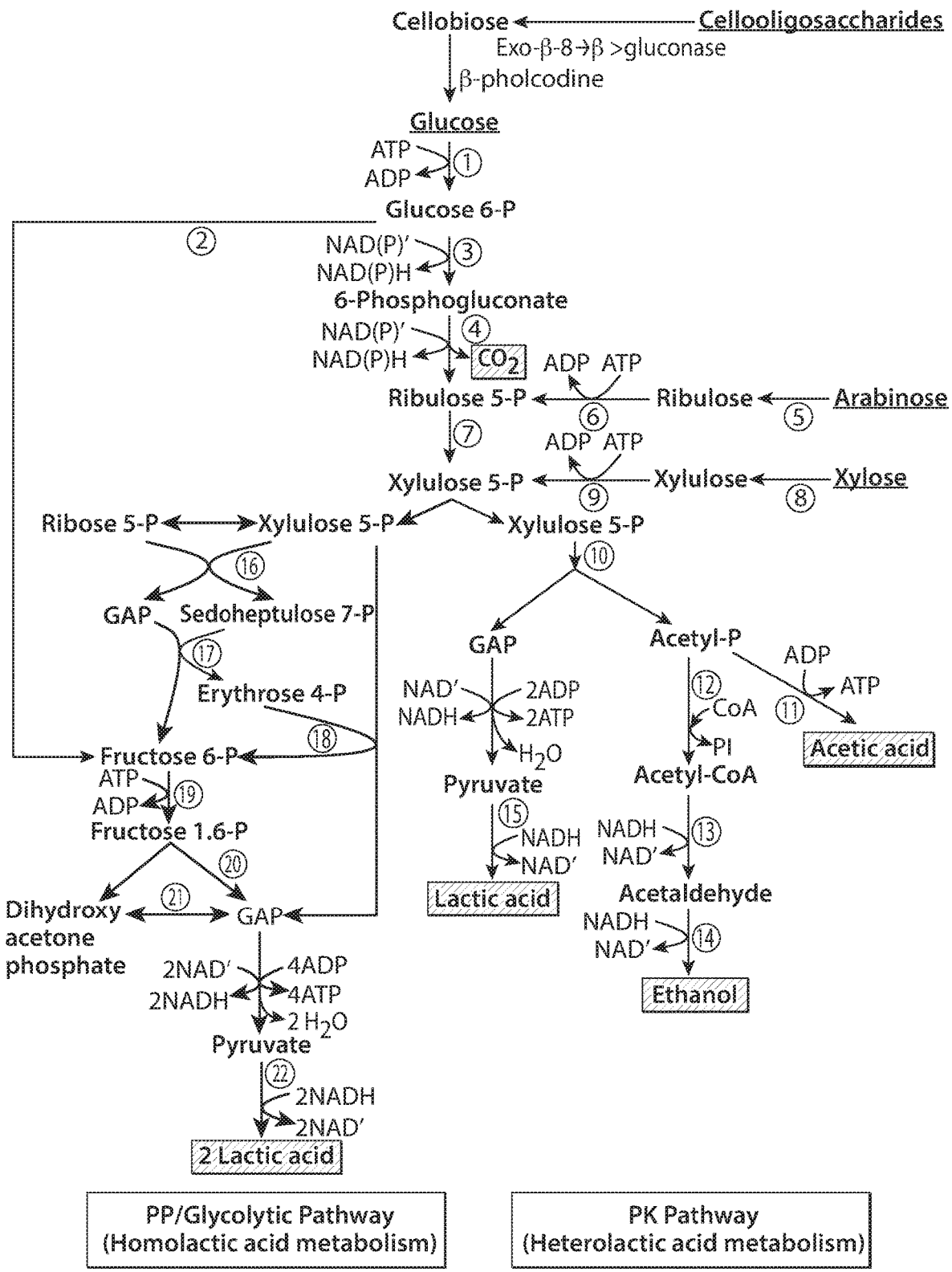
FIG. 2 is a schematic showing some biochemical pathways for the fermentation of sugars to lactic acid.
Figure 3:
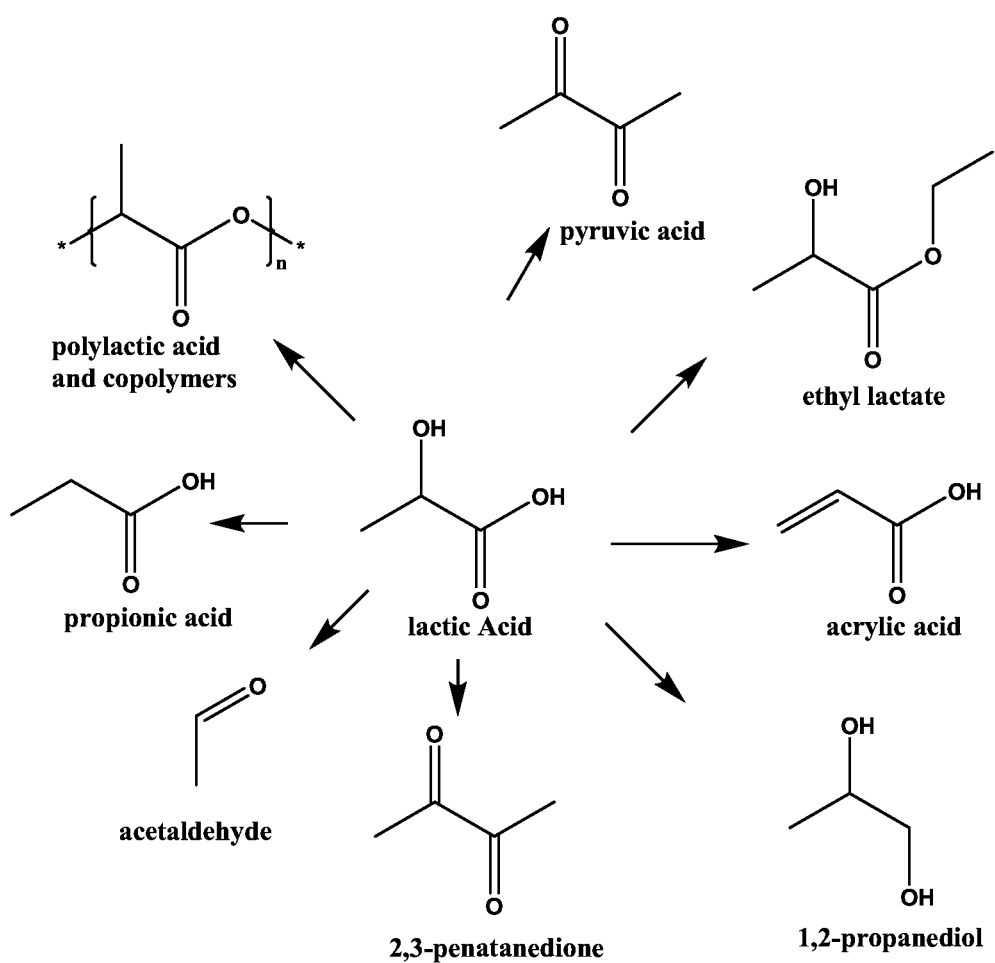
FIG. 3 is a schematic showing some of the possible lactic acid derived products.

Organisms can utilize a variety of metabolic pathways to convert the sugars to lactic acid, and some organisms selectively only can use specific pathways. Some organisms are homofermentative while others are heterofermentative. For example, some pathways are shown in FIG. 2 and are described in Journal of Biotechnology 156 (2011) 286-301. The pathway typically utilized by organisms fermenting glucose is the glycolytic pathway 2. Five carbon sugars, such as xylose, can utilize the heterofermentative phosphoketolase (PK) pathway. The PK pathway converts two of the 5 carbons in xylose to acetic acid on the remaining 3 to lactic acid (through pyruvate). Another possible pathway for five carbon sugars is the pentose phosphate (PP)/glycolytic pathway that only produces lactic acid.

Several organisms can be utilized to ferment the biomass derived sugars to lactic acid. The organisms can be, for example, lactic acid bacteria and fungi. Some specific examples include *Rhizopus arrhizus, Rhizopus oryzae*, (e.g., NRRL-395, ATCC 52311, NRRL 395, CBS 147.22, CBS 128.08, CBS 539.80, CBS 328.47, CBS 127.08, CBS 321.35, CBS 396.95, CBS 112.07, CBS 127.08, CBS 264.28), *Enterococcus faecalis* (e.g. RKY1), *Lactobacillus rhamnosus* (e.g. ATCC 10863. ATCC 7469, CECT-288, NRRL B-445), *Lactobacillus helveticus* (e.g. ATCC 15009, R211), *Lactobacillus bulgaricus* (e.g. NRRL B-548, ATCC 8001, PTCC 1332), *Lactobacillus casei* (e.g. NRRL B-441), *Lactobacillus plantarum* (e.g. ATCC 21028, TISTR No. 543, NCIMB 8826), *Lactobacillus pentosus* (e.g. ATCC 8041), *Lactobacillus amylophilus* (e.g. GV6), *Lactobacillus delbrueckii* (e.g. NCIMB 8130, TISTR No. 326, Uc-3, NRRL-B445, IFO 3202, ATCC 9649), *Lactococcus lactis* ssp. *lactis* (e.g. IFO 12007), *Lactobacillus paracasei* No. 8, *Lactobacillus amylovorus* (ATCC 33620), *Lactobacillus* sp. (e.g. RKY2), *Lactobacillus coryniformis* ssp. *torquens* (e.g. ATCC 25600, B-4390), *Rhizopus* sp. (e.g. MK-96-1196), *Enterococcus casseliflavus, Lactococcus lactis* (TISTR No. 1401), *Lactobacillus casei* (TISTR No. 390), *Lactobacillus thermophiles, Bacillus coagulans* (e.g., MXL-9, 36D1, P4-102B), *Enterococcus mundtii* (e.g., QU 25), *Lactobacillus delbrueckii, Acremonium cellulose, Lactobacillus bifermentans, Corynebacterium glutamicum, L. acetotolerans, L. acidifarinae, L. acidipiscis, L. acidophilus, L. agilis, L. algidus, L. alimentarius, L. amylolyticus, L. amylophilus, L. amylotrophicus, L. amylovorus, L. animalis, L. antri, L. apodemi, L. aviarius, L. bifermentans, L. brevis* (e.g., B-4527), *L. buchneri, L. camelliae, L. casei, L. catenaformis, L. ceti, L. coleohominis, L. collinoides, L. composti, L. concavus, L. coryniformis, L. crispatus, L. crustorum, L. curvatus, L. delbrueckii* subsp. *Delbrieckii* (e.g., NRRL B-763, ATCC 9649), *L. delbrueckii* subsp. *bulgaricus, L. delbrueckii* subsp. *lactis* (e.g., B-4525), *L. dextrinicus, L. dioliovorans, L. equi, L. equigenerosi, L. farraginis, L. farciminis, L. fermentum, L. fornicalis, L. fructivorans, L. frumenti, L. fuchuensis, L. gallinarum, L. gasseri, L. gastricus, L. ghanensis, L. graminis, L. hammesii, L. hamsteri, L. harbinensis, L. hayakitensis, L. helveticus, L. hilgardii, L. homohiochii, L. iners, L. ingluviei, L. intestinalis, L. jensenii, L. johnsonii, L. kalixensis, L. kefiranofaciens, L. kefiri, L. kimchii, L. kitasatonis, L. kunkeei, L. leichmannii, L. lindneri, L. malefermentans, L. mali, L. manihotivorans, L. mindensis, L. mucosae, L. murinus, L. nagelii, L. namurensis, L. nantensis, L. oligofermentans, L. oris, L. panis, L. pantheris, L. parabrevis, L. parabuchneri, L. paracollinoides, L. parafarraginis, L. parakefiri, L. paralimentarius, L. paraplantarum, L. pentosus, L. perolens, L. plantarum*(e.g., ATCC 8014), *L. pontis, L. psittaci, L. rennini, L. reuteri, L. rhamnosus, L. rimae, L. rogosae, L. rossiae, L. ruminis, L. saerimneri, L. sakei, L. salivarius, L. sanfranciscensis, L. satsumensis, L. secaliphilus, L. sharpeae, L. siliginis, L. spicheri, L. suebicus, L. thailandensis, L. ultunensis, L. vaccinostercus, L. vaginalis, L. versmoldensis, L. vini, L. vitulinus, L. zeae, L. zymae*, and *Pediococcus pentosaceus* (ATCC 25745).

Alternatively, the microorganism used for converting sugars to hydroxy-carboxylic acids, including lactic acid, *Lactobacillus casei, Lactobacillus rhamnosus, Lactobacillus delbrueckii* subspecies *delbrueckii, Lactobacillus plantarum, Lactobacillus coryniformis* subspecies *torquens, Lactobacillus pentosus, Lactobacillus brevis, Pediococcus pentosaceus, Rhizopus oryzae, Enterococcus faecalis, Lactobacillus helveticus, Lactobacillus bulgaricus, Lactobacillus casei, lactobacillus amylophilus* and mixtures thereof Using the methods, equipment and systems described herein, either D or L isomers of lactic acid at an optical purity of near 100% (e.g., at least about 80%, at least about 85%, at least about 90%, at least about 95%, at least about 99%) can be produced. Optionally, mixtures of the isomers can be produced in any ratio, for example, from 0% optical purity of any isomer up to 100% optical purity of any isomer. For example, the species *Lactobacillus delbrueckii* (NRRL-B445) is reported to produce a mixture of D and L isomers, *Lactobacillus rhamnosus* (CECT-28) is reported to produce the L isomer while *Lactobacillus delbrueckii* (IF 3202) is reported to produce the D isomer (Wang et al. in Bioresource Technology, June, 2010). As a further example, organisms that predominantly produce the L(+)-isomer are *L. amylophilus, L. bavaricus, L. casei, L. maltaromicus* and *L. salivarius*, while *L. delbrueckii, L. jensenii* and *L. acidophilus* produce the D(−)-isomer or mixtures of both.

Genetically modified organisms can also be utilized. For example, genetically modified organisms (e.g., *lactobacillus, Escherichia coli*) that are modified to express either L-Lactate dehydrogenase or D-lactate dehydrogenase to produce more L-Lactic acid or D-Lactic acid, respectively. In addition, some yeasts and *Escherichia coli* have been genetically modified to produce lactic acid from glucose and/or xylose.

Co-cultures of organisms, for example, chosen from organisms as described herein, can be used in the fermentations of sugars to hydroxy-carboxylic acid in any combination. For example, two or more bacteria, yeasts and/or fungi can be combined with one or more sugars (e.g., glucose and/or xylose) where the organisms ferment the sugars together, selectively and/or sequentially. Optionally, one organism can be added first and the fermentation proceed for a time, for example, until it stops fermenting one or more of the sugars, and then a second organism can be added to further ferment the same sugar or ferment a different sugar. Co-cultures can also be utilized, for example, to tune in a desirable racemic mixture of D and L lactic acid by combining a D-fermenting and L-fermenting organism in an appropriate ratio to form the targeted racemic mixture.

In some embodiments, fermentations utilize *Lactobacillus*. For example, the fermentation of biomass derived glucose by *Lactobacillus* can be very efficient (e.g., fast, selective and with high conversion). In other embodiments the production of lactic acid uses filamentous fungi. For example, *Rhizopus* species can ferment glucose aerobically to lactic acid. In addition, some fungi (e.g. *R. oryzae* and *R. arrhizus*) produce amylases so that the direct fermentation of starches can accomplished without adding external amylases. Finally some fungi (e.g., *R. oryzae*) can ferment xylose as well as glucose where most *lactobacillus* are not efficient in fermenting pentose sugars.

In some embodiments some additives (e.g., media components) can be added during the fermentation. For example, additives that can be utilized include yeast extract, rice bran, wheat bran, corn steep liquor, black strap molasses, casein hydrolyzate, vegetable extracts, corn steep solid, ram horn waste, peptides, peptone (e.g., bacto-peptone, polypeptone), pharmamedia, flower (e.g., wheat flour, soybean flour, cottonseed flour), malt extract, beef extract, tryptone, $K_2HPO_4$, $KH_2PO_4$, $Na_2HPO_4$, $NaH_2PO_4$, $(NH_4)_2PO_4$, $NH_4OH$, $NH_4NO$, urea. ammonium citrate, nitrilotriacetic acid, $MnSO_4.5H_2O$, $MgSO4.7H_2O$, $CaCl_2.2H_2O$, $FeSO_4.7H_2O$, B-vitamins (e.g., thiamine, riboflavin, niacin, niacinamide, pantothenic acid, pyridoxine, pyridoxal, pyridoxamine, pyridoxine hydrochloride, biotin, folic acid), amino acids, sodium-L-glutamate, $Na_2EDTA$, sodium acetate, $ZnSO_4.7H_2O$, ammonium molybdate tetrahydrate, $CuCl_2$, $CoCl_2$ and $CaCO_3$. Addition of protease can also be beneficial during the fermentation. Optionally, surfactants such as TWEEN™80 and antibiotics such as chloramphenicol can also be beneficial. Additional carbon sources, for example, glucose, xylose and other sugars. Antifoaming compounds such as Antifoam 204 can also be utilized.

In some embodiments the fermentation can take from about 8 hours to several days. For example, some batch fermentations can take from about 1 to about 20 days (e.g., about 1-10 days, about 3-6 days, about 8 hours to 48 hours, about 8 hours to 24 hours).

In some embodiments the temperature during the fermentation is controlled. For example, the temperature can be controlled between about 20° C. and 50° C. (e.g., between about 25 and 40° C., between about 30 and 40° C., between about 35 and 40°. C). In some cases, thermophilic organisms are utilized that operate efficiently above about 50° C., for example, between about 50° C. and 100°. C (e.g., between about 50-90°. C, between about 50 to 80°. C, between about 50 to 70°. C).

In some embodiments the pH is controlled, for example, by the addition of an acid or a base. The pH can be optionally controlled to be close to neutral (e.g., between about 4-8, between about 5-7, between about 5-6). Acids, for example, can be protic acids such as sulfuric, phosphoric, nitric, hydrochloride and acetic acids. Bases, for example, can include metal hydroxides (e.g., sodium and potassium hydroxide), ammonium hydroxide, and calcium carbonate. Phosphate and other buffers can also be utilized.

Fermentation methods include, for example, batch, fed batch, repeated batch or continuous reactors. Often batch methods can produce higher concentrations of lactic acids, while continuous methods can lead to higher productivities.

Fed batch methods can include adding media components and substrate (e.g., sugars from biomass) as they are depleted. Optionally, products, intermediates, side products and/or waste products, can be removed as they are produced. In addition, solvent (e.g., water) can be added or removed to maintain the optimal amount for the fermentation.

Options include cell-recycling. For example, using a hollow fiber membrane to separate cells from media components and products after fermentation is complete. The cells can then be re-utilized in repeated batches. In other optional methods, the cells can be supported, for example, as described in U.S. application Ser. No. 13/293,971, filed on Nov. 10, 2011 and U.S. Pat. No. 8,377,668, issued Feb. 19, 2013, the entire disclosures of which are herein incorporated by reference.

The fermentation broth can be neutralized using calcium carbonate or calcium hydroxide which can form calcium lactate. Calcium lactate is soluble in water (e.g., about 7.9 g/100 mL). The calcium lactate broth can then be filtered to remove cells and other insoluble materials. In addition the broth can be treated with a decolorizing agent. For example, the broth can be filtered through carbon. The broth is then concentrated, e.g., by evaporation of the water optionally under vacuum and/or mild heating, and can be crystallized or precipitated. Acidification, for example, with sulfuric acid, releases the lactic acid back into solution which can be separated (e.g., filtered) from the insoluble calcium salts, e.g., calcium sulfate. Addition of calcium carbonate during the fermentation can also serve as a way to reduce product inhibition since the calcium lactate is not inhibitory or causes less product inhibition.

Optionally, reactive distillation can also be used to purify D-lactic acid and/or L-lactic acid. For example, methylation of D-lactic acid and/or L-lactic acid provides the methyl ester which can be distilled to pure ester which can then be hydrolyzed to the acid and methanol that can be recycled. Esterification to other esters can also be used to facilitate the separation. For example, reactions with alcohols to the ethyl, propyl, butyl, hexyl, octyl or even esters with more than eight carbons can be formed and then extracted in a solvent or distilled.

Other alternative D-lactic acid and/or L-lactic acid separation technologies include adsorption, for example, on activated carbon, polyvinylpyridine, zeolite molecular sieves and ion exchange resins such as basic resins. Other methods include ultrafiltration and electrodialysis.

Precipitation or crystallization of calcium lactate by the addition of organic solvents is another method for purification. For example, alcohols (e.g., ethanol, propanol, butanol, hexanol), ketones (e.g., acetone) can be utilized for this purpose.

Similar methods can be utilized for the preparation of other hydroxy-carboxylic acids. For example, the fermentative methods and procedures can be applicable for any of the hydroxy-carboxylic acids described herein.

Lactic Acid Uses

Lactic acid produced as described herein can be used, for example, in the food industry as a preservative, acidulant and flavoring agent. Lactic acid can be used in a wide range of food applications such as bakery products, beverages, meat products, confectionery, dairy products, salads, dressings, ready meals. Lactic acid in food products usually serves either as a pH regulator or as a preservative. It is can also be used as a flavoring agent, for example, imparting a sour taste to foods. Lactic acid can be used in meat, poultry and fish, for example, in the form of sodium or potassium lactate to extend shelf life, control pathogenic bacteria (e.g., improving food safety), enhance and protect meat flavor, improve water binding capacity and reduce sodium. Lactic acid is also used as an acidity regulator in beverages such as soft drinks and fruit juices. Lactic acid is effective in preventing the spoilage of olives, gherkins, pearl onions and other vegetables preserved in brine. Lactic acid can also be used as a preservative and/or flavoring additive in salads and dressings. Lactic acid is also used in formulating hard-boiled candy, fruit gums and other confectionery products. Lactic acid is used as an acidification agent for many dairy products for example, yogurts and cheeses. Lactic acid is a natural sourdough acid, and therefore, it can be used for direct acidification in the production of sourdough. Lactic acid is used to enhance a broad range of savory flavors, for example, in meat and dairy products.

Calcium lactate as produced by the methods described herein can also be added to sugar-free foods to prevent tooth decay. For example, in combinations with chewing gum containing xylitol, it increases the remineralization of tooth enamel. Calcium lactate is also added to fresh-cut fruits such as cantaloupes to extend their shelf life.

The biomass derived lactic acid as described herein can be used in pharmaceutical applications, for example, for pH-regulation, metal sequestration, as a chiral intermediate and as a natural body constituent in pharmaceutical products. Calcium lactate is commonly used as an antacid and also as a calcium supplement. Other salts of lactic acid, for example, salts containing Mg, Zn and Fe, can also be used as mineral supplements and fortifying agents.

Lactic acid as produced by the methods described herein can also be used in cleaning products. Lactic acid has descaling properties and is widely applied in household cleaning products. Also, lactic acid is used as a natural anti-bacterial agent in disinfecting products.

The lactic acid produced by the methods described herein can be used in a wide variety of industrial processes where acidity is required and where its properties offer specific benefits. Examples are the manufacture of leather and textile products and computer disks, as well as car coatings.

The lactic acid as produced by the methods described herein can also be utilized as nutrient for animal feed. The lactic acid can have health promoting properties, thus enhancing the performance of farm animals. The lactic acid can be also used as an additive in food and/or drinking water both for animals and humans.

Products Derived from Lactic Acid

Lactic acid can be used as a platform chemical for many industrially relevant chemicals and products. For example, with reference to FIG. 2, lactic acid can be converted to, lactate esters such as ethyl lactate, acrylic acid, 1,2-propanediol, 2,3-pentanedione, acetaldehyde, propanoic acid and poly lactic acid.

1,2-propane diol (propylene glycol) can be used as a solvent and anti-freeze substitute for 1,2-propane diol. Propylene glycol is also used for de-icing solutions (e.g., airplane de-icing). Propylene glycol is approved for use as a food additive and can be used in food industry as a humectant, preservative, lubricant (e.g., for food processing equipment), solvent (e.g., for pharmaceutical preparations), plasticizer (e.g., for materials that come into contact with food).

Ethyl lactate has uses in pharmaceutical preparations, food additives, fragrances and as a fine chemical, consumer product (e.g., cosmetics) and industrial solvent.

Acetaldehyde is currently produced in a large scale, primarily from petroleum sources. It is a synthon in a myriad of organic reactions to produce, for example, ethyl acetate (an important solvent), perfumes, polyester resins and basic dyes. It also finds uses as a solvent (e.g., in the rubber, tanning and paper industries), as a preservative (e.g., fruit and meat), a flavoring agent and a denaturant for fuel compositions.

2,3-pentanedione is useful as a solvent for cellulose acetate, paints, inks, lacquers. It is also a starting material for the synthesis of dyes, pesticides and drugs. It also can be used as a constituent in synthetic flavoring agents.

(Meth)acrylic acid and its esters (e.g., methyl, butyl, ethyl, hydroxyethyl and 2-ethylhexyl esters) polymerize through their double bond to form poly acrylates (e.g., polyacrylic acid). In addition, acrylic acid and its esters can copolymerize with other monomers e.g., acrylamides, acrylonitriles, styrene, vinyl and butadiene) forming copolymers which are used in manufacturing plastics, coatings, adhesives, elastomers, floor polishes and paints.

Propanoic acid can be used as a fungicide and bactericide, for treatment of grains, hay, poultry litter, drinking water for animals as well as for the treatment of areas used for storage of feed materials. It is also a synthon for production of other chemicals, for example, herbicides and various esters.

Poly lactic acid is an important biodegradable/recyclable polymer that will be discussed in detail below.

Polymerization of Lactic Acid

Lactic acid prepared as described herein can undergo ester condensation to form dimers (e.g., linear and lactide), trimers, oligomers and polymers. Polylactic acid (PLA) is therefore, a polyester of condensed lactic acid. PLA can be further processed (e.g., grafted, treated, or copolymerized to form side chains including ionizable groups). Another name for PLA is polylactide. Both isomers of PLA can form polymers and/or they can be copolymerized. The properties of the polymer depend strongly on the amounts of the D and L lactic acid incorporated in the structure, as will be discussed further on.

Figure 4:
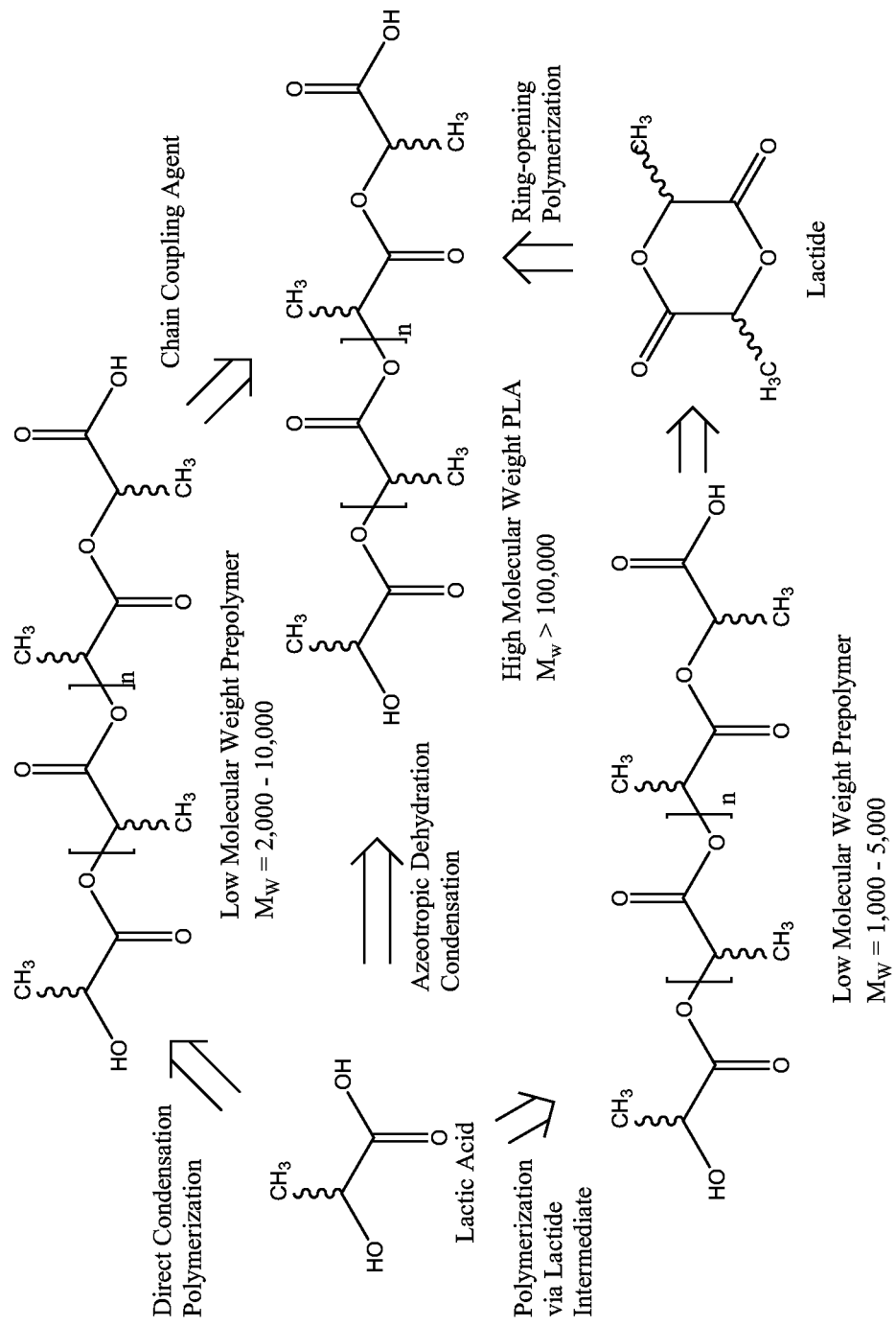
FIG. 4 is a schematic showing some possible chemical pathways for producing poly lactic acid.

FIG. 4 shows methods for the production of PLA including: direct condensation combined with chain coupling; azeotropic dehydrative coupling; and condensation followed by lactide formation and ring opening polymerization of the lactide.

A low molecular weight PLA can be produced catalyst free by the direct self-condensation of lactic acid. This method produces low molecular weight polymers (e.g., about 1000 to 10,000 Mw, more typically about 1000 to 5,000). The condensation produces water which can prevent the production of high molecular weight PLA since the ester condensation reaction is reversible. In addition, lactide can be produced by backbiting from a chain end to form the lactide ring which reduces the molecular weight of the linear polymer. Therefore, the polycondensation system of PLA involves two equilibrium reactions; the dehydration/hydrolysis equilibrium for esterification/de-esterification; and the ring/chain equilibrium involving the depolymerization of PLA into lactide or polymerization of the ring to linear polymer.

One method for production of high molecular weight PLA is by coupling low Mw PLA, for example, made as described above, using chain coupling agents. For example, hydroxyl-terminated PLA can be synthesized by the condensation of lactic acid in the presence of small amounts of multifunctional hydroxyl compounds such as, ethylene glycol, propylene glycol, 1,3-propanediol, 1,2-cyclohexanediol, 2-butene-1,4-diol, glycerol, 1,4-butanediol, 1,6-hexanediol. Alternatively, carboxyl-terminated PLA can be achieved by the condensation of lactic acid in the presence of small amounts of multifunctional carboxylic acids such as maleic, succinic, adipic, itaconic and malonic acid. Other chain extending agents can have heterofunctional groups that couple either on the carboxylic acid end group of the PLA or the hydroxyl end group, for example, 6-hydroxycapric acid, mandelic acid, 4-hydroxybenzoic acid, 4-acetoxybenzoic acid.

Esterification promotion agents can also be combined with lactic acid to increase the molecular weight of PLA. For example, ester promotion agents include phosgene, diphosgene, triphosgene dicyclohexylcarbodiimide and carbonyldiimidazole. Some potentially undesirable side products can be produced by this method adding purification steps to the process. After final purification, the product can be very clean, free of catalysts and low molecular weight impurities.

The polymer molecular weights can also be increase by the addition of chain extending agents such as isocyanates, acid chlorides, anhydrides, epoxides, thiirane and oxazoline and orthoester.

Azeotropic condensation polymerization is another method to obtain high molecular weight polymer and does not require chain extenders or coupling agents. A general procedure for this route consists of reduced pressure (between 0.1-300 mm Hg) refluxing of lactic acid for 1-10 hours between 110° C.-160° C. to remove majority of the condensation water. Catalyst and/or solvents are added and heated further for 1-10 hours between 110° C.-180° C. under 0.1-300 mm Hg. The polymer is then isolated or dissolved (methylene chloride, chloroform) and precipitated by the addition of a solvent (e.g., methyl ether, diethyl ether, methanol, ethanol, isopropanol, ethyl acetate, toluene) for further purification. Solvents used during to polymerization, catalyst, reaction time, temperature and level of impurities effect the rate of polymerization and hence the final molecular weight.

Additives, catalysts and promoters that can optionally be used include Lewis and Bronsted (protonic) acids such as $H_3PO_4$, $H_2SO_4$, methane sulfonic acid, p-toluene sulfonic acid, NAFION® NR 50 H+ form From DuPont, Wilmington Del., metal catalysts, for example, include Mg, Al, Ti, Zn, Sn. Some metal oxides that can optionally catalyze the reaction include $TiO_2$, ZnO, $GeO_2$, $ZrO_2$, SnO, $SnO_2$, $Sb_2O_3$. Metal halides, for example, that can be beneficial include $ZnCl_2$, $SnCl_2$, $SnCl_4$. Other metal containing catalysts that can optionally be used include $Mn(AcO)_2$, $Fe_2(LA)_3$, $Co(AcO)_2$, $Ni(AcO)_2$, $Cu(OA)_2$, $Zn(LA)_2$, $Y(OA)_3$, $Al(i-PrO)_3$, $Ti(BuO)_4$, $TiO(acac)_2$, $(Bu)_2SnO$. Combinations and mixtures of the above catalysts can also be used. For example, two or more catalysts can be added at one time or sequentially as the polymerization progresses. The catalysts can also be removed, replenished and/or regenerated during the course of the polymerization are for repeated polymerizations. Optional combinations include protonic acids and one of the metal continuing catalysts, for example, $SnCl_2$/p-toluenesulfonic acid.

The azeotropic condensation can be done partially or entirely using a solvent. For example, a high boiling and aprotic solvent such as diphenyl ether, p-xylene, o-chlorotoluene, o-dichlorobenzene and/or isomers of these. The polymerization can also be done entirely or partially using melt polycondensation. Melt polycondensations are done above the melting point of the polymers/oligomers without organic solvents. For example, at the beginning of the polymerization when there is a high concentration of low molecular weight species (e.g., lactic acid and oligomers) there can be less need for a solvent, while as the molecular weight of the polymers increases, the addition of a high boiling solvent can improve the reaction rates.

During the polymerization, for example, especially at the beginning of the polymerization when the concentration of lactic acid is high and water is being formed at a high rate, the lactic acid/water azeotropic mixture can be condensed and made to pass through molecular sieves to dehydrate the lactic acid which is then returned to the reaction vessel.

Copolymers can be produced by adding monomers other than lactic acid during the azeotropic condensation reaction. For example, any of the multifunctional hydroxyl, carboxylic compounds or the heterofunctional compounds that can be used as coupling agents for low molecular weight PLA can also be used as co-monomers in the azeotropic condensation reaction.

Optionally, ring opening polymerization of lactide can provide PLA. Lactide can be produced by the depolymerization of low molecular weight PLA under reduced pressure. The depolymerization to form the lactide monomers, for example, the D, L and meso forms, depends on the stereochemistry of the starting lactic acid and conditions of formation. Methods to form the lactide include condensing lactic acid, with or without catalysts at 110-180° C. and removing the water of condensation under vacuum (1 mm Hg-100 mm Hg) to produce 1000-5000 molecular weight polymer or prepolymer. The prepolymer can then be heated, for example, to temperatures of about 150-250° C. and at 0.1-100 mmHg to form and distill off the crude lactic acid. The crude lactic acid can be recrystallized, for example, from a solution of dry toluene or ethyl acetate.

Catalysts can be used for lactide formation. For example, catalysts that can be used include, tin oxide (SnO), Sn(II) octoate, Li carbonate, Zinc diacetate dehydrate, Ti tetraisopropoxide, potassium carbonate, tin powder, combinations thereof and mixtures of these. Catalysts can be used in combination and/or sequentially.

The lactide monomer can be ring open polymerized (ROP) by solution, bulk, melt and suspension polymerization and is catalyzed by cationic, anionic, coordination or free radical polymerization. Some catalysts used, for example, include protonic acids, HBr, HCl, triflic acid, Lewis acids, $ZnCl_2$, $AlCl_3$, anions, potassium benzoate, potassium phenoxide, potassium t-butoxide, and zinc stearate, metals, Tin, zinc, aluminum, antimony, bismuth, lanthanide and other heavy metals, Tin (II) oxide and tin (II) octoate (e.g., 2-ethylhexanoate), tetraphenyl tin, tin (II) and (IV) halogenides, tin (II) acetylacetonoate, distannoxanes (e.g., hexabutyldistannoxane, $R_3SnOSnR_3$ where R groups are alkyl or aryl groups), $Al(OiPr)_3$, other functionalized aluminum alkoxides (e.g., aluminum ethoxide, aluminum methoxide), ethyl zinc, lead (II) oxide, antimony octoate, bismuth octoate, rare earth catalysts, yttrium tris(methyl lactate), yttrium tris(2-N-N-dimethylamino ethoxide), samarium tris(2-N-N-dimethylamino ethoxide), yttrium tris(trimethylsilyl methyl), lanthanum tris(2,2,6,6-tetramethyl-heptanedionate), lanthanum tris(acetylacetonate), yttrium octoate, yttrium tris(acetylacetonate), yttrium tris(2,2,6,6-tetramethylheptanedionate), combinations of these (e.g., ethyl zinc/aluminum isopropoxide) and mixtures of these.

In addition to homopolymer, copolymerization with other cyclic monomers and non-cyclic monomers such as glycolide, caprolactone, valerolactone, dioxypenone, trimethyl carbonate, 1,4-benzodioxepin-2,5-(3H)-dione glycosalicylide, 1,4-benzodioxepin-2,5-(3H,3-methyl)-dione Lactosalicylide, dibenzo-1,5 dioxacin-6-12-dione disalicylide, morpholine-2,5-dione, 1,4-dioxane-2,5-dione glycolide, oxepane-2-one ε-caprolactone, 1,3-dioxane-2-one trimethylene carbonate, 2,2-dimethyltrimethylene carbonate, 1,5-dioxepane-2-one, 1,4-dioxane-2-one p-dioxanone, gamma-butyrolactone, beta-butyrolactone, beta-me-delta-valerolactone, 1,4-dioxane-2,3-dione ethylene oxalate, 3-[benzyloxycarbonyl methyl]-1,4-dioxane-2,5-dione, ethylene oxide, propylene oxide, 5,5'(oxepane-2-one), 2,4,7,9-tetraoxa-spiro[5,5]undecane-3,8-dione Spiro-bid-dimethylene caronate can produce co-polymers. Copolymers can also be produced by adding monomers such as the multifunctional hydroxyl, carboxylic compounds or the heterofunctional compounds that can be used as coupling agents for low molecular weight PLA.

Figure 5:
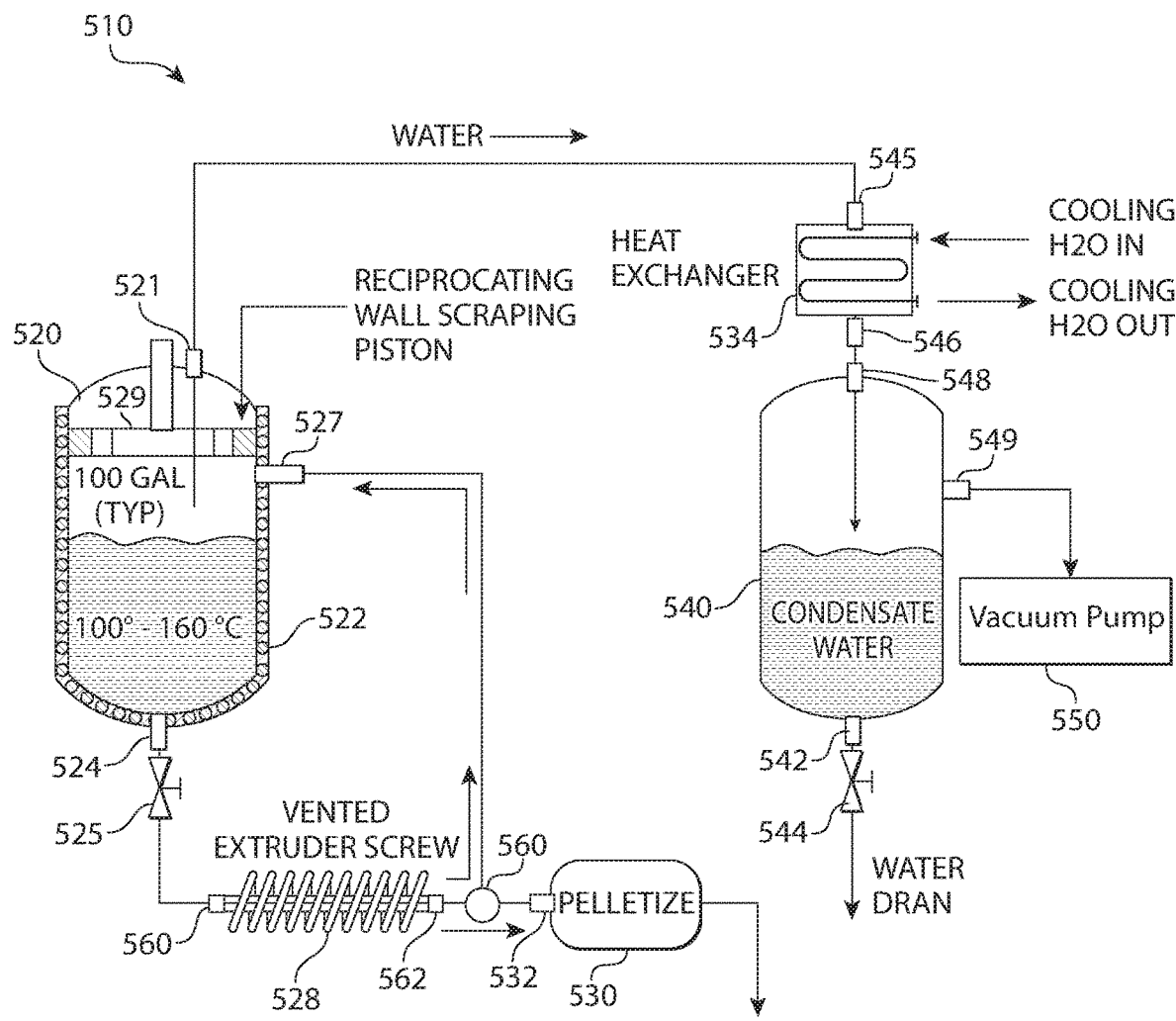
FIG. 5 is a schematic view of a reaction system for polymerizing lactic acid.

FIG. 5 shows a schematic view of a reaction system for polymerizing lactic acid. The reaction system (510) includes a stainless steel jacked reaction tank (520), a vented screw extruder (528), a pelletizer (530), a heat exchanger (534) and a condensation tank (540). An outlet (521) of the reaction tank is connected to a tube (e.g., stainless steel) which is connected to an inlet (545) to a heat exchanger. An outlet (546) to the heat exchanger is connected to another tube (e.g., stainless steel or other corrosive resistant material) and is connected to an inlet (548) to the condensation tank (540). The tubes and connections from the reaction tank and condensation tank provide a fluid pathway (e.g., water vapor/air) between the two tanks. A vacuum can be applied to the fluid pathway between the tanks (520) and (540) by utilizing a vacuum pump (550) that is connected to port (549).

The reaction tank (520) includes an outlet (524) that can be connected to a tube (e.g., stainless steel) that is connected to an inlet to a screw extruder (560). An outlet to the extruder (562) is connected to a tube which is connected optionally through a valve (560) to the reaction tank (520) through inlet (527). Optionally the outlet to the extruder (562) is connected through valve (560) to the pelletizer (530) through inlet (532). Tubes and connections from the reaction tank and extruder provide a circular fluid pathway (e.g., reactants and products) between the reaction tank and extruder when the valve (560) is set in recirculating position. The tubes and connections from the reaction tank to the pelletizer provide a fluid pathway between the reaction tank and pelletizer when the valve (560) is set in pelletizing position.

When in operation, the tank can be charged with lactic acid. The lactic acid is heated in the tank utilizing the stainless steel heating jacket (522). In addition, a vacuum is applied to the condensation tank (540) and therefore to the reaction tank (520) through the stainless steel tubing and connections using the vacuum pump (550). The heating of the lactic acid accelerates the condensation reactions (e.g., esterification reactions) to form oligomers of PLA while the applied vacuum helps volatilize the water that is produced. Water vapor travels out of the reactants and out of the reaction tank (520) and towards the heat exchanger (534) as indicated by the arrow. The heat exchanger cools the water vapor and the condensed water drops into the condensation tank (540) through the tubes and connections previously described. Multiple heat exchangers can be utilized. Since the hydroxy-carboxylic acids can be corrosive the reactor equipment and other associated equipment may be clad or coated with corrosive resistant metals such as tantalum, alloys such as HASTELLOY™, a trademarked alloy from Haynes International, and the like. It can also be coated with inert high temperature polymeric coatings such as TEFLON™ from DuPont, Wilmington De. The corrosivity of the hydroxy-carboxylic acid system may not be surprising since the pKa of lactic acid is more than 0.8 less than acetic acid. Also, water undoubtedly hydrates the acid and the acid end of the polymer. When those waters of hydration are removed the acidity can be much higher, since it is not leveled by the waters of hydration.

In addition, during operation, extruder (528) can be engaged and operated to draw the reactants (e.g., lactic acid, oligomers and polymers) out of the tank. When the valve (560) is set in recirculating position the reactants are circulated back to the reaction tank in the direction shown by the arrows. In addition to the extruder, the flow can be controlled by valve (525), for example, the valve can be set to closed for no flow, open for maximal flow or an intermediate position for lower or high flow rates (e.g., between about 0 and 100% open, e.g., about 0%, 10%, 20%, 30%, 40%, 50%, 60%, 70%, 80%, 90% or about 100% open).

The reaction can be continued with reactants following a circular pathway (e.g., with valve in recirculating position) until a desired polymerization is achieved. This circulating pathway provides mixing and shearing that can help the polymerization (e.g., increase molecular weight, control polydispersity, improve the kinetics of the polymerization, improve temperature distribution and diffusion of reacting species). The products (e.g. polymer) can then be directed to the pelletizer by setting valve (560) to the pelletizing position. The pelletizer then can produce pellets which can be collected. Pellets can be of various shapes and sizes. For example, spherical or approximately spherical, hollow tube shaped, filled tube shape with, for example, approximate volumes, between about 1 mm$^3$ to about 1 cm$^3$. The pelletizer can also be replaced with other equipment, for example, extruders, mixers, reactors, and filament makers.

The extruder (528) can be a vented screw extruder so that water or other volatile compounds can be removed from further processing. The extruder can be a single screw extruder or a multiple screw extruder. For example, the extruder can be a twin screw extruder with co-rotating or counter rotating screws. The screw extruder can also be a hollow flight extruder and can be heated or cooled. The screw extruder can be fitted with ports to its interior. The ports can be utilized, for example, for the addition of additives, addition of co-monomers, addition of cross-linking agents, addition of catalysts, irradiation treatments and addition of solvents. The ports can also be utilized for sampling (e.g., to test the progress of the reaction or troubleshoot). In addition to sampling, the torque applied to the extruder can be used to monitor the progress of the polymerization (e.g., as the viscosity increases). An inline (e.g., a static mixer) mixer can also be disposed in the pathway of the circulating reactants, for example, before or after the screw extruder, providing a tortuous path for the reactants which can improve the mixing supplied to the reactants. The extruder can be sized, for example, so that the material is recirculated, e.g., about 0.25-10 times per hour (e.g., about 1-5 or 1-4 times per hour).

The position of the return port (527) allows the reactants to flow down the side of the tank, increasing the surface area of the reactants facilitating the removal of water. The return port can include multiple (e.g. a plurality of ports) disposed at various positions in the tanks. For example, the plurality of return ports can be placed circumferentially around the tank.

The tank can include a reciprocating scraper (529) which can help push the formed polymer/oligomers down the reaction tank, for example, during or after completion of the reaction. Once the reciprocating scraper moves down, the scraper can then be moved back up, for example, to a resting position. The scraper can be moved up and down the tank by engaging with and axel (640) that is attached to the hub (650). In another possible embodiment, the hub can be tapped for mechanical coupling to a screw, for example, wherein the axel is a screw-axel that extends to the bottom of the tank. The screw-axel can then turn to drive the scraper down or up.

Figure 6A:
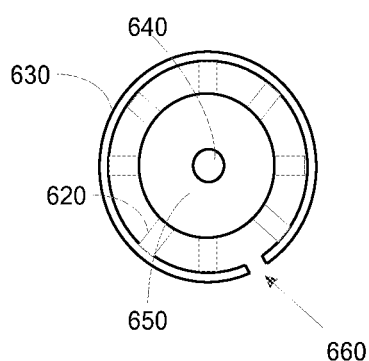
FIG. 6A is a top view of a first embodiment of a reciprocating scraper.
Figure 6C:
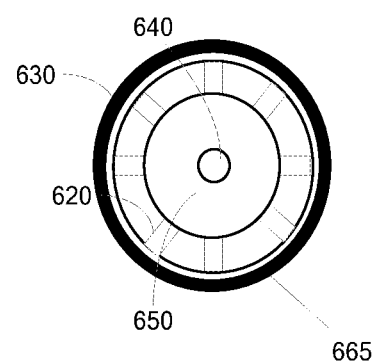
FIG. 6C is a top view of a second embodiment of a reciprocating scraper.
Figure 6B:
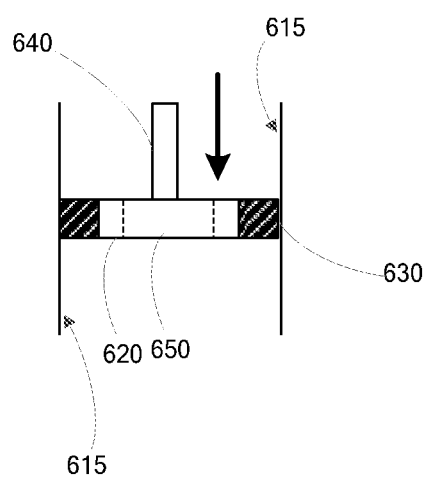
FIG. 6B is a front cut-out view of the first embodiment of a reciprocating scraper.

A top view of one embodiment of a reciprocating scraper is shown in FIG. 6A while a front cut out view is shown in FIG. 6B. The reciprocating scraper includes pistons (620) attached to a hub (650) and scraping ends (630). The scraping end is in the form of a compression ring with a gap (660). The pistons apply pressure against the inside surfaces of the tank (615) through the scraping ends (630) while the scraper can be moved down the tank as shown by the arrow in FIG. 6B. The gap (660) allows the expansion and contraction of the scraper. The scraper can be made of any flexible material, for example, steel such as stainless steel. The gap is preferably as small as possible (e.g., less than about 1", less than about 0.1", less than about 0.01" or even less than about 0.001").

Figure 6D:
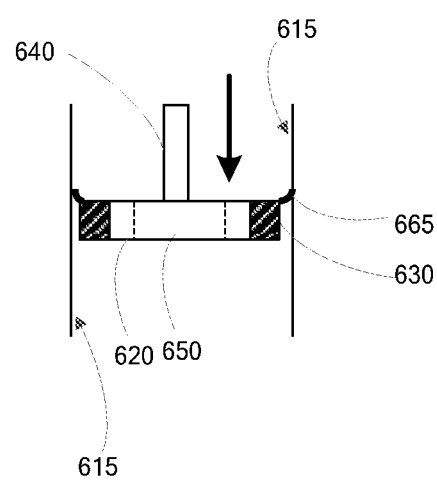
FIG. 6D is a front cut-out view of the second embodiment of a reciprocating scraper.

Another embodiment of a reciprocating scraper is shown in FIG. 6C and FIG. 6D. In this second embodiment the scraping ends include a lip-seal. The lip seal can be made of a flexible material, for example, rubber. The movement of the lip-seal as the scraper moves up and down acts as a squeegee against the inside of the reaction tank.

The tank (520) can be 100 gal in size, although larger and smaller sizes can be utilized (e.g., between about 20 to 10,000 gal, e.g., at least 50 gal, at least 200 gal, at least 500 gal, at least 1000 gal). The tank, for example, can be shaped with a conical bottom or rounded bottom.

In addition to the inlets and outlets discussed, the tank can also include other openings, for example, to allow the addition of reagents or for access to the interior of the tank for repairs.

During the reaction the temperature in the tank can be controlled from between about 100 and 180° C. The polymerization can preferably started at about 100° C. and the temperature increased to about 160° C. over several hours (e.g., between 1 and 48 hours, 1 and 24 hours, 1 and 16 hours, 1 and 8 hours). A vacuum can be applied between about 0.1 and 2 mmHg). For example, at the beginning of the reaction about 0.1 mmHg and at the end of the reaction about 2 mmHg.

Water from the condenser tank (540) can be drained trough an opening (542) utilizing control valve (544).

The heat exchanger can be a fluid cooled heat exchanger. For example, cooled with water, air or oil. Several heat exchangers can be used, for example, as needed to condense as much of the water as possible. For example, a second heat exchanger can be located between the vacuum pump and the condensation tank (540).

The equipment and reactions described herein (e.g., FIG. 5) can also be used for polymerization of other monomers. In addition, the equipment can be utilized after or during the polymerizations for blending of polymers. For example, any of the hydroxyl acids described herein can be polymerized by the methods, equipment and system described herein.

In addition to chemical method, lactic acid can be polymerized by LA-polymerizing enzymes and organisms. For example, ROP can be catalyzed by *Candida antarctica* lipase B, and hydrolases.

PLA Sterochemistry

Mechanical and thermal properties of pure PLA are largely determined by the molecular weight and stereochemical composition of the backbone. The stereochemical composition of the backbone can be controlled by the choice and ratios of monomers; D-Lactic acid, L-Lactic acid or alternatively D-Lactide, L-Lactide or meso-Lactide. This stereochemical control allows the formation of random or block stereo copolymers. The molecular weight of the polymers can be controlled, for example, as discussed above. The ability to control the stereochemical architecture allows, for example, precise control over the speed and degree of crystallinity, the mechanical properties, and the melting point and glass transition temperatures of the material.

The degree of crystallinity of PLA influences the hydrolytic stability of the polymer, and therefore, the biodegradability of the polymer. For example, highly crystalline PLA can take from months to years to degrade, while amorphous samples can be degraded in a few weeks to a few months. This behavior is due in part to the impermeability of the crystalline regions of PLA. Table 1 shows some of the thermal properties of some PLA of similarly treated samples. The percent crystallinity can be calculated by using data form the table and applying the equation.

$$\% \chi_c = \frac{(\Delta H_m - \Delta H_c)}{93} \cdot 100$$

Where $\Delta H_m$ is the melting enthalpy in J/g, $\Delta H_c$ is the crystallization enthalpy in J/g and 93 is the crystallization enthalpy of a totally crystalline PLA sample in J/g.

As can be calculated from the data in the table, the crystallinity is directly proportional to the molecular weight of the pure L or pure D stereo polymer. The DL stereoisomer (e.g., atactic polymer) is amorphous.

TABLE 1

Thermal properties of PLA

| Isomer type | $M_n \times 10^3$ | $M_w/M_n$ | $T_g$ (° C.) | $T_m$ (° C.) | $\Delta H$ (J/g) | $T_c$ (° C.) | $\Delta H$ (J/g) |
| --- | --- | --- | --- | --- | --- | --- | --- |
| L  | 4.7  | 1.09 | 45.6 | 157.8 | 55.5 | 98.3  | 47.8 |
| DL | 4.3  | 1.90 | 44.7 | —     | —    | —     | —    |
| L  | 7.0  | 1.09 | 67.9 | 159.9 | 58.8 | 108.3 | 48.3 |
| DL | 7.3  | 1.16 | 44.1 | —     | —    | —     | —    |
| D  | 13.8 | 1.19 | 65.7 | 170.3 | 67.0 | 107.6 | 52.4 |
| L  | 14.0 | 1.12 | 66.8 | 173.3 | 61.0 | 110.3 | 48.1 |
| D  | 16.5 | 1.20 | 69.1 | 173.5 | 64.6 | 109.0 | 51.6 |
| L  | 16.8 | 1.32 | 58.6 | 173.4 | 61.4 | 105.0 | 38.1 |

Calculated crystallinities are in order top to bottom: 8.2%, 0%, 11.3%, 0%, 15.7%, 13.8%, 14.0% and 25%.

The thermal treatment of samples, for example, rates of melting, recrystallization, and annealing history, can in part determine the amount of crystallization. Therefore, comparisons of the thermal, chemical and mechanical properties of PLS polymers should generally be most meaningful for polymers with a similar thermal history.

The pure L-PLA or D-PLA has a higher tensile strength and low elongation and consequently has a higher modulus than DL-PLA. Values for L-PLA vary greatly depending on how the material is made e.g., tensile strengths of 30 to almost 400 MPa, and tensile modulus between 1.7 to about 4.5 GPa.

PLA Copolymers, Crosslinking and Grafting

Variation of PLA by the formation of copolymers as discussed above also has a very large influence on the properties, for example, by disrupting and decreasing the crystallinity and modulating the glass transition temperatures. For example, polymers with increased flexibility, improved hydrophilicity, better degradability, better biocompatibility, better tensile strengths, improved elongations properties can be produced.

In many cases, the improvements are correlated with a decrease in the glass transition temperature. A few monomers can increase the glass transition temperature of PLA. For example, lactones of salicylic acids can have homopolymer glass transition temperatures between about 70 and 110° C. and polymerize with lactide.

Morpholinediones, which are half alpha-hydroxy carboxylic acids and half alpha-amino acids co-polymerize with lactide to give high molecular weight random co-polymers with lower glass transition temperatures (e.g., following the Flory-Fox equation). morpholinediones made up of glycine and lactic acid (6-methyl-2,5-morpholinedione) when copolymerized with lactide can give a polymer with glass transition temperatures of 109 and 71° C. for a 50 and 75 mol % lactic acid respectively in the polymer. Morpholinediones have been synthesized using glycolic acid or lactic acid and most of the alpha amino acids (e.g., glycine, alanine, aspartic acid, lysine, cysteine, valine and leucine). In addition to lowering the glass transition temperature and improving mechanical properties, the use of functional amino acids in the synthesis of morpholinediones is an effective way of incorporating functional pendant groups into the polymer.

As an example, copolymers of glycolide and lactide can be useful as biocompatible surgical sutures due to increased flexibility and hydrophilicity. The higher melting point of 228° C. and Tg of 37° C. for polyglycolic acid can produce a range of amorphous co-polymers with lower glass transition temperatures than PLA. Another copolymerization example is copolymerization with e-caprolactone which can yield tough polymers with properties ranging from ridged plastics to elastomeric rubbers and with tensile strengths ranging from 80 to 7000 psi, and elongations over 400%. Co-polymers of beta-methyl-gamma-valerolactone have been reported to produce rubber-like properties. Co-polymers with polyethers such as poly(ethylene oxide), poly (propylene oxide) and poly(tetramethylene oxide) are biodegradable, biocompatible and flexible polymers.

Some additional useful monomers that can be copolymerized with lactide include 1,4-benzodioxepin-2,3(H)-dione glycosalicylide; 1.3-benzodioxepin-2,5-(3H,3-methyl)-dione Lactosalicylide; dibenzo-1,5-dioxacin-6,12-dione disalicylide; morpholine-2,5-dione, 1,4-dioxane-2,5-dione, glycolide; oxepane-2-one trimethylene carbonate; 2,2-dimethyltrimethylene carbonate; 1,5-dioxepane-2-one; 1,4-dioxane-2-one p-dioxanone; gamma-butyrolactone; beta-butyrolactone; beta-methyl-delta-valerolactone; beta-methyl-gamma-valerolactone; 1,4-dioxane-2,3-dione ethylene oxalate; 3[(benzyloxycarbonyl)methyl]-1,4-dioxane-2,5-dione; ethylene oxide; propylene oxide, 5,5'-(oxepane-2-one) and 2,4,7,9-tetraoxa-spiro[5,5]undecane-3,8-dione Spiro-bis-dimethylene caronate.

PLA polymers and co-polymers can be modified by cross linking. Cross linking can affect the thermal and rheological properties without necessarily deteriorating the mechanical properties. For example, 0.2 mol % 5,5'-bis(oxepane-2-one) (bis-ε-caprolactone)) and 0.1-0.2 mol % spiro-bis-dimethylene carbonate cross linking. Free radical hydrogen abstraction reactions and subsequent polymer radical recombination is an effective way of inducing crosslinks into a polymer. Radicals can be generated, for example, by high energy electron beam and other irradiation (e.g., between about 0.01 Mrad and 15 Mrad, e.g. between about 0.01-5 Mrad, between about 0.1-5 Mrad, between about 1-5 Mrad). For example, irradiation methods and equipment are described in detail below.

Alternatively or in addition, peroxides, such as organic peroxides are effective radical producing and cross linking agents. For example, peroxides that can be used include hydrogen peroxide, dicumyl peroxide; benzoyl peroxide; 2,5-Dimethyl-2,5-di(tert-butylperoxy)hexane; tert-butylperoxy 2-ethylhexyl carbonate; tert-amyl peroxy-2-ethylhexanoate; 1,1-di(tert-amylperoxy)cyclohexane; tert-amyl peroxyneodecanoate; tert-amyl peroxybenzoate; tert-amylperoxy 2-ethylhexyl carbonate; tert-amyl peroxyacetate; 2,5-dimethyl-2,5-di(2-ethylhexanoylperoxy)hexane; tert-butyl peroxy-2-ethylhexanoate; 1,1-di(tert-butylperoxy)cyclohexane; tert-butyl peroxyneodecanoate; tert-butyl peroxyneoheptanoate; tert-butyl peroxydiethylacetate; 1,1-di(tert-butylperoxy)-3,3,5-trimethylcyclohexane; 3,6,9-triethyl-3,6,9-trimethyl-1,4,7-triperoxonane; di(3,5,5-trimethylhexanoyl) peroxide; tert-butyl peroxyisobutyrate; tert-butyl peroxy-3,5,5-trimethylhexanoate; di-tert-butyl peroxide; tert-butylperoxy isopropyl carbonate; tert-butyl peroxybenzoate; 2,2-di(tert-butylperoxy)butane; di(2-ethylhexyl) peroxydicarbonate; di(2-ethylhexyl) peroxydicarbonate; tert-butyl peroxyacetate; tert-butyl cumyl peroxide; tert-amylhydroperoxide; 1,1,3,3-tetramethylbutyl hydroperoxide, and mixtures of these. The effective amounts can vary, for example, depending on the peroxide, cross-linking reaction conditions and the desired properties (e.g., amount of cross linking). For example, cross-linking agents can be added from between about 0.01-10 wt. % (e.g., about 0.1-10 wt. %, about 0.01-5 wt. %, about 0.1-1 wt. %, about 1-8 wt. %, about 4-6 wt. %). For example, peroxides such as 5.25 wt. % dicumyl peroxide and 0.1% benzoyl peroxide are effective radical producing and cross linking agents for PLA and PLA derivatives. The peroxide cross-lining agents can be added to polymers as solids, liquids or solutions, for example, in water or organic solvents such as mineral spirits. In addition radical stabilizers can be utilized.

Cross linking can also be effectively accomplished by the incorporation of unsaturation in the polymer chain either by: initiation with unsaturated alcohols such as hydroxyethyl methacrylate or 2-butene-1,4-diol; the post reaction with unsaturated anhydrides such as maleic anhydride to transform the hydroxyl chain end; or copolymerization with unsaturated epoxides such as glycidyl methacrylate.

In addition to cross linking, grafting of functional groups and polymers to a PLA polymer or co-polymer is an effective method of modifying the polymer properties. For example, radicals can be formed as described above and a monomer, functionalizing polymer or small molecule. For example, irradiation or treatment with a peroxide and then quenching with a functional group containing an unsaturated bond can effectively functionalize the PLA backbone.

PLA Blending

PLA can be blended with other polymers as miscible or immiscible compositions. For immiscible blends, the composition can be one with the minor component (e.g., bellow about 30 wt. %) as small (e.g., micron or sub-micron) domains in the major component. When one component is about 30 to 70 wt. % the blend forms a co-continuous morphology (e.g., lamellar, hexagon phases or amorphous continuous phases).

Blending can be accomplished by melt mixing above the glass transition temperature of the amorphous polymer components. Screw extruders (e.g., single screw extruders, co-rotating twin screw extruders, counter rotating twin screw extruders) can be useful for this. For PLA polymers and co-polymers temperatures below about 200° C. can be used to avoid thermal degradation (e.g. below about 180° C.). Therefore, polymers that require higher processing temperatures are not generally good candidates for blending with PLA.

Polyethylene oxide (PEO) and polypropylene oxide (PPO) can be blended with PLA. Lower molecular weight glycols (300-1000 Mw) are miscible with PLA while PPO becomes immiscible at higher molecular weight. These polymers, especially PEO, can be used to increase the water transmission and bio-degradation rate of PLA. They can also be used as polymeric plasticizers to lower the modulus and increase flexibility of PLA. High molecular weight PEG (20,000) is miscible in PLA up to about 50%, but above that level the PEG crystallizes, reducing the ductility of the blend.

Polyvinyl acetate (PVA) is miscible with PLA in all concentrations, where the blends show only one Tg is observed at all blend ratios, with a constant decrease to about 37° C. at 100% PVA. Low levels of PVA (5-10%)

increase the tensile strength and % elongation of PLA while significantly reducing the rate of weight loss during biodegradation.

Blends of PLA and polyolefins (polypropylene and polyethylene) result in incompatible systems with poor physical properties due to the poor interfacial compatibility and high interfacial energy. However, the interfacial energy can be lowered, for example, by the addition of third component compatibilizers, such as glycidyl methacrylate grafted polyethylene. (irradiation would probably work) Polystyrene and high impact polystyrene resins are also non-polar and blends with PLA are generally not very compatible PLA and acetals can be blended making compositions with useful properties. For example, good, high transparency.

PLA is miscible with polymethyl methacrylate and many other acrylates and copolymers of (meth)acrylates. Drawn films of PMMA/PLA blends are transparent and have high elongation.

Polycarbonate can be combined with PLA up to about a 50 wt. % composition of Polycarbonate. The compositions have high heat resistance, flame resistance and toughness and have applications, for example, in consumer electronics such as laptops. About 50 wt. % polycarbonate, the processing temperatures approach the degradation temperature of PLA.

Acrylonitrile butadiene styrene (ABS) can be blended with PLA although the polymers are not miscible. This combination is a less brittle material than PLA and provides a way to toughen PLA.

Poly(propylene carbonate) can be blended with PLA providing a biodegradable composite since both polymers are biodegradable.

PLA can also be blended with Poly(butylene succinate). Blends can impart thermal stability and impact strength to the PLA.

PEG, poly propylene glycol, poly(vinyl acetate), anhydrides (e.g., maleic anhydride) and fatty acid esters have been added as plasticizers and/or compatibilizers.

Blending can also be accomplished with the application of irradiation, including irradiation and quenching. For example, irradiation or irradiation and quenching, as described herein applied to biomass can be applied to the irradiation of PLA and PLA copolymers for any purpose, for example, before, after and/or during blending. This treatment can aid in the processing, for example, making the polymers more compatible and/or making/breaking bonds within the polymer and/or blended additive (e.g., polymer, plasticizer). For example, between about 0.1 Mrad and 150 Mrad followed by quenching of the radicals by the addition of fluids or gases (e.g., oxygen, nitrous oxide, ammonia, liquids), using pressure, heat, and/or the addition of radical scavengers. Quenching of biomass that has been irradiated is described in U.S. Pat. No. 8,083,906 to Medoff, the entire disclosure of which is incorporated herein by reference, and the equipment and processes describe therein can be applied to PLA and PLA derivatives. Irradiation and extruding or conveying of the PLA or PLA copolymers can also be utilized, for example, as described for the treatment of biomass in U.S. application Ser. No. 13/009,151 filed on May 2, 2011 the entire disclosure of which is incorporated herein by reference.

PLA Composites

PLA polymers, co-polymers and blends can be combined with synthetic and/or natural materials. For example, PLA and any PLA derivative (e.g., PLA copolymers, PLA blends, grated PLA, cross-linked PLA) can be combined with synthetic and natural fibers. For example, protein, starch, cellulose, plant fibers (e.g., abaca, leaf, skin, bark, kenaf fibers), inorganic fillers, flax, talc, glass, mica, saponite and carbon fibers. This can provide a material with, for example, improved mechanical properties (e.g., toughness, harness, strength) and improved barrier properties (e.g., lower permeability to water and/or gasses).

Nano composites can also be made by dispersing inorganic or organic nanoparticles into either a thermoplastic or thermoset polymer. Nanoparticles can be spherical, polyhedral, two dimensional nanofibers or disc-like nanoparticles. For example, colloidal or microcrystalline silica, alumina or metal oxides (e.g., $TiO_2$); carbon nanotubes; clay platelets.

Composites can be prepared similarly to polymer blends, for example, utilizing screw extrusion and/or injection molding. Irradiation as described herein can also be applied to the composites, during, after or before their formation. For example, irradiation of the polymer and combination with the synthetic and/or natural materials, or irradiation of the synthetic and/or natural materials and combination with the polymer, or irradiation of both the polymer and synthetic and/or natural material and then combining, or irradiating the composite after it has been combined, with or without further processing.

PLA with Plasticizers and Elastomers

In addition to the blends previously discussed, PLA and PLA derivatives can be combined with plasticizers.

For example, as described in *J. Appl. Polym. Sci.* 66: 1507-1513, 1997, PLA can be blended with monomeric and oligomeric plasticizers in order to enhance its flexibility and thereby overcome its inherent brittleness. Monomeric plasticizers, such as tributyl citrate, TbC, and diethyl bishydroxymethyl malonate, DBM, can drastically decreased the $T_g$ of PLA. Increasing the molecular weight of the plasticizers by synthesizing oligoesters and oligoesteramides can result in blends with $T_g$ depressions slightly smaller than with the monomeric plasticizers. The compatibility with PLA can be dependent on the molecular weight of the oligomers and on the presence of polar groups (e.g., amide groups, hydroxyl groups, ketones, esters) that can interact with the PLA chains. The materials can retain a high flexibility and morphological stability over long periods of time, for example, when formed into films.

Citrate esters can also be used as plasticizers with poly (lactic acid) (PLA) Films can be extruded, for example, using a single or twin-screw extruder with plasticizer contents (citrate esters or others described herein) of between about 1 and 40 wt. % (e.g., about 5-30 wt. %, about 5-25 wt. %, about 5-15 wt. %). Plasticizers such as citrate esters can be effective in reducing the glass transition temperature and improving the elongation at break. The plasticizing efficiency can be higher for the intermediate-molecular-weight plasticizers. The addition of plasticizers can modulate the enzymatic degradation of PLA. For example, lower-molecular-weight citrates can increase the enzymatic degradation rate of PLA and the higher-molecular-weight citrates can decreased the degradation rate as compared with that of unplasticized PLA.

Preparation of poly(lactic acid)/elastomer blends can also be prepared by melt blending technique, for example, as described in the *Journal of Elastomers and Plastics*, Jan. 3, 2013. PLA and biodegradable elastomer can be melt blended and molded in an injection molding machine. The melting temperature can decrease as the amount of elastomer increases. Additionally, the presence of elastomer can modulate the crystallinity of PLA, for example, increasing the crystallinity by between about 1 and 30% (e.g., between about 1 to 20%, between about 5 and 15%). The complex viscosity and storage modulus of PLA melt can decrease upon addition of elastomer. The elongation at break can increase as the content of elastomer increased while Young's modulus and tensile strength often decrease due to the addition of elastomer.

It has been observed that the cold crystallization temperature of the blends decreased as the weight fraction of elastomer increased as well as the onset temperature of cold crystallization also shifted to lower temperature. For example, as reported in the Journal of Polymer Research, February 2012, 19:9818. In non-isothermal crystallization experiments, the crystallinity of PLA increased with a decrease in the heating and cooling rate. The melt crystallization of poly(lactic acid) appeared in the low cooling rate (1, 5 and 7.5° C./min) The presence of small amounts of elastomer can also increase the crystallinity of poly (lactic acid). The DSC thermogram at ramp of 10° C./min showed the maximum crystallinity of poly(lactic acid) is 36.95% with 20 wt. % elastomer contents in blends. In isothermal crystallization, the cold crystallization rate increased with increasing crystallization temperature in the blends. The Avrami analysis showed that the cold crystallization was in two stages process and it was clearly seen at low temperature. The Avrami exponent (n) at first stage was varying from 1.59 to 2 which described a one-dimensional crystallization growth with homogeneous nucleation, whereas at second stage was varying from 2.09 to 2.71 which described the transitional mechanism to three dimensional crystallization growth with heterogeneous nucleation mechanism. The equilibrium melting point of poly(lactic acid) was also evaluated at 176° C.

Some examples of elastomers that can be combined with PLA include: Elastomer NPEL001, Polyurethane elastomers (5-10%), Functionalized polyolefin elastomers, Blendex® (e.g., 415, 360, 338), PARALOID™ KM 334, BTA 753, EXL 3691A, 2314, Ecoflex® Supersoft Silicone Bionolle® 3001, Pelleethane® 2102-75A, Kraton® FG 1901X, Hytrel® 3078, and mixtures of these. Mixtures with any other elastomer, for example, as described herein can also be used.

Some examples of plasticizers that can be combined with PLA include: Triacetin, glycerol triacetate, tributyl citrate, polyethylene glycol, GRINDSTED® SOFT-N-SAFE (acetic acid ester of monoglycerides) made from fully hydrogenated castor oil and combinations of these. Mixtures with any other plasticizers, for example, as described herein can also be used.

The main characteristic of elastomer materials is the high elongation and flexibility or elasticity of these materials, against its breaking or cracking.

Depending on the distribution and degree of the chemical bonds of the polymers, elastomeric materials can have properties or characteristics similar to thermosets or thermoplastics, so elastomeric materials can be classified into: Thermoset Elastomers (e.g., do not melt when heated) and Thermoplastic Elastomers (e.g., melt when heated). Some properties of elastomer materials: Cannot melt, before melting they pass into a gaseous state; swell in the presence of certain solvents; are generally insoluble; are flexible and elastic; lower creep resistance than the thermoplastic materials.

Examples of applications of elastomer materials described herein are: possible substitutes or replacements for natural rubber (e.g., material used in the manufacture of gaskets, shoe heels); possible substitutes or replacements for polyurethanes (e.g., for use in the textile industry for the manufacture of elastic clothing, for use as foam, and for use in making wheels); possible substitutes or replacements for polybutadiene (e.g., elastomer material used on the wheels or tires of vehicles); possible substitutes or replacements for neoprene (e.g., used for the manufacture of wetsuits, wire insulation, industrial belts); possible substitutes or replacements for silicone (e.g., pacifiers, medical prostheses, lubricants). In addition, the materials described herein can be used as substitutes for polyurethane and silicon adhesives.

Flavors, Fragrances and Colors

Any of the products and/or intermediates described herein, for example, hydroxyl acids, lactic acid, PLA, PLA derivatives (e.g., PLA copolymers, PLA composites, crosslinked PLA, grafted PLA, PLA blends or any other PLA containing material prepared as described herein) can also be combined with flavors, fragrances colors and/or mixtures of these. For example, any one or more of (optionally along with flavors, fragrances and/or colors) sugars, organic acids, fuels, polyols, such as sugar alcohols, biomass, fibers and composites, hydroxy-carboxylic acids, lactic acid, PLA, PLA derivatives can be combined with (e.g., formulated, mixed or reacted) or used to make other products. For example, one or more such product can be used to make soaps, detergents, candies, drinks (e.g., cola, wine, beer, liquors such as gin or vodka, sports drinks, coffees, teas), pharmaceuticals, adhesives, sheets (e.g., woven, none woven, filters, tissues) and/or composites (e.g., boards). For example, one or more such product can be combined with herbs, flowers, petals, spices, vitamins, potpourri, or candles. For example, the formulated, mixed or reacted combinations can have flavors/fragrances of grapefruit, orange, apple, raspberry, banana, lettuce, celery, cinnamon, vanilla, peppermint, mint, onion, garlic, pepper, saffron, ginger, milk, wine, beer, tea, lean beef, fish, clams, olive oil, coconut fat, pork fat, butter fat, beef bouillon, legume, potatoes, marmalade, ham, coffee and cheeses.

Flavors, fragrances and colors can be added in any amount, such as between about 0.01 wt. % to about 30 wt. %, e.g., between about 0.05 to about 10, between about 0.1 to about 5, or between about 0.25 wt. % to about 2.5 wt. %. These can be formulated, mixed and/or reacted (e.g., with any one of more product or intermediate described herein) by any means and in any order or sequence (e.g., agitated, mixed, emulsified, gelled, infused, heated, sonicated, and/or suspended). Fillers, binders, emulsifier, antioxidants can also be utilized, for example, protein gels, starches and silica.

The flavors, fragrances and colors can be natural and/or synthetic materials. These materials can be one or more of a compound, a composition or mixtures of these (e.g., a formulated or natural composition of several compounds). Optionally, the flavors, fragrances, antioxidants and colors can be derived biologically, for example, from a fermentation process (e.g., fermentation of saccharified materials as described herein). Alternatively, or additionally these flavors, fragrances and colors can be harvested from a whole organism (e.g., plant, fungus, animal, bacteria or yeast) or a part of an organism. The organism can be collected and or extracted to provide color, flavors, fragrances and/or antioxidant by any means including utilizing the methods, systems and equipment described herein, hot water extraction, chemical extraction (e.g., solvent or reactive extraction including acids and bases), mechanical extraction (e.g., pressing, comminuting, filtering), utilizing an enzyme, utilizing a bacteria such as to break down a starting material, and combinations of these methods. The compounds can be derived by a chemical reaction, for example, the combination of a sugar (e.g., as produced as described herein) with an amino acid (Maillard reaction). The flavor, fragrance, antioxidant and/or color can be an intermediate and or product produced by the methods, equipment or systems described herein, for example, and ester and a lignin derived product.

Some examples of flavor, fragrances or colors are polyphenols. Polyphenols are pigments responsible for the red, purple and blue colors of many fruits, vegetables, cereal grains, and flowers. Polyphenols also can have antioxidant properties and often have a bitter taste. The antioxidant properties make these important preservatives. On class of polyphenols are the flavonoids, such as Anthrocyanins, flavonols, flavan-3-ols, flavones, flavanones and flavanonols. Other phenolic compounds that can be used include phenolic acids and their esters, such as chlorogenic acid and polymeric tannins.

Inorganic compounds, minerals or organic compounds can be used, for example, titanium dioxide, cadmium yellow (e.g., CdS), cadmium orange (e.g., CdS with some Se), alizarin crimson (e.g., synthetic or non-synthetic rose madder), ultramarine (e.g., synthetic ultramarine, natural ultramarine, synthetic ultramarine violet), cobalt blue, cobalt yellow, cobalt green, viridian (e.g., hydrated chromium(III) oxide), chalcophyllite, conichalcite, cornubite, cornwallite and liroconite.

Some flavors and fragrances that can be utilized include ACALEA TBHQ, ACET C-6, ALLYL AMYL GLYCOLATE, ALPHA TERPINEOL, AMBRETTOLIDE, AMBRINOL 95, ANDRANE, APHERMATE, APPLELIDE, BACDANOL®, BERGAMAL, BETA IONONE EPDXIDE, BETA NAPHTHYL ISO-BUTYL ETHER, BICYCLONONALACTONE, BORNAFIX®, CANTHOXAL, CASHMERAN®, CASHMERAN® VELVET, CASSIFFIX®, CEDRAFIX, CEDRAMBER®, CEDRYL ACETATE, CELESTOLIDE, CINNAMALVA, CITRAL DIMETHYL ACETATE, CITROLATE™, CITRONELLOL 700, CITRONELLOL 950, CITRONELLOL COEUR, CITRONELLYL ACETATE, CITRONELLYL ACETATE PURE, CITRONELLYL FORMATE, CLARYCET, CLONAL, CONIFERAN, CONIFERAN PURE, CORTEX ALDEHYDE 50% PEOMOSA, CYCLABUTE, CYCLACET®, CYCLAPROP®, CYCLEMAX™, CYCLOHEXYL ETHYL ACETATE, DAMASCOL, DELTA DAMASCONE, DIHYDRO CYCLACET, DIHYDRO MYRCENOL, DIHYDRO TERPINEOL, DIHYDRO TERPINYL ACETATE, DIMETHYL CYCLORMOL, DIMETHYL OCTANOL PQ, DIMYRCETOL, DIOLA, DIPENTENE, DULCINYL® RECRYSTALLIZED, ETHYL-3-PHENYL GLYCIDATE, FLEURAMONE, FLEURANIL, FLORAL SUPER, FLORALOZONE, FLORIFFOL, FRAISTONE, FRUCTONE, GALAXOLIDE® 50, GALAXOLIDE® 50 BB, GALAXOLIDE® 50 IPM, GALAXOLIDE® UNDILUTED, GALBASCONE, GERALDEHYDE, GERANIOL 5020, GERANIOL 600 TYPE, GERANIOL 950, GERANIOL 980 (PURE), GERANIOL CFT COEUR, GERANIOL COEUR, GERANYL ACETATE COEUR, GERANYL ACETATE, PURE, GERANYL FORMATE, GRISALVA, GUAIYL ACETATE, HELIONAL™, HERBAC, HERBALIME™, HEXADECANOLIDE, HEXALON, HEXENYL SALICYLATE CIS 3-, HYACINTH BODY, HYACINTH BODY NO. 3, HYDRATROPIC ALDEHYDE.DMA, HYDROXYOL, INDOLAROME, INTRELEVEN ALDEHYDE, INTRELEVEN ALDEHYDE SPECIAL, IONONE ALPHA, IONONE BETA, ISO CYCLO CITRAL, ISO CYCLO GERANIOL, ISO E SUPER®, ISOBUTYL QUINOLINE, JASMAL, JESSEMAL®, KHARISMAL®, KHARISMAL® SUPER, KHUSINIL, KOAVONE®, KOHINOOL®, LIFFAROME™, LIMOXAL, LINDENOL™, LYRAL®, LYRAME SUPER, MANDARIN ALD 10% TRI ETH, CITR, MARITIMA, MCK CHINESE, MEIJIFF™, MELAFLEUR, MELOZONE, METHYL ANTHRANILATE, METHYL IONONE ALPHA EXTRA, METHYL IONONE GAMMA A, METHYL IONONE GAMMA COEUR, METHYL IONONE GAMMA PURE, METHYL LAVENDER KETONE, MONTAVERDI®, MUGUESIA, MUGUET ALDEHYDE 50, MUSK Z4, MYRAC ALDEHYDE, MYRCENYL ACETATE, NECTARATE™, NEROL 900, NERYL ACETATE, OCIMENE, OCTACETAL, ORANGE FLOWER ETHER, ORIVONE, ORRINIFF 25%, OXASPIRANE, OZOFLEUR, PAMPLEFLEUR®, PEOMOSA, PHENOXANOL®, PICONIA, PRECYCLEMONE B, PRENYL ACETATE, PRISMANTOL, RESEDA BODY, ROSALVA, ROSAMUSK, SANJINOL, SANTALIFF™, SYVERTAL, TERPINEOL, TERPINOLENE 20, TERPINOLENE 90 PQ, TERPINOLENE RECT., TERPINYL ACETATE, TERPINYL ACETATE JAX, TETRAHYDRO, MUGUOL®, TETRAHYDRO MYRCENOL, TETRAMERAN, TIMBERSILK™, TOBACAROL, TRIMOFIX® 0 TT, TRIPLAL®, TRISAMBER®, VANORIS, VERDOX™, VERDOX™ HC, VERTENEX®, VERTENEX® HC, VERTOFIX® COEUR, VERTOLIFF, VERTOLIFF ISO, VIOLIFF, VIVALDIE, ZENOLIDE, ABS INDIA 75 PCT MIGLYOL, ABS MOROCCO 50 PCT DPG, ABS MOROCCO 50 PCT TEC, ABSOLUTE FRENCH, ABSOLUTE INDIA, ABSOLUTE MD 50 PCT BB, ABSOLUTE MOROCCO, CONCENTRATE PG, TINCTURE 20 PCT, AMBERGRIS, AMBRETTE ABSOLUTE, AMBRETTE SEED OIL, ARMOISE OIL 70 PCT THUYONE, BASIL ABSOLUTE GRAND VERT, BASIL GRAND VERT ABS MD, BASIL OIL GRAND VERT, BASIL OIL VERVEINA, BASIL OIL VIETNAM, BAY OIL TERPENELESS, BEESWAX ABS N G, BEESWAX ABSOLUTE, BENZOIN RESINOID SIAM, BENZOIN RESINOID SIAM 50 PCT DPG, BENZOIN RESINOID SIAM 50 PCT PG, BENZOIN RESINOID SIAM 70.5 PCT TEC, BLACKCURRANT BUD ABS 65 PCT PG, BLACKCURRANT BUD ABS MD 37 PCT TEC, BLACKCURRANT BUD ABS MIGLYOL, BLACKCURRANT BUD ABSOLUTE BURGUNDY, BOIS DE ROSE OIL, BRAN ABSOLUTE, BRAN RESINOID, BROOM ABSOLUTE ITALY, CARDAMOM GUATEMALA CO2 EXTRACT, CARDAMOM OIL GUATEMALA, CARDAMOM OIL INDIA, CARROT HEART, CASSIE ABSOLUTE EGYPT, CASSIE ABSOLUTE MD 50 PCT IPM, CASTOREUM ABS 90 PCT TEC, CASTOREUM ABS C 50 PCT MIGLYOL, CASTOREUM ABSOLUTE, CASTOREUM RESINOID, CASTOREUM RESINOID 50 PCT DPG, CEDROL CEDRENE, *CEDRUS ATLANTICA* OIL REDIST, CHAMOMILE OIL ROMAN, CHAMOMILE OIL WILD, CHAMOMILE OIL WILD LOW LIMONENE, CINNAMON BARK OIL CEYLAN, CISTE ABSOLUTE, CISTE ABSOLUTE COLORLESS, CITRONELLA OIL ASIA IRON FREE, CIVET ABS 75 PCT PG, CIVET ABSOLUTE, CIVET TINCTURE 10 PCT, CLARY SAGE ABS FRENCH DECOL, CLARY SAGE ABSOLUTE FRENCH, CLARY SAGE C'LESS 50 PCT PG, CLARY SAGE OIL FRENCH, COPAIBA BALSAM, COPAIBA BALSAM OIL, CORIANDER SEED OIL, CYPRESS OIL, CYPRESS OIL ORGANIC, DAVANA OIL, GALBANOL, *GALBANUM* ABSOLUTE COLORLESS, *GALBANUM* OIL, *GALBANUM* RESINOID, *GALBANUM* RESINOID 50 PCT DPG, *GALBANUM* RESINOID HERCOLYN BHT, GALBANUM RESINOID TEC BHT, GENTIANE ABSOLUTE MD 20 PCT BB, GENTIANE CONCRETE, GERANIUM ABS EGYPT MD, GERANIUM ABSOLUTE EGYPT, GERANIUM OIL CHINA, GERANIUM OIL EGYPT, GINGER OIL 624, GINGER OIL RECTIFIED SOLUBLE, GUAIACWOOD HEART, HAY ABS MD 50 PCT BB, HAY ABSOLUTE, HAY ABSOLUTE MD 50 PCT TEC, HEALINGWOOD, HYSSOP OIL ORGANIC, IMMORTELLE ABS YUGO MD 50 PCT TEC, IMMORTELLE ABSOLUTE SPAIN, IMMORTELLE ABSOLUTE YUGO, JASMIN ABS INDIA MD, JASMIN ABSOLUTE EGYPT, JASMIN ABSOLUTE INDIA, ASMIN ABSOLUTE MOROCCO, JASMIN ABSOLUTE SAMBAC, JONQUILLE ABS MD 20 PCT BB, JONQUILLE ABSOLUTE France, JUNIPER BERRY OIL FLG, JUNIPER BERRY OIL RECTIFIED SOLUBLE, LABDANUM RESINOID 50 PCT TEC, LABDANUM RESINOID BB, LABDANUM RESINOID MD, LABDANUM RESINOID MD 50 PCT BB, LAVANDIN ABSOLUTE H, LAVANDIN ABSOLUTE MD, LAVANDIN OIL ABRIAL ORGANIC, LAVANDIN OIL GROSSO ORGANIC, LAVANDIN OIL SUPER, LAVENDER ABSOLUTE H, LAVENDER ABSOLUTE MD, LAVENDER OIL COUMARIN FREE, LAVENDER OIL COUMARIN FREE ORGANIC, LAVENDER OIL MAILLETTE ORGANIC, LAVENDER OIL MT, MACE ABSOLUTE BB, *MAGNOLIA* FLOWER OIL LOW METHYL EUGENOL, *MAGNOLIA* FLOWER OIL, *MAGNOLIA* FLOWER OIL MD, *MAGNOLIA* LEAF OIL, MANDARIN OIL MD, MANDARIN OIL MD BHT, MATE ABSOLUTE BB, MOSS TREE ABSOLUTE MD TEX IFRA 43, MOSS-OAK ABS MD TEC IFRA 43, MOSS-OAK ABSOLUTE IFRA 43, MOSS-TREE ABSOLUTE MD IPM IFRA 43, MYRRH RESINOID BB, MYRRH RESINOID MD, MYRRH RESINOID TEC, MYRTLE OIL IRON FREE, MYRTLE OIL TUNISIA RECTIFIED, NARCISSE ABS MD 20 PCT BB, NARCISSE ABSOLUTE FRENCH, NEROLI OIL TUNISIA, NUTMEG OIL TERPENELESS, OEILLET ABSOLUTE, OLIBANUM RESINOID, OLIBANUM RESINOID BB, OLIBANUM RESINOID DPG, OLIBANUM RESINOID EXTRA 50 PCT DPG, OLIBANUM RESINOID MD, OLIBANUM RESINOID MD 50 PCT DPG, OLIBANUM RESINOID TEC, OPOPONAX RESINOID TEC, ORANGE BIGARADE OIL MD BHT, ORANGE BIGARADE OIL MD SCFC, ORANGE FLOWER ABSOLUTE TUNISIA, ORANGE FLOWER WATER ABSOLUTE TUNISIA, ORANGE LEAF ABSOLUTE, ORANGE LEAF WATER ABSOLUTE TUNISIA, ORRIS ABSOLUTE ITALY, ORRIS CONCRETE 15 PCT IRONE, ORRIS CONCRETE 8 PCT IRONE, ORRIS NATURAL 15 PCT IRONE 4095C, ORRIS NATURAL 8 PCT IRONE 2942C, ORRIS RESINOID, OSMANTHUS ABSOLUTE, OSMANTHUS ABSOLUTE MD 50 PCT BB, PATCHOULI HEART N° 3, PATCHOULI OIL INDONESIA, PATCHOULI OIL INDONESIA IRON FREE, PATCHOULI OIL INDONESIA MD, PATCHOULI OIL REDIST, PENNYROYAL HEART, PEPPERMINT ABSOLUTE MD, PETITGRAIN BIGARADE OIL TUNISIA, PETITGRAIN CITRONNIER OIL, PETITGRAIN OIL PARAGUAY TERPENELESS, PETITGRAIN OIL TERPENELESS STAB, PIMENTO BERRY OIL, PIMENTO LEAF OIL, RHODINOL EX GERANIUM CHINA, ROSE ABS BULGARIAN LOW METHYL EUGENOL, ROSE ABS MOROCCO LOW METHYL EUGENOL, ROSE ABS TURKISH LOW METHYL EUGENOL, ROSE ABSOLUTE, ROSE ABSOLUTE BULGARIAN, ROSE ABSOLUTE *DAMASCENA*, ROSE ABSOLUTE MD, ROSE ABSOLUTE MOROCCO, ROSE ABSOLUTE TURKISH, ROSE OIL BULGARIAN, ROSE OIL *DAMASCENA* LOW METHYL EUGENOL, ROSE OIL TURKISH, ROSEMARY OIL CAMPHOR ORGANIC, ROSEMARY OIL TUNISIA, SANDALWOOD OIL INDIA, SANDALWOOD OIL INDIA RECTIFIED, SANTALOL, *SCHINUS MOLLE* OIL, ST JOHN BREAD TINCTURE 10 PCT, *STYRAX* RESINOID, *STYRAX* RESINOID, TAGETE OIL, TEA TREE HEART, TONKA BEAN ABS 50 PCT SOLVENTS, TONKA BEAN ABSOLUTE, TUBEROSE ABSOLUTE INDIA, VETIVER HEART EXTRA, VETIVER OIL HAITI, VETIVER OIL HAITI MD, VETIVER OIL JAVA, VETIVER OIL JAVA MD, VIOLET LEAF ABSOLUTE EGYPT, VIOLET LEAF ABSOLUTE EGYPT DECOL, VIOLET LEAF ABSOLUTE FRENCH, VIOLET LEAF ABSOLUTE MD 50 PCT BB, WORMWOOD OIL TERPENELESS, YLANG EXTRA OIL, YLANG III OIL and combinations of these.

The colorants can be among those listed in the Color Index International by the Society of Dyers and Colourists. Colorants include dyes and pigments and include those commonly used for coloring textiles, paints, inks and inkjet inks. Some colorants that can be utilized include carotenoids, arylide yellows, diarylide yellows, B-naphthols, naphthols, benzimidazolones, disazo condensation pigments, pyrazolones, nickel azo yellow, phthalocyanines, quinacridones, perylenes and perinones, isoindolinone and isoindoline pigments, triarylcarbonium pigments, diketopyrrolo-pyrrole pigments, thioindigoids. Cartenoids include e.g., alpha-carotene, beta-carotene, gamma-carotene, lycopene, lutein and astaxanthin Annatto extract, Dehydrated beets (beet powder), Canthaxanthin, Caramel, Apo-8'-carotenal, Cochineal extract, Carmine, Sodium copper chlorophyllin, Toasted partially defatted cooked cottonseed flour, Ferrous gluconate, Ferrous lactate, Grape color extract, Grape skin extract (enocianina), Carrot oil, Paprika, Paprika oleoresin, Mica-based pearlescent pigments, Riboflavin, Saffron, Titanium dioxide, carbon black, self-dispersed carbon, Tomato lycopene extract; tomato lycopene concentrate, Turmeric, Turmeric oleoresin, FD&C Blue No. 1, FD&C Blue No. 2, FD&C Green No. 3, Orange B, Citrus Red No. 2, FD&C Red No. 3, FD&C Red No. 40, FD&C Yellow No. 5, FD&C Yellow No. 6, Alumina (dried aluminum hydroxide), Calcium carbonate, Potassium sodium copper chlorophyllin (chlorophyllin-copper complex), Dihydroxyacetone, Bismuth oxychloride, Ferric ammonium ferrocyanide, Ferric ferrocyanide, Chromium hydroxide green, Chromium oxide greens, Guanine, Pyrophyllite, Talc, Aluminum powder, Bronze powder, Copper powder, Zinc oxide, D&C Blue No. 4, D&C Green No. 5, D&C Green No. 6, D&C Green No. 8, D&C Orange No. 4, D&C Orange No. 5, D&C Orange No. 10, D&C Orange No. 11, FD&C Red No. 4, D&C Red No. 6, D&C Red No. 7, D&C Red No. 17, D&C Red No. 21, D&C Red No. 22, D&C Red No. 27, D&C Red No. 28, D&C Red No. 30, D&C Red No. 31, D&C Red No. 33, D&C Red No. 34, D&C Red No. 36, D&C Red No. 39, D&C Violet No. 2, D&C Yellow No. 7, Ext. D&C Yellow No. 7, D&C Yellow No. 8, D&C Yellow No. 10, D&C Yellow No. 11, D&C Black No. 2, D&C Black No. 3 (3), D&C Brown No. 1, Ext. D&C, Chromium-cobalt-aluminum oxide, Ferric ammonium citrate, Pyrogallol, Logwood extract, 1,4-Bis[(2-hydroxy-ethyl)amino]-9,10-anthracenedione bis(2-propenoic)ester copolymers, 1,4-Bis[(2-methylphenyl)amino]-9,10-anthracenedione, 1,4-Bis[4-(2-methacryloxyethyl) phenylamino]anthraquinone copolymers, Carbazole violet, Chlorophyllin-copper complex, Chromium-cobalt-aluminum oxide, C.I. Vat Orange 1,2-[[2,5-Diethoxy-4-[(4-methylphenyl)thiol]phenyl]azo]-1,3,5-benzenetriol, 16,23-Dihydrodinaphtho[2,3-a:2',3'-i]naphth[2',3': 6,7]indolo[2,3-c]carbazole-5,10,15,17,22,24-hexone, N,N'-(9,10-Dihydro-9,10-dioxo-1,5-anthracenediyl) bisbenzamide, 7,16-Dichloro-6,15-dihydro-5,9,14,18-anthrazinetetrone, 16,17-Dimethoxydinaphtho (1,2,3-cd:3',2', 1'-1m) perylene-5,10-dione, Poly(hydroxyethyl methacrylate)-dye copolymers (3), Reactive Black 5, Reactive Blue 21, Reactive Orange 78, Reactive Yellow 15, Reactive Blue No. 19, Reactive Blue No. 4, C.I. Reactive Red 11, C.I. Reactive Yellow 86, C.I. Reactive Blue 163, C.I. Reactive Red 180, 4-[(2,4-dimethylphenyl)azo]-2,4-dihydro-5-methyl-2-phenyl-3H-pyrazol-3-one (solvent Yellow 18), 6-Ethoxy-2-(6-ethoxy-3-oxobenzo[b]thien-2(3H)-ylidene) benzo[b]thiophen-3(2H)-one, Phthalocyanine green, Vinyl alcohol/methyl methacrylate-dye reaction products, C.I. Reactive Red 180, C.I. Reactive Black 5, C.I. Reactive Orange 78, C.I. Reactive Yellow 15, C.I. Reactive Blue 21, Disodium 1-amino-4-[[4-[(2-bromo-1-oxoallyl)amino]-2-sulphonatophenyl]amino]-9,10-dihydro-9,10-dioxoanthracene-2-sulphonate (Reactive Blue 69), D&C Blue No. 9, [Phthalocyaninato(2-)] copper and mixtures of these.

For example, a fragrance, e.g., natural wood fragrance, can be compounded into the resin used to make the composite. In some implementations, the fragrance is compounded directly into the resin as an oil. For example, the oil can be compounded into the resin using a roll mill, e.g., a Banbury® mixer or an extruder, e.g., a twin-screw extruder with counter-rotating screws. An example of a Banbury® mixer is the F-Series Banbury® mixer, manufactured by Farrel. An example of a twin-screw extruder is the WP ZSK 50 MEGACOMPOUNDER™, manufactured by Coperion, Stuttgart, Germany. After compounding, the scented resin can be added to the fibrous material and extruded or molded. Alternatively, master batches of fragrance-filled resins are available commercially from International Flavors and Fragrances, under the trade name POLYIFF™. In some embodiments, the amount of fragrance in the composite is between about 0.005% by weight and about 10% by weight, e.g., between about 0.1% and about 5% or 0.25% and about 2.5%. Other natural wood fragrances include evergreen or redwood. Other fragrances include peppermint, cherry, strawberry, peach, lime, spearmint, cinnamon, anise, basil, bergamot, black pepper, camphor, chamomile, citronella, eucalyptus, pine, fir, geranium, ginger, grapefruit, jasmine, juniper berry, lavender, lemon, mandarin, marjoram, musk, myrrh, orange, patchouli, rose, rosemary, sage, sandalwood, tea tree, thyme, wintergreen, ylang ylang, vanilla, new car or mixtures of these fragrances. In some embodiments, the amount of fragrance in the fibrous material-fragrance combination is between about 0.005% by weight and about 20% by weight, e.g., between about 0.1% and about 5% or 0.25% and about 2.5%. Even other fragrances and methods are described U.S. Pat. No. 8,074,910 issued Dec. 13, 2011, the entire disclosure of which incorporated herein by reference.

Uses of PLA and PLA Copolymers

Some uses of PLA and PLA containing materials include: personal care items (e.g., tissues, towels, diapers), green packaging, garden (compostable pots), consumer electronics (e.g., laptop and mobile phone casings), appliances, food packaging, disposable packaging (e.g., food containers and drink bottles), garbage bags (e.g., waste compostable bags), mulch films, controlled release matrices and containers (e.g., for fertilizers, pesticides, herbicides, nutrients, pharmaceuticals, flavoring agents, foods), shopping bags, general purpose film, high heat film, heat seal layer, surface coating, disposable tableware (e.g., plates, cups, forks, knives, spoons, sporks, bowls), automotive parts (e.g., panels, fabrics, under hood covers), carpet fibers, clothing fibers (e.g., for garments, sportswear, footwear), biomedical applications (e.g., surgical sutures, implants, scaffolding, drug delivery systems, dialysis equipment) and engineering plastics.

Other uses/industrial sectors that can benefit from the use of PLA and PLA derivatives (e.g., elastomers) include IT and software, electronics, geoscience (e.g., oil and gas), engineering, aerospace (e.g., arm rests, seats, panels), telecommunications (e.g., headsets), chemical manufacturing, transportation such as automotive (e.g., dashboards, panels, tires, wheels), materials and steel, consumer packaged goods, wires and cables.

Other Advantages of PLA and PLA Copolymers

PLA is bio-based and can be composted, recycled, used as a fuel (incinerated). Some of the degradation reactions include thermal degradation, hydrolytic degradation and biotic degradations.

PLA can be thermally degraded. For example, at high temperatures (e.g., between about 200-300° C., about 230-260° C.). The reactions involved in the thermal degradation of PLA can follow different mechanisms such as thermo hydrolysis, zipper-like depolymerization (e.g., in the presence of residual catalysts), thermo-oxidative degradation. Transesterification reactions can also operate on the polymer causing bond breaking and/or bond making.

PLA also can undergo hydrolytic degradation. Hydrolytic degradation includes chain scission producing shorter polymers, oligomers and eventually the monomer lactic acid can be released. Hydrolysis can be associated with thermal and biotic degradation. The process can be effected by various parameters such as the PLA structure, its molecular weight and distribution, its morphology (e.g., crystallinity), the shape of the sample (e.g., isolated thin samples or comminuted samples can degrade faster), the thermal and mechanical history (e.g., processing) and the hydrolysis conditions (e.g., temperature, agitation, comminution). The hydrolysis of PLA starts with a water uptake phase, followed by hydrolytic splitting of the ester bonds. The amorphous parts of the polyesters can be hydrolyzed faster than the crystalline regions because of the higher water uptake and mobility of chain segments in these regions. In a second stage, the crystalline regions of PLA are hydrolyzed.

PLA can also undergo biotic degradation. This degradation can occur for example, in a mammalian body, and has useful implications for ° degradable stitching and can have detrimental implications to other surgical implants. Enzymes, such as proteinase K and pronase can be utilized.

During composting, PLA can go through several degradation stages. For example, an initial stage can occur due to exposure to moisture wherein the degradation is abiotic and the PLA degrades by hydrolysis. This stage can be accelerated by the presence of acids and bases and elevated temperatures. The first stage can lead to embrittlement of the polymer which can facilitate the diffusion of PLA out of the bulk polymers. The oligomers can then be attacked by micro-organisms. Organisms can degrade the oligomers and lactic acid, leading to $CO_2$ and water. Time for this degradation is on the order of about one to a few years depending on the factors previously mentioned. The degradation time is several orders of magnitude faster than typical petroleum based plastic such as polyethylene (e.g., on the order of hundreds of years).

PLA can also be recycled. For example, the PLA can be hydrolyzed to lactide acid, purified and re-polymerized. Unlike other recyclable plastics such as PET and HDPE, PLA does not need to be down-graded to make a product of diminished value (e.g., from a bottle to decking or carpet). PLA can be in theory recycled indefinitely. Optionally, PLA can be re-used and downgraded for several generations and then converted to PLA and re-polymerized.

PLA can also be used as a fuel, for example, for energy production. PLA can have high heat content e.g., up to about 8400 BTU. Incineration of pure PLA only releases carbon dioxide and water. Combinations with other ingredients typically amount to less than 1 ppm of non PLA residuals (e.g., ash). Thus the combustion of PLA is cleaner than other renewable fuels, e.g. wood.

PLA can have high gloss, high transparency, high clarity, high stiffness, can be UV stable, non-allergenic, high flavor and aroma barrier properties, easy to blend, easy to mold, easy to shape, easy to emboss, easy to print on, lightweight, compostable.

PLA can also be printed on. For example, by lithographic, ink-jet printing, laser printing, fixed-type printing, roller printing. Some PLA can also be written on, for example, using a pen.

Processing as described herein can also include irradiation. For example, irradiation with between about 1 and 150 Mrad radiation (e.g., for example, any range as described herein) can improve the compostability and recyclability of PLA and PLA containing materials.

Radiation Treatment

The feedstock (e.g., cellulosic, lignocellulosic, PLA, PLA derivatives and combinations of these) can be treated with electron bombardment to modify its structure, for example, to reduce its recalcitrance or cross link the structures. Such treatment can, for example, reduce the average molecular weight of the feedstock, change the crystalline structure of the feedstock, and/or increase the surface area and/or porosity of the feedstock. Alternatively this treatment can produce radicals that can be sites for cross-linking, grafting and/or functionalization.

Electron bombardment via an electron beam is generally preferred, because it provides very high throughput. Accelerators used to accelerate the particles can be electrostatic DC, electrodynamic DC, RF linear, magnetic induction linear or continuous wave. For example, cyclotron type accelerators are available from IBA, Belgium, such as the RHODOTRON™ system, while DC type accelerators are available from RDI, now IBA Industrial, such as the DYNAMITRON®. Ions and ion accelerators are discussed in Introductory Nuclear Physics, Kenneth S. Krane, John Wiley & Sons, Inc. (1988), Krsto Prelec, FIZIKA B 6 (1997) 4, 177-206, Chu, William T., "Overview of Light-Ion Beam Therapy", Columbus-Ohio, ICRU-IAEA Meeting, 18-20 Mar. 2006, Iwata, Y. et al., "Alternating-Phase-Focused IH-DTL for Heavy-Ion Medical Accelerators", Proceedings of EPAC 2006, Edinburgh, Scotland, and Leitner, C. M. et al., "Status of the Superconducting ECR Ion Source Venus", Proceedings of EPAC 2000, Vienna, Austria.

Electron bombardment may be performed using an electron beam device that has a nominal energy of less than 10 MeV, e.g., less than 7 MeV, less than 5 MeV, or less than 2 MeV, e.g., from about 0.5 to 1.5 MeV, from about 0.8 to 1.8 MeV, or from about 0.7 to 1 MeV. In some implementations the nominal energy is about 500 to 800 keV.

The electron beam may have a relatively high total beam power (the combined beam power of all accelerating heads, or, if multiple accelerators are used, of all accelerators and all heads), e.g., at least 25 kW, e.g., at least 30, 40, 50, 60, 65, 70, 80, 100, 125, or 150, 250, 300 kW. In some cases, the power is even as high as 500 kW, 750 kW, or even 1000 kW or more. In some cases the electron beam has a beam power of 1200 kW or more, e.g., 1400, 1600, 1800, or even 3000 kW. The electron beam may have a total beam power of 25 to 3000 kW. Alternatively, the electron beam may have a total beam power of 75 to 1500 kW. Optionally, the electron beam may have a total beam power of 100 to 1000 kW. Alternatively, the electron beam may have a total beam power of 100 to 400 kW.

This high total beam power is usually achieved by utilizing multiple accelerating heads. For example, the electron beam device may include two, four, or more accelerating heads. The use of multiple heads, each of which has a relatively low beam power, prevents excessive temperature rise in the material, thereby preventing burning of the material, and also increases the uniformity of the dose through the thickness of the layer of material.

It is generally preferred that the bed of feedstock material has a relatively uniform thickness. In some embodiments the thickness is less than about 1 inch (e.g., less than about 0.75 inches, less than about 0.5 inches, less than about 0.25 inches, less than about 0.1 inches, between about 0.1 and 1 inch, between about 0.2 and 0.3 inches).

In some implementations, it is desirable to cool the material during and between dosing the material with electron bombardment. For example, the material can be cooled while it is conveyed, for example, by a screw extruder, vibratory conveyor or other conveying equipment. For example, cooling while conveying is described International App. No. PCT/US2014/021609 filed Mar. 7, 2014 and International App. No. PCT/US2014/021632 filed Mar. 7, 2014, the entire descriptions of which are herein incorporated by reference.

To reduce the energy required by the recalcitrance-reducing process, it is desirable to treat the material as quickly as possible. In general, the treatment be performed at a dose rate of greater than about 0.25 Mrad per second, e.g., greater than about 0.5, 0.75, 1, 1.5, 2, 5, 7, 10, 12, 15, or even greater than about 20 Mrad per second, e.g., about 0.25 to 30 Mrad per second. Alternately, the treatment is performed at a dose rate of 0.5 to 20 Mrad per second. Optionally, the treatment is performed at a dose rate of 0.75 to 15 Mrad per second. Alternately, the treatment is performed at a dose rate of 1 to 5 Mrad per second. Optionally, the treatment is performed at a dose rate of 1-3 Mrad per second or alternatively 1-2 Mrad per second. Higher dose rates allow a higher throughput for a target (e.g., the desired) dose. Higher dose rates generally require higher line speeds, to avoid thermal decomposition of the material. In one implementation, the accelerator is set for 3 MeV, 50 mA beam current, and the line speed is 24 feet/minute, for a sample thickness of about 20 mm (e.g., comminuted corn cob material with a bulk density of 0.5 g/cm$^3$).

In some embodiments, electron bombardment is performed until the material receives a total dose of at least 0.1 Mrad, 0.25 Mrad, 1 Mrad, 5 Mrad, e.g., at least 10, 20, 30 or at least 40 Mrad. In some embodiments, the treatment is performed until the material receives a dose of from about 10 Mrad to about 50 Mrad, e.g., from about 20 Mrad to about 40 Mrad, or from about 25 Mrad to about 30 Mrad. In some implementations, a total dose of 25 to 35 Mrad is preferred, applied ideally over a couple of seconds, e.g., at 5 Mrad/pass with each pass being applied for about one second. Applying a dose of greater than 7 to 8 Mrad/pass can in some cases cause thermal degradation of the feedstock material. Cooling can be applied before, after, or during irradiation. For example, the cooling methods, systems and equipment as described in the following applications can be utilized: International App. No. PCT/US2014/021609 filed Mar. 7, 2014, and International App. No. PCT/US2013/064320 filed Oct. 10, 2013, the entire disclosures of which are herein incorporated by reference.

Using multiple heads as discussed above, the material can be treated in multiple passes, for example, two passes at 10 to 20 Mrad/pass, e.g., 12 to 18 Mrad/pass, separated by a few seconds of cool-down, or three passes of 7 to 12 Mrad/pass, e.g., 5 to 20 Mrad/pass, 10 to 40 Mrad/pass, 9 to 11 Mrad/pass. As discussed herein, treating the material with several relatively low doses, rather than one high dose, tends to prevent overheating of the material and also increases dose uniformity through the thickness of the material. In some implementations, the material is stirred or otherwise mixed during or after each pass and then smoothed into a uniform layer again before the next pass, to further enhance treatment uniformity.

In some embodiments, electrons are accelerated to, for example, a speed of greater than 75 percent of the speed of light, e.g., greater than 85, 90, 95, or 99 percent of the speed of light.

In some embodiments, any processing described herein occurs on feedstock material that remains dry as acquired or that has been dried, e.g., using heat and/or reduced pressure. For example, in some embodiments, the cellulosic and/or lignocellulosic material has less than about 25 wt. % retained water, measured at 25° C. and at fifty percent relative humidity (e.g., less than about 20 wt. %, less than about 15 wt. %, less than about 14 wt. %, less than about 13 wt. %, less than about 12 wt. %, less than about 10 wt. %, less than about 9 wt. %, less than about 8 wt. %, less than about 7 wt. %, less than about 6 wt. %, less than about 5 wt. %, less than about 4 wt. %, less than about 3 wt. %, less than about 2 wt. %, less than about 1 wt. %, less than about 0.5 wt. %, less than about 15 wt. %.

In some embodiments, two or more electron sources are used, such as two or more ionizing sources. For example, samples can be treated, in any order, with a beam of electrons, followed by gamma radiation and UV light having wavelengths from about 100 nm to about 280 nm. In some embodiments, samples are treated with three ionizing radiation sources, such as a beam of electrons, gamma radiation, and energetic UV light. The biomass is conveyed through the treatment zone where it can be bombarded with electrons.

It may be advantageous to repeat the treatment to more thoroughly reduce the recalcitrance of the biomass and/or further modify the biomass. In particular, the process parameters can be adjusted after a first (e.g., second, third, fourth or more) pass depending on the recalcitrance of the material. In some embodiments, a conveyor can be used which includes a circular system where the biomass is conveyed multiple times through the various processes described above. In some other embodiments, multiple treatment devices (e.g., electron beam generators) are used to treat the biomass multiple (e.g., 2, 3, 4 or more) times. In yet other embodiments, a single electron beam generator may be the source of multiple beams (e.g., 2, 3, 4 or more beams) that can be used for treatment of the biomass.

The effectiveness in changing the molecular/supermolecular structure and/or reducing the recalcitrance of the carbohydrate-containing biomass depends on the electron energy used and the dose applied, while exposure time depends on the power and dose. In some embodiments, the dose rate and total are adjusted so as not to destroy (e.g., char or burn) the biomass material. For example, the carbohydrates should not be damaged in the processing so that they can be released from the biomass intact, e.g. as monomeric sugars.

In some embodiments, the treatment (with any electron source or a combination of sources) is performed until the material receives a dose of at least about 0.05 Mrad, e.g., at least about 0.1, 0.25, 0.5, 0.75, 1.0, 2.5, 5.0, 7.5, 10.0, 15, 20, 25, 30, 40, 50, 60, 70, 80, 90, 100, 125, 150, 175, or 200 Mrad. In some embodiments, the treatment is performed until the material receives a dose of between 0.1-100 Mrad, 1-200, 5-200, 10-200, 5-150, 50-150 Mrad, 5-100, 5-50, 5-40, 10-50, 10-75, 15-50, 20-35 Mrad.

Radiation Opaque Materials

The invention can include processing the material in a vault and/or bunker that is constructed using radiation opaque materials. In some implementations, the radiation opaque materials are selected to be capable of shielding the components from X-rays with high energy (short wavelength), which can penetrate many materials. One important factor in designing a radiation shielding enclosure is the attenuation length of the materials used, which will determine the required thickness for a particular material, blend of materials, or layered structure. The attenuation length is the penetration distance at which the radiation is reduced to approximately 1/e (e=Euler's number) times that of the incident radiation. Although virtually all materials are radiation opaque if thick enough, materials containing a high compositional percentage (e.g., density) of elements that have a high Z value (atomic number) have a shorter radiation attenuation length and thus, if such materials are used, a thinner, lighter shielding can be provided. Examples of high Z value materials that are used in radiation shielding are tantalum and lead. Another important parameter in radiation shielding is the halving distance, which is the thickness of a particular material that will reduce gamma ray intensity by 50%. As an example for X-ray radiation with an energy of 0.1 MeV the halving thickness is about 15.1 mm for concrete and about 0.27 mm for lead, while with an X-ray energy of 1 MeV the halving thickness for concrete is about 44.45 mm and for lead is about 7.9 mm Radiation opaque materials can be materials that are thick or thin so long as they can reduce the radiation that passes through to the other side. Thus, if it is desired that a particular enclosure have a low wall thickness, e.g., for light weight or due to size constraints, the material chosen should have a sufficient Z value and/or attenuation length so that its halving length is less than or equal to the desired wall thickness of the enclosure.

In some cases, the radiation opaque material may be a layered material, for example, having a layer of a higher Z value material, to provide good shielding, and a layer of a lower Z value material to provide other properties (e.g., structural integrity, impact resistance, etc.). In some cases, the layered material may be a "graded-Z" laminate, e.g., including a laminate in which the layers provide a gradient from high-Z through successively lower-Z elements. In some cases the radiation opaque materials can be interlocking blocks, for example, lead and/or concrete blocks can be supplied by NELCO Worldwide (Burlington, Mass.), and reconfigurable vaults can be utilized as described in International App. No. PCT/US2014/021629 filed on Mar. 7, 2014 the entire disclosure of which is herein incorporated by reference.

A radiation opaque material can reduce the radiation passing through a structure (e.g., a wall, door, ceiling, enclosure, a series of these or combinations of these) formed of the material by about at least about 10%, (e.g., at least about 20%, at least about 30%, at least about 40%, at least about 50%, at least about 60%, at least about 70%, at least about 80%, at least about 90%, at least about 95%, at least about 96%, at least about 97%, at least about 98%, at least about 99%, at least about 99.9%, at least about 99.99%, at least about 99.999%) as compared to the incident radiation. Therefore, an enclosure made of a radiation opaque material can reduce the exposure of equipment/system/components by the same amount. Radiation opaque materials can include stainless steel, metals with Z values above 25 (e.g., lead, iron), concrete, dirt, sand and combinations thereof. Radiation opaque materials can include a barrier in the direction of the incident radiation of at least about 1 mm (e.g., 5 mm, 10 mm, 5 cm, 10 cm, 100 cm, 1 m, 10 m).

Electron Sources

Electrons interact via Coulomb scattering and bremsstrahlung radiation produced by changes in the velocity of electrons. Electrons may be produced by radioactive nuclei that undergo beta decay, such as isotopes of iodine, cesium, technetium, and iridium. Alternatively, an electron gun can be used as an electron source via thermionic emission and accelerated through an accelerating potential. An electron gun generates electrons, accelerates them through a large potential (e.g., greater than about 500 thousand, greater than about 1 million, greater than about 2 million, greater than about 5 million, greater than about 6 million, greater than about 7 million, greater than about 8 million, greater than about 9 million, or even greater than 10 million volts) and then scans them magnetically in the x-y plane, where the electrons are initially accelerated in the z direction down the tube and extracted through a foil window. Scanning the electron beam is useful for increasing the irradiation surface when irradiating materials, e.g., a biomass, that is conveyed through the scanned beam. Scanning the electron beam also distributes the thermal load homogenously on the window and helps reduce the foil window rupture due to local heating by the electron beam. Window foil rupture is a cause of significant down-time due to subsequent necessary repairs and re-starting the electron gun.

Various other irradiating devices may be used in the methods disclosed herein, including field ionization sources, electrostatic ion separators, field ionization generators, thermionic emission sources, microwave discharge ion sources, recirculating or static accelerators, dynamic linear accelerators, van de Graaff accelerators, and folded tandem accelerators. Such devices are disclosed, for example, in U.S. Pat. No. 7,931,784 to Medoff, the complete disclosure of which is incorporated herein by reference.

A beam of electrons can be used as the radiation source. A beam of electrons has the advantages of high dose rates (e.g., 1, 5, or even 10 Mrad per second), high throughput, less containment, and less confinement equipment. Electron beams can also have high electrical efficiency (e.g., 80%), allowing for lower energy usage relative to other radiation methods, which can translate into a lower cost of operation and lower greenhouse gas emissions corresponding to the smaller amount of energy used. Electron beams can be generated, e.g., by electrostatic generators, cascade generators, transformer generators, low energy accelerators with a scanning system, low energy accelerators with a linear cathode, linear accelerators, and pulsed accelerators.

Electrons can also be more efficient at causing changes in the molecular structure of carbohydrate-containing materials, for example, by the mechanism of chain scission. In addition, electrons having energies of 0.5-10 MeV can penetrate low density materials, such as the biomass materials described herein, e.g., materials having a bulk density of less than 0.5 g/cm$^3$, and a depth of 0.3-10 cm. Electrons as an ionizing radiation source can be useful, e.g., for relatively thin piles, layers or beds of materials, e.g., less than about 0.5 inch, e.g., less than about 0.4 inch, 0.3 inch, 0.25 inch, or less than about 0.1 inch. In some embodiments, the energy of each electron of the electron beam is from about 0.3 MeV to about 2.0 MeV (million electron volts), e.g., from about 0.5 MeV to about 1.5 MeV, or from about 0.7 MeV to about 1.25 MeV. Methods of irradiating materials are discussed in U.S. Pat. App. Pub. 2012/0100577 A1, filed Oct. 18, 2011, the entire disclosure of which is herein incorporated by reference.

Electron beam irradiation devices may be procured commercially from Ion Beam Applications, Louvain-la-Neuve, Belgium or the Titan Corporation, San Diego, Calif. Typical electron energies can be 0.5 MeV, 1 MeV, 2 MeV, 4.5 MeV, 7.5 MeV, or 10 MeV. Typical electron beam irradiation device power can be 1 KW, 5 KW, 10 KW, 20 KW, 50 KW, 60 KW, 70 KW, 80 KW, 90 KW, 100 KW, 125 KW, 150 KW, 175 KW, 200 KW, 250 KW, 300 KW, 350 KW, 400 KW, 450 KW, 500 KW, 600 KW, 700 KW, 800 KW, 900 KW or even 1000 KW.

Tradeoffs in considering electron beam irradiation device power specifications include cost to operate, capital costs, depreciation, and device footprint. Tradeoffs in considering exposure dose levels of electron beam irradiation would be energy costs and environment, safety, and health (ESH) concerns. Typically, generators are housed in a vault, e.g., of lead or concrete, especially for production from X-rays that are generated in the process. Tradeoffs in considering electron energies include energy costs.

The electron beam irradiation device can produce either a fixed beam or a scanning beam. A scanning beam may be advantageous with large scan sweep length and high scan speeds, as this would effectively replace a large, fixed beam width. Further, available sweep widths of 0.5 m, 1 m, 2 m or more are available. The scanning beam is preferred in most embodiments described herein because of the larger scan width and reduced possibility of local heating and failure of the windows.

Electron Guns—Windows

The extraction system for an electron accelerator can include two window foils. Window foils are described in International App. No. PCT/US2013/064332 filed Oct. 10, 2013 the complete disclosure of which is herein incorporated by reference. The cooling gas in the two foil window extraction system can be a pure gas or a mixture, for example, air, or a pure gas. In one embodiment the gas is an inert gas such as nitrogen, argon, helium and/or carbon dioxide. It is preferred to use a gas rather than a liquid since energy losses to the electron beam are minimized Mixtures of pure gas can also be used, either pre-mixed or mixed in line prior to impinging on the windows or in the space between the windows. The cooling gas can be cooled, for example, by using a heat exchange system (e.g., a chiller) and/or by using boil off from a condensed gas (e.g., liquid nitrogen, liquid helium).

When using an enclosure, the enclosed conveyor can also be purged with an inert gas so as to maintain an atmosphere at a reduced oxygen level. Keeping oxygen levels low avoids the formation of ozone which in some instances is undesirable due to its reactive and toxic nature. For example, the oxygen can be less than about 20% (e.g., less than about 10%, less than about 1%, less than about 0.1%, less than about 0.01%, or even less than about 0.001% oxygen). Purging can be done with an inert gas including, but not limited to, nitrogen, argon, helium or carbon dioxide. This can be supplied, for example, from a boil off of a liquid source (e.g., liquid nitrogen or helium), generated or separated from air in situ, or supplied from tanks. The inert gas can be recirculated and any residual oxygen can be removed using a catalyst, such as a copper catalyst bed. Alternatively, combinations of purging, recirculating and oxygen removal can be done to keep the oxygen levels low.

The enclosure can also be purged with a reactive gas that can react with the biomass. This can be done before, during or after the irradiation process. The reactive gas can be, but is not limited to, nitrous oxide, ammonia, oxygen, ozone, hydrocarbons, aromatic compounds, amides, peroxides, azides, halides, oxyhalides, phosphides, phosphines, arsines, sulfides, thiols, boranes and/or hydrides. The reactive gas can be activated in the enclosure, e.g., by irradiation (e.g., electron beam, UV irradiation, microwave irradiation, heating, IR radiation), so that it reacts with the biomass. The biomass itself can be activated, for example, by irradiation. Preferably the biomass is activated by the electron beam, to produce radicals which then react with the activated or unactivated reactive gas, e.g., by radical coupling or quenching.

Purging gases supplied to an enclosed conveyor can also be cooled, for example, below about 25° C., below about 0° C., below about −40° C., below about −80° C., below about −120° C. For example, the gas can be boiled off from a compressed gas such as liquid nitrogen or sublimed from solid carbon dioxide. As an alternative example, the gas can be cooled by a chiller or part of or the entire conveyor can be cooled.

Heating and Throughput During Radiation Treatment

Several processes can occur in biomass when electrons from an electron beam interact with matter in inelastic collisions. For example, ionization of the material, chain scission of polymers in the material, cross linking of polymers in the material, oxidation of the material, generation of X-rays ("Bremsstrahlung") and vibrational excitation of molecules (e.g. phonon generation). Without being bound to a particular mechanism, the reduction in recalcitrance can be due to several of these inelastic collision effects, for example, ionization, chain scission of polymers, oxidation and phonon generation. Some of the effects (e.g., especially X-ray generation), necessitate shielding and engineering barriers, for example, enclosing the irradiation processes in a concrete (or other radiation opaque material) vault. Another effect of irradiation, vibrational excitation, is equivalent to heating up the sample. Heating the sample by irradiation can help in recalcitrance reduction, but excessive heating can destroy the material, as will be explained below.

The adiabatic temperature rise ($\Delta T$) from adsorption of ionizing radiation is given by the equation: $\Delta T = D/C_p$: where D is the average dose in KGy, $C_p$ is the heat capacity in J/g °C., and $\Delta T$ is the change in temperature in °C. A typical dry biomass material will have a heat capacity close to 2. Wet biomass will have a higher heat capacity dependent on the amount of water since the heat capacity of water is very high (4.19 J/g °C.). Metals have much lower heat capacities, for example, 304 stainless steel has a heat capacity of 0.5 J/g °C. The temperature change due to the instant adsorption of radiation in a biomass and stainless steel for various doses of radiation is shown in Table 1.

TABLE 1

Calculated Temperature increase for biomass and stainless steel.

| Dose (Mrad) | Estimated Biomass $\Delta T$ (° C.) | Steel $\Delta T$ (° C.) |
|---|---|---|
| 10 | 50 | 200 |
| 50 | 250, Decomposition | 1000 |
| 100 | 500, Decomposition | 2000 |
| 150 | 750, Decomposition | 3000 |
| 200 | 1000, Decomposition | 4000 |

High temperatures can destroy and or modify the biopolymers in biomass so that the polymers (e.g., cellulose) are unsuitable for further processing. A biomass subjected to high temperatures can become dark, sticky and give off odors indicating decomposition. The stickiness can even make the material hard to convey. The odors can be unpleasant and be a safety issue. In fact, keeping the biomass below about 200° C. has been found to be beneficial in the processes described herein (e.g., below about 190° C., below about 180° C., below about 170° C., below about 160° C., below about 150° C., below about 140° C., below about 130° C., below about 120° C., below about 110° C., between about 60° C. and 180° C., between about 60° C. and 160° C., between about 60° C. and 150° C., between about 60° C. and 140° C., between about 60° C. and 130° C., between about 60° C. and 120° C., between about 80° C. and 180° C., between about 100° C. and 180° C., between about 120° C. and 180° C., between about 140° C. and 180° C., between about 160° C. and 180° C., between about 100° C. and 140° C., between about 80° C. and 120° C.).

It has been found that irradiation above about 10 Mrad is desirable for the processes described herein (e.g., reduction of recalcitrance). A high throughput is also desirable so that the irradiation does not become a bottle neck in processing the biomass. The treatment is governed by a Dose rate equation: M=FP/D*time, where M is the mass of irradiated material (Kg), F is the fraction of power that is adsorbed (unit less), P is the emitted power (KW=Voltage in MeV*Current in mA), time is the treatment time (sec) and D is the adsorbed dose (KGy). In an exemplary process where the fraction of adsorbed power is fixed, the Power emitted is constant and a set dosage is desired, the throughput (e.g., M, the biomass processed) can be increased by increasing the irradiation time. However, increasing the irradiation time without allowing the material to cool, can excessively heat the material as exemplified by the calculations shown above. Since biomass has a low thermal conductivity (less than about 0.1 Wm$^{-1}$K$^{-1}$), heat dissipation is slow, unlike, for example, metals (greater than about 10 Wm$^{-1}$K$^{-1}$) which can dissipate energy quickly as long as there is a heat sink to transfer the energy to.

Electron Guns—Beam Stops

In some embodiments the systems and methods include a beam stop (e.g., a shutter). For example, the beam stop can be used to quickly stop or reduce the irradiation of material without powering down the electron beam device. Alternatively the beam stop can be used while powering up the electron beam, e.g., the beam stop can stop the electron beam until a beam current of a desired level is achieved. The beam stop can be placed between the primary foil window and a secondary foil window. For example, the beam stop can be mounted so that it is movable, that is, so that it can be moved into and out of the beam path. Even partial coverage of the beam can be used, for example, to control the dose of irradiation. The beam stop can be mounted to the floor, to a conveyor for the biomass, to a wall, to the radiation device (e.g., at the scan horn), or to any structural support. Preferably, the beam stop is fixed in relation to the scan horn so that the beam can be effectively controlled by the beam stop. The beam stop can incorporate a hinge, a rail, wheels, slots, or other means allowing for its operation in moving into and out of the beam. The beam stop can be made of any material that will stop at least 5% of the electrons, e.g., at least 10%, 20%, 30%, 40%, 50%, 60%, 70%, at least 80%, 85%, 90%, 91%, 92%, 93%, 94%, 95%, 96%, 97%, 98%, 99% or even about 100% of the electrons.

The beam stop can be made of a metal including, but not limited to, stainless steel, lead, iron, molybdenum, silver, gold, titanium, aluminum, tin, or alloys of these, or laminates (layered materials) made with such metals (e.g., metal-coated ceramic, metal-coated polymer, metal-coated composite, multilayered metal materials).

The beam stop can be cooled, for example, with a cooling fluid such as an aqueous solution or a gas. The beam stop can be partially or completely hollow, for example, with cavities. Interior spaces of the beam stop can be used for cooling fluids and gases. The beam stop can be of any shape, including flat, curved, round, oval, square, rectangular, beveled and wedged shapes.

The beam stop can have perforations so as to allow some electrons through, thus controlling (e.g., reducing) the levels of radiation across the whole area of the window, or in specific regions of the window. The beam stop can be a mesh formed, for example, from fibers or wires. Multiple beam stops can be used, together or independently, to control the irradiation. The beam stop can be remotely controlled, e.g., by radio signal or hard wired to a motor for moving the beam into or out of position.

Biomass Materials

Lignocellulosic materials include, but are not limited to, wood (e.g., softwood, Pine softwood, Softwood, Softwood barks, Softwood stems, Spruce softwood, Hardwood, Willow Hardwood, aspen hardwood, Birch Hardwood, Hardwood barks, Hardwood stems, pine cones, pine needles), particle board, chemical pulps, mechanical pulps, paper, waste paper, forestry wastes (e.g., sawdust, aspen wood, wood chips, leaves), grasses, (e.g., switchgrass, miscanthus, cord grass, reed canary grass, Coastal Bermuda grass), grain residues, (e.g., rice hulls, oat hulls, wheat chaff, barley hulls), agricultural waste (e.g., silage, canola straw, wheat straw, barley straw, oat straw, rice straw, jute, hemp, flax, bamboo, sisal, abaca, corn cobs, corn stover, soybean stover, corn fiber, alfalfa, hay, coconut hair, nut shells, palm and coconut oil byproducts), cotton, Cotton seed hairs, flax, sugar processing residues (e.g., bagasse, beet pulp, agave bagasse), algae, seaweed, manure (e.g., Solid cattle manure, Swine waste), sewage, carrot processing waste, molasses spent wash, alfalfa biver and mixtures of any of these.

In some cases, the lignocellulosic material includes corncobs. Ground or hammermilled corncobs can be spread in a layer of relatively uniform thickness for irradiation, and after irradiation are easy to disperse in the medium for further processing. To facilitate harvest and collection, in some cases the entire corn plant is used, including the corn stalk, corn kernels, and in some cases even the root system of the plant.

Advantageously, no additional nutrients (other than a nitrogen source, e.g., urea or ammonia) are required during fermentation of corncobs or cellulosic or lignocellulosic materials containing significant amounts of corncobs.

Corncobs, before and after comminution, are also easier to convey and disperse, and have a lesser tendency to form explosive mixtures in air than other cellulosic or lignocellulosic materials such as hay and grasses.

Cellulosic materials include, for example, paper, paper products, paper waste, paper pulp, pigmented papers, loaded papers, coated papers, filled papers, magazines, printed matter (e.g., books, catalogs, manuals, labels, calendars, greeting cards, brochures, prospectuses, newsprint), printer paper, polycoated paper, card stock, cardboard, paperboard, materials having a high α-cellulose content such as cotton, and mixtures of any of these. For example, paper products as described in U.S. application Ser. No. 13/396,365 ("Magazine Feedstocks" by Medoff et al., filed Feb. 14, 2012), the full disclosure of which is incorporated herein by reference.

Cellulosic materials can also include lignocellulosic materials which have been partially or fully de-lignified.

In some instances other biomass materials can be utilized, for example, starchy materials. Starchy materials include starch itself, e.g., corn starch, wheat starch, potato starch or rice starch, a derivative of starch, or a material that includes starch, such as an edible food product or a crop. For example, the starchy material can be arracacha, buckwheat, banana, barley, cassava, kudzu, ocra, sago, sorghum, regular household potatoes, sweet potato, taro, yams, or one or more beans, such as favas, lentils or peas. Blends of any two or more starchy materials are also starchy materials. Mixtures of starchy, cellulosic and or lignocellulosic materials can also be used. For example, a biomass can be an entire plant, a part of a plant or different parts of a plant, e.g., a wheat plant, cotton plant, a corn plant, rice plant or a tree. The starchy materials can be treated by any of the methods described herein.

Microbial materials include, but are not limited to, any naturally occurring or genetically modified microorganism or organism that contains or is capable of providing a source of carbohydrates (e.g., cellulose), for example, protists, e.g., animal protists (e.g., protozoa such as *flagellates*, amoeboids, ciliates, and sporozoa) and plant protists (e.g., algae such alveolates, chlorarachniophytes, cryptomonads, euglenids, glaucophytes, haptophytes, red algae, stramenopiles, and viridiplantae). Other examples include seaweed, plankton (e.g., macroplankton, mesoplankton, microplankton, nanoplankton, picoplankton, and femtoplankton), phytoplankton, bacteria (e.g., gram positive bacteria, gram negative bacteria, and extremophiles), yeast and/or mixtures of these. In some instances, microbial biomass can be obtained from natural sources, e.g., the ocean, lakes, bodies of water, e.g., salt water or fresh water, or on land. Alternatively or in addition, microbial biomass can be obtained from culture systems, e.g., large scale dry and wet culture and fermentation systems.

In other embodiments, the biomass materials, such as cellulosic, starchy and lignocellulosic feedstock materials, can be obtained from transgenic microorganisms and plants that have been modified with respect to a wild type variety. Such modifications may be, for example, through the iterative steps of selection and breeding to obtain desired traits in a plant. Furthermore, the plants can have had genetic material removed, modified, silenced and/or added with respect to the wild type variety. For example, genetically modified plants can be produced by recombinant DNA methods, where genetic modifications include introducing or modifying specific genes from parental varieties, or, for example, by using transgenic breeding wherein a specific gene or genes are introduced to a plant from a different species of plant and/or bacteria. Another way to create genetic variation is through mutation breeding wherein new alleles are artificially created from endogenous genes. The artificial genes can be created by a variety of ways including treating the plant or seeds with, for example, chemical mutagens (e.g., using alkylating agents, epoxides, alkaloids, peroxides, formaldehyde), irradiation (e.g., X-rays, gamma rays, neutrons, beta particles, alpha particles, protons, deuterons, UV radiation) and temperature shocking or other external stressing and subsequent selection techniques. Other methods of providing modified genes is through error prone PCR and DNA shuffling followed by insertion of the desired modified DNA into the desired plant or seed. Methods of introducing the desired genetic variation in the seed or plant include, for example, the use of a bacterial carrier, biolistics, calcium phosphate precipitation, electroporation, gene splicing, gene silencing, lipofection, microinjection and viral carriers. Additional genetically modified materials have been described in U.S. application Ser. No. 13/396,369 filed Feb. 14, 2012 the full disclosure of which is incorporated herein by reference.

Any of the methods described herein can be practiced with mixtures of any biomass materials described herein.

Biomass Material Preparation—Mechanical Treatments

The biomass can be in a dry form, for example, with less than about 35% moisture content (e.g., less than about 20%, less than about 15%, less than about 10% less than about 5%, less than about 4%, less than about 3%, less than about 2% or even less than about 1%). The biomass can also be delivered in a wet state, for example, as a wet solid, a slurry or a suspension with at least about 10 wt. % solids (e.g., at least about 20 wt. %, at least about 30 wt. %, at least about 40 wt. %, at least about 50 wt. %, at least about 60 wt. %, at least about 70 wt. %).

The processes disclosed herein can utilize low bulk density materials, for example, cellulosic or lignocellulosic feedstocks that have been physically pretreated to have a bulk density of less than about 0.75 g/cm$^3$, e.g., less than about 0.7, 0.65, 0.60, 0.50, 0.35, 0.25, 0.20, 0.15, 0.10, 0.05 or less, e.g., less than about 0.025 g/cm$^3$. Bulk density is determined using ASTM D1895B. Briefly, the method involves filling a measuring cylinder of known volume with a sample and obtaining a weight of the sample. The bulk density is calculated by dividing the weight of the sample in grams by the known volume of the cylinder in cubic centimeters. If desired, low bulk density materials can be densified, for example, by methods described in U.S. Pat. No. 7,971,809 to Medoff, the full disclosure of which is hereby incorporated by reference.

In some cases, the pre-treatment processing includes screening of the biomass material. Screening can be through a mesh or perforated plate with a desired opening size, for example, less than about 6.35 mm (¼ inch, 0.25 inch), (e.g., less than about 3.18 mm (⅛ inch, 0.125 inch), less than about 1.59 mm (1/16 inch, 0.0625 inch), is less than about 0.79 mm (1/32 inch, 0.03125 inch), e.g., less than about 0.51 mm (1/50 inch, 0.02000 inch), less than about 0.40 mm (1/64 inch, 0.015625 inch), less than about 0.23 mm (0.009 inch), less than about 0.20 mm (1/128 inch, 0.0078125 inch), less than about 0.18 mm (0.007 inch), less than about 0.13 mm (0.005 inch), or even less than about 0.10 mm (1/256 inch, 0.00390625 inch)). In one configuration the desired biomass falls through the perforations or screen and thus biomass larger than the perforations or screen are not irradiated. These larger materials can be re-processed, for example, by comminuting, or they can simply be removed from processing. In another configuration, material that is larger than the perforations is irradiated and the smaller material is removed by the screening process or recycled. In this kind of a configuration, the conveyor itself (for example, a part of the conveyor) can be perforated or made with a mesh. For example, in one particular embodiment the biomass material may be wet and the perforations or mesh allow water to drain away from the biomass before irradiation.

Screening of material can also be by a manual method, for example, by an operator or mechanoid (e.g., a robot equipped with a color, reflectivity or other sensor) that removes unwanted material. Screening can also be by magnetic screening wherein a magnet is disposed near the conveyed material and the magnetic material is removed magnetically.

Optional pre-treatment processing can include heating the material. For example, a portion of the conveyor can be sent through a heated zone. The heated zone can be created, for example, by IR radiation, microwaves, combustion (e.g., gas, coal, oil, biomass), resistive heating and/or inductive coils. The heat can be applied from at least one side or more than one side, can be continuous or periodic and can be for only a portion of the material or all the material. For example, a portion of the conveying trough can be heated by use of a heating jacket. Heating can be, for example, for the purpose of drying the material. In the case of drying the material, this can also be facilitated, with or without heating, by the movement of a gas (e.g., air, oxygen, nitrogen, He, $CO_2$, Argon) over and/or through the biomass as it is being conveyed.

Optionally, pre-treatment processing can include cooling the material. Cooling material is described in U.S. Pat. No. 7,900,857 to Medoff, the disclosure of which in incorporated herein by reference. For example, cooling can be by supplying a cooling fluid, for example, water (e.g., with glycerol), or nitrogen (e.g., liquid nitrogen) to the bottom of the conveying trough. Alternatively, a cooling gas, for example, chilled nitrogen can be blown over the biomass materials or under the conveying system.

Another optional pre-treatment processing method can include adding a material to the biomass. The additional material can be added by, for example, by showering, sprinkling and or pouring the material onto the biomass as it is conveyed. Materials that can be added include, for example, metals, ceramics and/or ions as described in U.S. Pat. App. Pub. 2010/0105119 A1 (filed Oct. 26, 2009) and U.S. Pat. App. Pub. 2010/0159569 A1 (filed Dec. 16, 2009), the entire disclosures of which are incorporated herein by reference. Optional materials that can be added include acids and bases. Other materials that can be added are oxidants (e.g., peroxides, chlorates), polymers, polymerizable monomers (e.g., containing unsaturated bonds), water, catalysts, enzymes and/or organisms. Materials can be added, for example, in pure form, as a solution in a solvent (e.g., water or an organic solvent) and/or as a solution. In some cases the solvent is volatile and can be made to evaporate e.g., by heating and/or blowing gas as previously described. The added material may form a uniform coating on the biomass or be a homogeneous mixture of different components (e.g., biomass and additional material). The added material can modulate the subsequent irradiation step by increasing the efficiency of the irradiation, damping the irradiation or changing the effect of the irradiation (e.g., from electron beams to X-rays or heat). The method may have no impact on the irradiation but may be useful for further downstream processing. The added material may help in conveying the material, for example, by lowering dust levels.

Biomass can be delivered to the conveyor (e.g., the vibratory conveyors used in the vaults herein described) by a belt conveyor, a pneumatic conveyor, a screw conveyor, a hopper, a pipe, manually or by a combination of these. The biomass can, for example, be dropped, poured and/or placed onto the conveyor by any of these methods. In some embodiments the material is delivered to the conveyor using an enclosed material distribution system to help maintain a low oxygen atmosphere and/or control dust and fines. Lofted or air suspended biomass fines and dust are undesirable because these can form an explosion hazard or damage the window foils of an electron gun (if such a device is used for treating the material).

The material can be leveled to form a uniform thickness between about 0.0312 and 5 inches (e.g., between about 0.0625 and 2.000 inches, between about 0.125 and 1 inches, between about 0.125 and 0.5 inches, between about 0.3 and 0.9 inches, between about 0.2 and 0.5 inches between about 0.25 and 1.0 inches, between about 0.25 and 0.5 inches, 0.100+/−0.025 inches, 0.150+/−0.025 inches, 0.200+/−0.025 inches, 0.250+/−0.025 inches, 0.300+/−0.025 inches, 0.350+/−0.025 inches, 0.400+/−0.025 inches, 0.450+/−0.025 inches, 0.500+/−0.025 inches, 0.550+/−0.025 inches, 0.600+/−0.025 inches, 0.700+/−0.025 inches, 0.750+/−0.025 inches, 0.800+/−0.025 inches, 0.850+/−0.025 inches, 0.900+/−0.025 inches, 0.900+/−0.025 inches.

Generally, it is preferred to convey the material as quickly as possible through the electron beam to maximize throughput. For example, the material can be conveyed at rates of at least 1 ft./min, e.g., at least 2 ft./min, at least 3 ft./min, at least 4 ft./min, at least 5 ft./min, at least 10 ft./min, at least 15 ft./min, 20, 25, 30, 35, 40, 45, 50 ft./min. The rate of conveying is related to the beam current, for example, for a ¼ inch thick biomass and 100 mA, the conveyor can move at about 20 ft/min to provide a useful irradiation dosage, at 50 mA the conveyor can move at about 10 ft/min to provide approximately the same irradiation dosage.

After the biomass material has been conveyed through the radiation zone, optional post-treatment processing can be done. The optional post-treatment processing can, for example, be a process described with respect to the pre-irradiation processing. For example, the biomass can be screened, heated, cooled, and/or combined with additives. Uniquely to post-irradiation, quenching of the radicals can occur, for example, quenching of radicals by the addition of fluids or gases (e.g., oxygen, nitrous oxide, ammonia, liquids), using pressure, heat, and/or the addition of radical scavengers. For example, the biomass can be conveyed out of the enclosed conveyor and exposed to a gas (e.g., oxygen) where it is quenched, forming carboxylated groups. In one embodiment, the biomass is exposed during irradiation to the reactive gas or fluid. Quenching of biomass that has been irradiated is described in U.S. Pat. No. 8,083,906 to Medoff, the entire disclosure of which is incorporate herein by reference.

If desired, one or more mechanical treatments can be used in addition to irradiation to further reduce the recalcitrance of the carbohydrate-containing material. These processes can be applied before, during and or after irradiation.

In some cases, the mechanical treatment may include an initial preparation of the feedstock as received, e.g., size reduction of materials, such as by comminution, e.g., cutting, grinding, shearing, pulverizing or chopping. For example, in some cases, loose feedstock (e.g., recycled paper, starchy materials, or switchgrass) is prepared by shearing or shredding. Mechanical treatment may reduce the bulk density of the carbohydrate-containing material, increase the surface area of the carbohydrate-containing material and/or decrease one or more dimensions of the carbohydrate-containing material.

Alternatively, or in addition, the feedstock material can be treated with another treatment, for example, chemical treatments, such as with an acid (HCl, $H_2SO_4$, $H_3PO_4$), a base (e.g., KOH and NaOH), a chemical oxidant (e.g., peroxides, chlorates, ozone), irradiation, steam explosion, pyrolysis, sonication, oxidation, chemical treatment. The treatments can be in any order and in any sequence and combinations. For example, the feedstock material can first be physically treated by one or more treatment methods, e.g., chemical treatment including and in combination with acid hydrolysis (e.g., utilizing HCl, $H_2SO_4$, $H_3PO_4$), radiation, sonication, oxidation, pyrolysis or steam explosion, and then mechanically treated. This sequence can be advantageous since materials treated by one or more of the other treatments, e.g., irradiation or pyrolysis, tend to be more brittle and, therefore, it may be easier to further change the structure of the material by mechanical treatment. As another example, a feedstock material can be conveyed through ionizing radiation using a conveyor as described herein and then mechanically treated. Chemical treatment can remove some or all of the lignin (for example, chemical pulping) and can partially or completely hydrolyze the material. The methods also can be used with pre-hydrolyzed material. The methods also can be used with material that has not been pre hydrolyzed The methods can be used with mixtures of hydrolyzed and non-hydrolyzed materials, for example, with about 50% or more non-hydrolyzed material, with about 60% or more non-hydrolyzed material, with about 70% or more non-hydrolyzed material, with about 80% or more non-hydrolyzed material or even with 90% or more non-hydrolyzed material.

In addition to size reduction, which can be performed initially and/or later in processing, mechanical treatment can also be advantageous for "opening up," "stressing," breaking or shattering the carbohydrate-containing materials, making the cellulose of the materials more susceptible to chain scission and/or disruption of crystalline structure during the physical treatment.

Methods of mechanically treating the carbohydrate-containing material include, for example, milling or grinding. Milling may be performed using, for example, a hammer mill, ball mill, colloid mill, conical or cone mill, disk mill, edge mill, Wiley mill, grist mill or other mill. Grinding may be performed using, for example, a cutting/impact type grinder. Some exemplary grinders include stone grinders, pin grinders, coffee grinders, and burr grinders. Grinding or milling may be provided, for example, by a reciprocating pin or other element, as is the case in a pin mill Other mechanical treatment methods include mechanical ripping or tearing, other methods that apply pressure to the fibers, and air attrition milling. Suitable mechanical treatments further include any other technique that continues the disruption of the internal structure of the material that was initiated by the previous processing steps.

Mechanical feed preparation systems can be configured to produce streams with specific characteristics such as, for example, specific maximum sizes, specific length-to-width, or specific surface areas ratios. Physical preparation can increase the rate of reactions, improve the movement of material on a conveyor, improve the irradiation profile of the material, improve the radiation uniformity of the material, or reduce the processing time required by opening up the materials and making them more accessible to processes and/or reagents, such as reagents in a solution.

The bulk density of feedstocks can be controlled (e.g., increased). In some situations, it can be desirable to prepare a low bulk density material, e.g., by densifying the material (e.g., densification can make it easier and less costly to transport to another site) and then reverting the material to a lower bulk density state (e.g., after transport). The material can be densified, for example, from less than about 0.2 g/cc to more than about 0.9 g/cc (e.g., less than about 0.3 to more than about 0.5 g/cc, less than about 0.3 to more than about 0.9 g/cc, less than about 0.5 to more than about 0.9 g/cc, less than about 0.3 to more than about 0.8 g/cc, less than about 0.2 to more than about 0.5 g/cc). For example, the material can be densified by the methods and equipment disclosed in U.S. Pat. No. 7,932,065 to Medoff and International Publication No. WO 2008/073186 (which was filed Oct. 26, 2007, was published in English, and which designated the United States), the full disclosures of which are incorporated herein by reference. Densified materials can be processed by any of the methods described herein, or any material processed by any of the methods described herein can be subsequently densified.

In some embodiments, the material to be processed is in the form of a fibrous material that includes fibers provided by shearing a fiber source. For example, the shearing can be performed with a rotary knife cutter.

For example, a fiber source, e.g., that is recalcitrant or that has had its recalcitrance level reduced, can be sheared, e.g., in a rotary knife cutter, to provide a first fibrous material. The first fibrous material is passed through a first screen, e.g., having an average opening size of 1.59 mm or less (1/16 inch, 0.0625 inch), provide a second fibrous material. If desired, the fiber source can be cut prior to the shearing, e.g., with a shredder. For example, when a paper is used as the fiber source, the paper can be first cut into strips that are, e.g., ¼- to ½-inch wide, using a shredder, e.g., a counter-rotating screw shredder, such as those manufactured by Munson (Utica, N.Y.). As an alternative to shredding, the paper can be reduced in size by cutting to a desired size using a guillotine cutter. For example, the guillotine cutter can be used to cut the paper into sheets that are, e.g., 10 inches wide by 12 inches long.

In some embodiments, the shearing of the fiber source and the passing of the resulting first fibrous material through a first screen are performed concurrently. The shearing and the passing can also be performed in a batch-type process.

For example, a rotary knife cutter can be used to concurrently shear the fiber source and screen the first fibrous material. A rotary knife cutter includes a hopper that can be loaded with a shredded fiber source prepared by shredding a fiber source.

In some implementations, the feedstock is physically treated prior to saccharification and/or fermentation. Physical treatment processes can include one or more of any of those described herein, such as mechanical treatment, chemical treatment, irradiation, sonication, oxidation, pyrolysis or steam explosion. Treatment methods can be used in combinations of two, three, four, or even all of these technologies (in any order). When more than one treatment method is used, the methods can be applied at the same time or at different times. Other processes that change a molecular structure of a biomass feedstock may also be used, alone or in combination with the processes disclosed herein.

Mechanical treatments that may be used, and the characteristics of the mechanically treated carbohydrate-containing materials, are described in further detail in U.S. Pat. App. Pub. 2012/0100577 A1, filed Oct. 18, 2011, the full disclosure of which is hereby incorporated herein by reference.

The mechanical treatments described herein can also be applied to processing of PLA and PLA based materials.
Sonication, Pyrolysis, Oxidation, Steam Explosion If desired, one or more sonication, pyrolysis, oxidative, or steam explosion processes can be used instead of or in addition to irradiation to reduce or further reduce the recalcitrance of the carbohydrate-containing material or process PLA and/or PLA based materials. For example, these processes can be applied before, during and or after irradiation. These processes are described in detail in U.S. Pat. No. 7,932,065 to Medoff, the full disclosure of which is incorporated herein by reference.
Heat Treatment of Biomass Alternately, or in addition to the biomass may be heat treated for up to twelve hours at temperatures ranging from about 90° C. to about 160° C. Optionally, this heat treatment step is performed after biomass has been irradiated with an electron beam. The amount of time for the heat treatment is up to 9 hours, alternately up to 6 hours, optionally up to 4 hours and further up to about 2 hours. The treatment time can be up to as little as 30 minutes when the mass may be effectively heated.

The heat treatment can be performed 90° C. to about 160° C. or, optionally, at 100 to 150 or, alternatively, at 120 to 140° C. The biomass is suspended in water such that the biomass content is 10 to 75 wt. % in water. In the case of the biomass being the irradiated biomass water is added and the heat treatment performed.

The heat treatment is performed in an aqueous suspension or mixture of the biomass. The amount of biomass is 10 to 90 wt. % of the total mixture, alternatively 20 to 70 wt. % or optionally 25 to 50 wt. %. The irradiated biomass may have minimal water content so water must be added prior to the heat treatment.

Since at temperatures above 100° C. there will be pressure vessel required to accommodate the pressure due to the vaporized of water. The process for the heat treatment may be batch, continuous, semi-continuous or other reactor configurations. The continuous reactor configuration may be a tubular reactor and may include device(s) within the tube which will facilitate heat transfer and mixing/suspension of the biomass. These tubular devices may include a one or more static mixers. The heat may also be put into the system by direct injection of steam.
Use of Treated Biomass Material Using the methods described herein, a starting biomass material (e.g., plant biomass, animal biomass, paper, and municipal waste biomass) can be used as feedstock to produce useful intermediates and products such as organic acids, salts of organic acids, hydroxy-carboxylic acids, PLA, acid anhydrides, esters of organic acids and fuels, e.g., fuels for internal combustion engines or feedstocks for fuel cells. Systems and processes are described herein that can use as feedstock cellulosic and/or lignocellulosic materials that are readily available, but often can be difficult to process, e.g., municipal waste streams and waste paper streams, such as streams that include newspaper, kraft paper, corrugated paper or mixtures of these.

In order to convert the feedstock to a form that can be readily processed, the glucan- or xylan-containing cellulose in the feedstock can be hydrolyzed to low molecular weight carbohydrates, such as sugars, by a saccharifying agent, e.g., an enzyme or acid, a process referred to as saccharification. The low molecular weight carbohydrates can then be used, for example, in an existing manufacturing plant, such as a single cell protein plant, an enzyme manufacturing plant, or a fuel plant, e.g., an ethanol manufacturing facility.

The feedstock can be hydrolyzed using an enzyme, e.g., by combining the materials and the enzyme in a solvent, e.g., in an aqueous solution.

Alternatively, the enzymes can be supplied by organisms that break down biomass, such as the cellulose and/or the lignin portions of the biomass, contain or manufacture various cellulolytic enzymes (cellulases), ligninases or various small molecule biomass-degrading metabolites. These enzymes may be a complex of enzymes that act synergistically to degrade crystalline cellulose or the lignin portions of biomass. Examples of cellulolytic enzymes include: endoglucanases, cellobiohydrolases, and cellobiases (beta-glucosidases).

During saccharification a cellulosic substrate can be initially hydrolyzed by endoglucanases at random locations producing oligomeric intermediates. These intermediates are then substrates for exo-splitting glucanases such as cellobiohydrolase to produce cellobiose from the ends of the cellulose polymer. Cellobiose is a water-soluble 1,4-linked dimer of glucose. Finally, cellobiase cleaves cellobiose to yield glucose. The efficiency (e.g., time to hydrolyze and/or completeness of hydrolysis) of this process depends on the recalcitrance of the cellulosic material.

Intermediates and Products

Using the processes described herein, the biomass material can be converted to one or more products, such as energy, fuels, foods and materials. Specific examples of products include, but are not limited to, hydrogen, sugars (e.g., glucose, xylose, arabinose, mannose, galactose, fructose, disaccharides, oligosaccharides and polysaccharides), alcohols (e.g., monohydric alcohols or dihydric alcohols, such as ethanol, n-propanol, isobutanol, sec-butanol, tert-butanol or n-butanol), hydrated or hydrous alcohols (e.g., containing greater than 10%, 20%, 30% or even greater than 40% water), biodiesel, organic acids, hydrocarbons (e.g., methane, ethane, propane, isobutene, pentane, n-hexane, biodiesel, bio-gasoline and mixtures thereof), co-products (e.g., proteins, such as cellulolytic proteins (enzymes) or single cell proteins), and mixtures of any of these in any combination or relative concentration, and optionally in combination with any additives (e.g., fuel additives). Other examples include carboxylic acids, salts of a carboxylic acid, a mixture of carboxylic acids and salts of carboxylic acids and esters of carboxylic acids (e.g., methyl, ethyl and n-propyl esters), ketones (e.g., acetone), aldehydes (e.g., acetaldehyde), alpha and beta unsaturated acids (e.g., acrylic acid) and olefins (e.g., ethylene). Other alcohols and alcohol derivatives include propanol, propylene glycol, 1,4-butane-diol, 1,3-propanediol, sugar alcohols (e.g., erythritol, glycol, glycerol, sorbitol threitol, arabitol, ribitol, mannitol, dulcitol, fucitol, iditol, isomalt, maltitol, lactitol, xylitol and other polyols), and methyl or ethyl esters of any of these alcohols. Other products include methyl acrylate, methyl methacrylate, lactic acid, PLA, citric acid, formic acid, acetic acid, propionic acid, butyric acid, succinic acid, valeric acid, caproic acid, 3-hydroxypropionic acid, palmitic acid, stearic acid, oxalic acid, malonic acid, glutaric acid, oleic acid, linoleic acid, glycolic acid, gamma-hydroxybutyric acid, and mixtures thereof, salts of any of these acids, mixtures of any of the acids and their respective salts.

Any combination of the above products with each other, and/or of the above products with other products, which other products may be made by the processes described herein or otherwise, may be packaged together and sold as products. The products may be combined, e.g., mixed, blended or co-dissolved, or may simply be packaged or sold together.

Any of the products or combinations of products described herein may be sanitized or sterilized prior to selling the products, e.g., after purification or isolation or even after packaging, to neutralize one or more potentially undesirable contaminants that could be present in the product(s). Such sanitation can be done with electron bombardment, for example, be at a dosage of less than about 20 Mrad, e.g., from about 0.1 to 15 Mrad, from about 0.5 to 7 Mrad, or from about 1 to 3 Mrad.

The processes described herein can produce various by-product streams useful for generating steam and electricity to be used in other parts of the plant (co-generation) or sold on the open market. For example, steam generated from burning by-product streams can be used in a distillation process. As another example, electricity generated from burning by-product streams can be used to power electron beam generators used in pretreatment.

The by-products used to generate steam and electricity are derived from a number of sources throughout the process. For example, anaerobic digestion of wastewater can produce a biogas high in methane and a small amount of waste biomass (sludge). As another example, post-saccharification and/or post-distillate solids (e.g., unconverted lignin, cellulose, and hemicellulose remaining from the pretreatment and primary processes) can be used, e.g., burned, as a fuel.

Other intermediates and products, including food and pharmaceutical products, are described in U.S. Pat. App. Pub. 2010/0124583 A1, published May 20, 2010, to Medoff, the full disclosure of which is hereby incorporated by reference herein.

Lignin Derived Products

The spent biomass (e.g., spent lignocellulosic material) from lignocellulosic processing by the methods described are expected to have a high lignin content and in addition to being useful for producing energy through combustion in a Co-Generation plant, may have uses as other valuable products. For example, the lignin can be used as captured as a plastic, or it can be synthetically upgraded to other plastics. In some instances, it can also be converted to lignosulfonates, which can be utilized as binders, dispersants, emulsifiers or as sequestrants.

When used as a binder, the lignin or a lignosulfonate can, e.g., be utilized in coal briquettes, in ceramics, for binding carbon black, for binding fertilizers and herbicides, as a dust suppressant, in the making of plywood and particle board, for binding animal feeds, as a binder for fiberglass, as a binder in linoleum paste and as a soil stabilizer.

As a dispersant, the lignin or lignosulfonates can be used, e.g., concrete mixes, clay and ceramics, dyes and pigments, leather tanning and in gypsum board.

As an emulsifier, the lignin or lignosulfonates can be used, e.g., in asphalt, pigments and dyes, pesticides and wax emulsions.

As a sequestrant, the lignin or lignosulfonates can be used, e.g., in micro-nutrient systems, cleaning compounds and water treatment systems, e.g., for boiler and cooling systems.

For energy production lignin generally has a higher energy content than holocellulose (cellulose and hemicellulose) since it contains more carbon than holocellulose. For example, dry lignin can have an energy content of between about 11,000 and 12,500 BTU per pound, compared to 7,000 an 8,000 BTU per pound of holocellulose. As such, lignin can be densified and converted into briquettes and pellets for burning. For example, the lignin can be converted into pellets by any method described herein. For a slower burning pellet or briquette, the lignin can be crosslinked, such as applying a radiation dose of between about 0.5 Mrad and 5 Mrad. Crosslinking can make a slower burning form factor. The form factor, such as a pellet or briquette, can be converted to a "synthetic coal" or charcoal by pyrolyzing in the absence of air, e.g., at between 400 and 950° C. Prior to pyrolyzing, it can be desirable to crosslink the lignin to maintain structural integrity.

Co-generation using spent biomass is described in International App. No. PCT/US2014/021634 filed Mar. 7, 2014, the entire disclosure therein is herein incorporated by reference.

Lignin derived products can also be combined with PLA and PLA derived products. (e.g., PLA that has been produced as described herein). For example, lignin and lignin derived products can be blended, grafted to or otherwise combined and/or mixed with PLA. The lignin can, for example, be useful for strengthening, plasticizing or otherwise modifying the PLA.

Saccharification

The treated biomass materials can be saccharified, generally by combining the material and a cellulase enzyme in a fluid medium, e.g., an aqueous solution. In some cases, the material is boiled, steeped, or cooked in hot water prior to saccharification, as described in U.S. Pat. App. Pub. 2012/0100577 A1 by Medoff and Masterman, published on Apr. 26, 2012, the entire contents of which are incorporated herein.

The saccharification may be done by inoculating a raw sugar mixture produced by saccharifying a reduced recalcitrance lignocellulosic material to produce a hydroxy-carboxylic acid. The hydroxy-carboxylic acid can be selected from the group glycolic acid, D-lactic acid, L-lactic acid, D-malic acid, L-malic, citric acid and D-tartaric acid, L-tartaric acid, and meso-tartaric acid. The raw sugar mixture can be the reduced recalcitrance lignocellulosic material which was processed by irradiating the lignocellulosic material with an electron beam.

The saccharification process can be partially or completely performed in a tank (e.g., a tank having a volume of at least 4000, 40,000, or 500,000 L) in a manufacturing plant, and/or can be partially or completely performed in transit, e.g., in a rail car, tanker truck, or in a supertanker or the hold of a ship. The time required for complete saccharification will depend on the process conditions and the carbohydrate-containing material and enzyme used. If saccharification is performed in a manufacturing plant under controlled conditions, the cellulose may be substantially entirely converted to sugar, e.g., glucose in about 12-96 hours. If saccharification is performed partially or completely in transit, saccharification may take longer.

It is generally preferred that the tank contents be mixed during saccharification, e.g., using jet mixing as described in International App. No. PCT/US2010/035331, filed May 18, 2010, which was published in English as WO 2010/135380 and designated the United States, the full disclosure of which is incorporated by reference herein.

The addition of surfactants can enhance the rate of saccharification. Examples of surfactants include non-ionic surfactants, such as a Tween® 20 or Tween® 80 polyethylene glycol surfactants, ionic surfactants, or amphoteric surfactants.

It is generally preferred that the concentration of the sugar solution resulting from saccharification be relatively high, e.g., greater than 40%, or greater than 50, 60, 70, 80, 90 or even greater than 95% by weight. Water may be removed, e.g., by evaporation, to increase the concentration of the sugar solution. This reduces the volume to be shipped, and also inhibits microbial growth in the solution.

Alternatively, sugar solutions of lower concentrations may be used, in which case it may be desirable to add an antimicrobial additive, e.g., a broad spectrum antibiotic, in a low concentration, e.g., 50 to 150 ppm. Other suitable antibiotics include amphotericin B, ampicillin, chloramphenicol, ciprofloxacin, gentamicin, hygromycin B, kanamycin, neomycin, penicillin, puromycin, streptomycin. Antibiotics will inhibit growth of microorganisms during transport and storage, and can be used at appropriate concentrations, e.g., between 15 and 1000 ppm by weight, e.g., between 25 and 500 ppm, or between 50 and 150 ppm. If desired, an antibiotic can be included even if the sugar concentration is relatively high. Alternatively, other additives with anti-microbial of preservative properties may be used. Preferably the antimicrobial additive(s) are food-grade.

A relatively high concentration solution can be obtained by limiting the amount of water added to the carbohydrate-containing material with the enzyme. The concentration can be controlled, e.g., by controlling how much saccharification takes place. For example, concentration can be increased by adding more carbohydrate-containing material to the solution. In order to keep the sugar that is being produced in solution, a surfactant can be added, e.g., one of those discussed above. Solubility can also be increased by increasing the temperature of the solution. For example, the solution can be maintained at a temperature of 40-50° C., 60-80° C., or even higher.

Saccharifying Agents

Suitable cellulolytic enzymes include cellulases from species in the genera *Bacillus, Coprinus, Myceliophthora, Cephalosporium, Scytalidium, Penicillium, Aspergillus, Pseudomonas, Humicola, Fusarium, Thielavia, Acremonium, Chrysosporium* and *Trichoderma*, especially those produced by a strain selected from the species *Aspergillus* (see, e.g., EP Pub. No. 0 458 162), *Humicola insolens* (reclassified as *Scytalidium thermophilum*, see, e.g., U.S. Pat. No. 4,435,307), *Coprinus cinereus, Fusarium oxysporum, Myceliophthora thermophila, Meripilus giganteus, Thielavia terrestris, Acremonium* sp. (including, but not limited to, *A. persicinum, A. acremonium, A. brachypenium, A. dichromosporum, A. obclavatum, A. pinkertoniae, A. roseogriseum, A. incoloratum,* and *A. furatum*). Preferred strains include *Humicola insolens* DSM 1800, *Fusarium oxysporum* DSM 2672, *Myceliophthora thermophila* CBS 117.65, *Cephalosporium* sp. RYM-202, *Acremonium* sp. CBS 478.94, *Acremonium* sp. CBS 265.95, *Acremonium persicinum* CBS 169.65, *Acremonium acremonium* AHU 9519, *Cephalosporium* sp. CBS 535.71, *Acremonium brachypenium* CBS 866.73, *Acremonium dichromosporum* CBS 683.73, *Acremonium obclavatum* CBS 311.74, *Acremonium pinkertoniae* CBS 157.70, *Acremonium roseogriseum* CBS 134.56, *Acremonium incoloratum* CBS 146.62, and *Acremonium* furatum CBS 299.70H. Cellulolytic enzymes may also be obtained from *Chrysosporium*, preferably a strain of *Chrysosporium lucknowense*. Additional strains that can be used include, but are not limited to, *Trichoderma* (particularly *T. viride, T. reesei,* and *T. koningii*), alkalophilic *Bacillus* (see, for example, U.S. Pat. No. 3,844,890 and EP Pub. No. 0 458 162), and *Streptomyces* (see, e.g., EP Pub. No. 0 458 162).

In addition to or in combination to enzymes, acids, bases and other chemicals (e.g., oxidants) can be utilized to saccharify lignocellulosic and cellulosic materials. These can be used in any combination or sequence (e.g., before, after and/or during addition of an enzyme). For example, strong mineral acids can be utilized (e.g. HCl, $H_2SO_4$, $H_3PO_4$) and strong bases (e.g., NaOH, KOH).

Sugars

In the processes described herein, for example, after saccharification, sugars (e.g., glucose and xylose) can be isolated. For example, sugars can be isolated by precipitation, crystallization, chromatography (e.g., simulated moving bed chromatography, high pressure chromatography), centrifugation, extraction, any other isolation method known in the art, and combinations thereof.

Hydrogenation and Other Chemical Transformations

The processes described herein can include hydrogenation. For example, glucose and xylose can be hydrogenated to sorbitol and xylitol respectively. Esters, for example, produced as described herein, can also be hydrogenated. Hydrogenation can be accomplished by use of a catalyst (e.g., Pt/gamma-$Al_2O_3$, Ru/C, Raney Nickel, copper chromite or other catalysts know in the art) in combination with $H_2$ under high pressure (e.g., 10 to 12000 psi). Other types of chemical transformation of the products from the processes described herein can be used, for example, production of organic sugar derived products such (e.g., furfural and furfural-derived products). Chemical transformations of sugar derived products are described in International App. No. PCT/US201/049562, filed Jul. 3, 2013, the disclosure of which is incorporated herein by reference in its entirety.

Fermentation

Yeast and *Zymomonas* bacteria, for example, can be used for fermentation or conversion of sugar(s) to alcohol(s). Other microorganisms are discussed below. The optimum pH for fermentations is about pH 4 to 7. For example, the optimum pH for yeast is from about pH 4 to 5, while the optimum pH for *Zymomonas* is from about pH 5 to 6. Typical fermentation times are about 24 to 168 hours (e.g., 24 to 96 hrs.) with temperatures in the range of 20° C. to 40° C. (e.g., 26° C. to 40° C.), however thermophilic microorganisms prefer higher temperatures.

In some embodiments, e.g., when anaerobic organisms are used, at least a portion of the fermentation is conducted in the absence of oxygen, e.g., under a blanket of an inert gas such as $N_2$, Ar, He, $CO_2$ or mixtures thereof. Additionally, the mixture may have a constant purge of an inert gas flowing through the tank during part of or all of the fermentation. In some cases, anaerobic condition, can be achieved or maintained by carbon dioxide production during the fermentation and no additional inert gas is needed.

In some embodiments, all or a portion of the fermentation process can be interrupted before the low molecular weight sugar is completely converted to a product (e.g., ethanol). The intermediate fermentation products include sugar and carbohydrates in high concentrations. The sugars and carbohydrates can be isolated via any means known in the art. These intermediate fermentation products can be used in preparation of food for human or animal consumption. Additionally or alternatively, the intermediate fermentation products can be ground to a fine particle size in a stainless-steel laboratory mill to produce a flour-like substance. Jet mixing may be used during fermentation, and in some cases saccharification and fermentation are performed in the same tank.

Nutrients for the microorganisms may be added during saccharification and/or fermentation, for example, the food-based nutrient packages described in U.S. Pat. App. Pub. 2012/0052536, filed Jul. 15, 2011, the complete disclosure of which is incorporated herein by reference.

"Fermentation" includes the methods and products that are disclosed in International App. No. PCT/US2012/071093 filed Dec. 20, 2012 and International App. No. PCT/US2012/071097 filed Dec. 12, 2012, the contents of both of which are incorporated by reference herein in their entirety.

Mobile fermenters can be utilized, as described in International App. No. PCT/US2007/074028 (which was filed Jul. 20, 2007, was published in English as WO 2008/011598 and designated the United States) and has a US issued U.S. Pat. No. 8,318,453, the contents of which are incorporated herein in its entirety. Similarly, the saccharification equipment can be mobile. Further, saccharification and/or fermentation may be performed in part or entirely during transit.

Fermentation Agents

The microorganism(s) used in fermentation can be naturally-occurring microorganisms and/or engineered microorganisms. For example, the microorganism can be a bacterium (including, but not limited to, e.g., a cellulolytic bacterium), a fungus, (including, but not limited to, e.g., a yeast), a plant, a protist, e.g., a protozoa or a fungus-like protest (including, but not limited to, e.g., a slime mold), or an alga. When the organisms are compatible, mixtures of organisms can be utilized.

Suitable fermenting microorganisms have the ability to convert carbohydrates, such as glucose, fructose, xylose, arabinose, mannose, galactose, oligosaccharides or polysaccharides into fermentation products. Fermenting microorganisms include strains of the genus *Saccharomyces* spp. (including, but not limited to, *S. cerevisiae* (baker's yeast), *S. distaticus, S. uvarum*), the genus *Kluyveromyces*, (including, but not limited to, *K. marxianus, K. fragilis*), the genus *Candida* (including, but not limited to, *C. pseudotropicalis*, and *C. brassicae*), *Pichia stipitis* (a relative of *Candida shehatae*), the genus *Clavispora* (including, but not limited to, *C. lusitaniae* and *C. opuntiae*), the genus *Pachysolen* (including, but not limited to, *P. tannophilus*), the genus *Bretannomyces* (including, but not limited to, e.g., *B. clausenii* (Philippidis, G. P., 1996, Cellulose bioconversion technology, in Handbook on Bioethanol: Production and Utilization, Wyman, C. E., ed., Taylor & Francis, Washington, D.C., 179-212)). Other suitable microorganisms include, for example, *Zymomonas mobilis, Clostridium* spp. (including, but not limited to, *C. thermocellum* (Philippidis, 1996, supra), *C. saccharobutylacetonicum, C. tyrobutyricum C. saccharobutylicum, C. Puniceum, C. beijernckii*, and *C. acetobutylicum*), *Moniliella* spp. (including but not limited to *M. pollinis, M. tomentosa, M. madida, M. nigrescens, M. oedocephali, M. megachiliensis*), *Yarrowia lipolytica, Aureobasidium* sp., *Trichosporonoides* sp., *Trigonopsis variabilis, Trichosporon* sp., *Moniliellaacetoabutans* sp., *Typhula variabilis, Candida magnoliae, Ustilaginomycetes* sp., *Pseudozyma tsukubaensis*, yeast species of genera *Zygosaccharomyces, Debaryomyces, Hansenula* and *Pichia*, and fungi of the dematioid genus *Torula* (e.g., *T. corallina*).

Many such microbial strains are publicly available, either commercially or through depositories such as the ATCC (American Type Culture Collection, Manassas, Va., USA), the NRRL (Agricultural Research Service Culture Collection, Peoria, Ill., USA), or the DSMZ (Deutsche Sammlung von Mikroorganismen and Zellkulturen GmbH, Braunschweig, Germany), to name a few.

Commercially available yeasts include, for example, Red Star®/Lesaffre Ethanol Red (available from Red Star/Lesaffre, USA), FALI® (available from Fleischmann's Yeast, a division of Burns Philip Food Inc., USA), SUPERSTART® (available from Alltech, now Lallemand), GERT STRAND® (available from Gert Strand AB, Sweden) and FERMOL (available from DSM Specialties).

Distillation

After fermentation, the resulting fluids can be distilled using, for example, a "beer column" to separate ethanol and other alcohols from the majority of water and residual solids. The vapor exiting the beer column can be, e.g., 35% by weight ethanol and can be fed to a rectification column. A mixture of nearly azeotropic (92.5%) ethanol and water from the rectification column can be purified to pure (99.5%) ethanol using vapor-phase molecular sieves. The beer column bottoms can be sent to the first effect of a three-effect evaporator. The rectification column reflux condenser can provide heat for this first effect. After the first effect, solids can be separated using a centrifuge and dried in a rotary dryer. A portion (25%) of the centrifuge effluent can be recycled to fermentation and the rest sent to the second and third evaporator effects. Most of the evaporator condensate can be returned to the process as fairly clean condensate with a small portion split off to waste water treatment to prevent build-up of low-boiling compounds.

Hydrocarbon-Containing Materials

In other embodiments utilizing the methods and systems described herein, hydrocarbon-containing materials can be processed. Any process described herein can be used to treat any hydrocarbon-containing material herein described. "Hydrocarbon-containing materials," as used herein, is meant to include oil sands, oil shale, tar sands, coal dust, coal slurry, bitumen, various types of coal, and other naturally-occurring and synthetic materials that include both hydrocarbon components and solid matter. The solid matter can include rock, sand, clay, stone, silt, drilling slurry, or other solid organic and/or inorganic matter. The term can also include waste products such as drilling waste and by-products, refining waste and by-products, or other waste products containing hydrocarbon components, such as asphalt shingling and covering, asphalt pavement, etc.

Conveying Systems

Various conveying systems can be used to convey the feedstock materials, for example, to a vault and under an electron beam in a vault. Exemplary conveyors are belt conveyors, pneumatic conveyors, screw conveyors, carts, trains, trains or carts on rails, elevators, front loaders, backhoes, cranes, various scrapers and shovels, trucks, and throwing devices can be used. For example, vibratory conveyors can be used in various processes described herein, for example, as disclosed in International App. No. PCT/US2013/064332 filed Oct. 10, 2013, the entire disclosure of which is herein incorporated by reference.

Other Embodiments

Any material, processes or processed materials described herein can be used to make products and/or intermediates such as composites, fillers, binders, plastic additives, adsorbents and controlled release agents. The methods can include densification, for example, by applying pressure and heat to the materials. For example, composites can be made by combining fibrous materials with a resin or polymer (e.g., PLA). For example, radiation cross-linkable resin (e.g., a thermoplastic resin, PLA, and/or PLA derivatives) can be combined with a fibrous material to provide a fibrous material/cross-linkable resin combination. Such materials can be, for example, useful as building materials, protective sheets, containers and other structural materials (e.g., molded and/or extruded products). Absorbents can be, for example, in the form of pellets, chips, fibers and/or sheets. Adsorbents can be used, for example, as pet bedding, packaging material or in pollution control systems. Controlled release matrices can also be the form of, for example, pellets, chips, fibers and or sheets. The controlled release matrices can, for example, be used to release drugs, biocides, fragrances. For example, composites, absorbents and control release agents and their uses are described in International Application No. PCT/US2006/010648, filed Mar. 23, 2006, and U.S. Pat. No. 8,074,910 filed Nov. 22, 2011, the entire disclosures of which are herein incorporated by reference.

In some instances the biomass material is treated at a first level to reduce recalcitrance, e.g., utilizing accelerated electrons, to selectively release one or more sugars (e.g., xylose). The biomass can then be treated to a second level to release one or more other sugars (e.g., glucose). Optionally the biomass can be dried between treatments. The treatments can include applying chemical and biochemical treatments to release the sugars. For example, a biomass material can be treated to a level of less than about 20 Mrad (e.g., less than about 15 Mrad, less than about 10 Mrad, less than about 5 Mrad, less than about 2 Mrad) and then treated with a solution of sulfuric acid, containing less than 10% sulfuric acid (e.g., less than about 9%, less than about 8%, less than about 7%, less than about 6%, less than about 5%, less than about 4%, less than about 3%, less than about 2%, less than about 1%, less than about 0.75%, less than about 0.50%, less than about 0.25%) to release xylose. Xylose, for example, that is released into solution, can be separated from solids and optionally the solids washed with a solvent/solution (e.g., with water and/or acidified water). Optionally, the Solids can be dried, for example, in air and/or under vacuum optionally with heating (e.g., below about 150° C., below about 120° C.) to a water content below about 25 wt. % (below about 20 wt. %, below about 15 wt. %, below about 10 wt. %, below about 5 wt. %). The solids can then be treated with a level of less than about 30 Mrad (e.g., less than about 25 Mrad, less than about 20 Mrad, less than about 15 Mrad, less than about 10 Mrad, less than about 5 Mrad, less than about 1 Mrad or even not at all) and then treated with an enzyme (e.g., a cellulase) to release glucose. The glucose (e.g., glucose in solution) can be separated from the remaining solids. The solids can then be further processed, for example, utilized to make energy or other products (e.g., lignin derived products).

EXAMPLES

L-Lactic Acid Production from Saccharified Corncob in *Lactobacillus* Species.

Material and Methods

Lactic Acid Producing Strains Tested:

The Lactic acid producing stains that were tested are listed in Table 2

TABLE 2

| Lactic acid producing strains tested | |
|---|---|
| NRRL B-441 | *Lactobacillus casei* |
| NRRL B-445 | *Lactobacillus rhamnosus* |
| NRRL B-763 | *Lactobacillus delbrueckii* subspecies *delbrueckii* |
| ATCC 8014 | *Lactobacillus plantarum* |
| ATCC 9649 | *Lactobacillus delbrueckii* subspecies *delbrueckii* |
| B-4525 | *Lactobacillus delbrueckii* subspecies *lactis* |
| B-4390 | *Lactobacillus corniformis* subspecies *torquens* |
| B-227 | *Lactobacillus pentosus* |
| B-4527 | *Lactobacillus brevis* |
| ATCC 25745 | *Pediococcus pentosaceus* |
| NRRL 395 | *Rhizopus oryzae* |
| CBS 112.07 | *Rhizopus oryzae* |

TABLE 2-continued

| Lactic acid producing strains tested | |
|---|---|
| CBS 127.08 | *Rhizopus oryzae* |
| CBS 396.95 | *Rhizopus oryzae* |

Seed Culture

Cells from a frozen (−80° C.) cell bank were cultivated in propagation medium (BD DIFCO™ Lactobacilli MRS Broth) at 37° C., with 150 rpm stiffing for 20 hours. This seed culture was transferred to a 1.2 L (or optionally a 20 L) bioreactors charged with media as describe below.

Main Culture Media

All media included saccharified corncob that had been hammer milled and irradiated with about 35 Mrad of electron beam irradiation. For example, saccharified corn cob can be prepared as described in International App. No. PCT/US2014/021796 filed Mar. 7, 2014, the entire disclosure of which is herein incorporated by reference.

Experiments with various additional media components were also conducted using *Lactobacillus casei* NRRL B-44 as the lactic acid producing organism. A 1.2 L bioreactor with 0.7 L of culture volume was used. A 1% of 20-hour-cultured seed of *Lactobacillus casei* NRRL B-441 was inoculated. No aeration was utilized. The temperature was maintained at about 37° C. Antifoam 204 was also added (0.1%, 1 ml/L) at the beginning of the fermentation.

The experiments are summarized in Table 3. The media components; initial glucose concentration, nitrogen sources, yeast extract concentration, calcium carbonate, metals and inoculum size, were tested for lactic acid yield or lactic acid production rate. In addition to media components, the physical conditions; temperature, agitation, autoclave time and heating (no-autoclave) were tested for lactic acid yield. For these media components and physical reaction conditions the ranges tested, ranges for producing some lactic acid and the ranges are indicated in Table 3.

TABLE 3

| L-Lactic acid production in bioreactor with B-441 | | | | |
|---|---|---|---|---|
| Media Component | Test Parameter | Range-Tested | Range[a] | Range -Optional[b] |
| Initial glucose concentration | Lactic acid concentration | 33-85 g/L | 33-75 g/L | 33-52 g/L |
| Nitrogen Sources Tested | Lactic acid concentration | Yeast extract, Malt extract, Corn steep, Tryptone, Peptone | Yeast extract, Tryptone, Peptone | Yeast extract |
| Yeast Extract[c] | Lactic acid concentration | 0-10 g/L | 2.5-10 g/L | 2.5 g/L |
| Calcium carbonate | Lactic acid concentration | 0-7 wt. %/vol. % | 3-7% wt. %/vol. % | 5 wt. %/vol. % |
| Metal Solutions | Lactic acid concentration | With or without metals | With or without metals | Without metals |
| Minor components: sodium acetate polysorbate 80[d], dipotassium hydrogen phosphate, triammonium citrate | Lactic acid concentration | With or without minor components | With or without minor components | Without minor components |
| Inoculum Size | Lactic acid production rate | 0.1-5 vol. % | 1-5 vol. % | 1 vol. % |
| Physical Condition | Test Parameter | Range-Tested | Range- | Range |
| Temperature | Lactic acid concentration | 27-47° C. | 27-42° C. | 33-37° C. |
| Agitation (in 1.2 L reactor) | Lactic acid concentration | 50-400 rpm | 50-400 rpm | 100-300 rpm |
| Autoclave Time | Lactic acid concentration | 25 min-145 min | 25 min-145 min | 25 min |
| Heating (no autoclave) | Lactic acid concentration | 50-70° C. | 50-70° C. | 50-70° C. |

[a]Ranges produced a yield of at least 80% based on added sugars.
[b]Optional ranges produced close to 100% lactic acid (e.g., between about 90 and 100%, between about 95 and 100%).
[c] Fluka brand yeast extract was used.
[d]Polysorbate ™80 is a nonionic surfactant from ICI Americas, Inc.

Results with Optional Media and Optional Physical Conditions

A 1.2 L bioreactor charged with 0.7 L of media (Saccharified corncob, 2.5 g/L yeast extract). The media and bioreactor vessel were autoclaved for 25 min and no additional heating was used for sterilization. In addition a 20 L bioreactor was charged with 10 L of media. For sterilization the media was stirred at 200 rpm while heating at 80° C. for 10 min. When the media was cool (about 37° C.) the bioreactors were inoculated with 1 vol. % of 20-hour-culture. The fermentations were conducted under the physical conditions (37° C., 200 rpm stirring). No aeration was utilized. The pH remained between 5 and 6 using 5% (wt. %/vol. %) throughout the fermentation. The temperature was maintained at about 37° C. Antifoam 204 was also added (0.1 vol. %) at the beginning of the fermentation. Several *Lactobacillus casei* strains were tested (NRRL B-441, NRRL B-445, NRRL B-763 and ATCC 8014).

Figure 7:
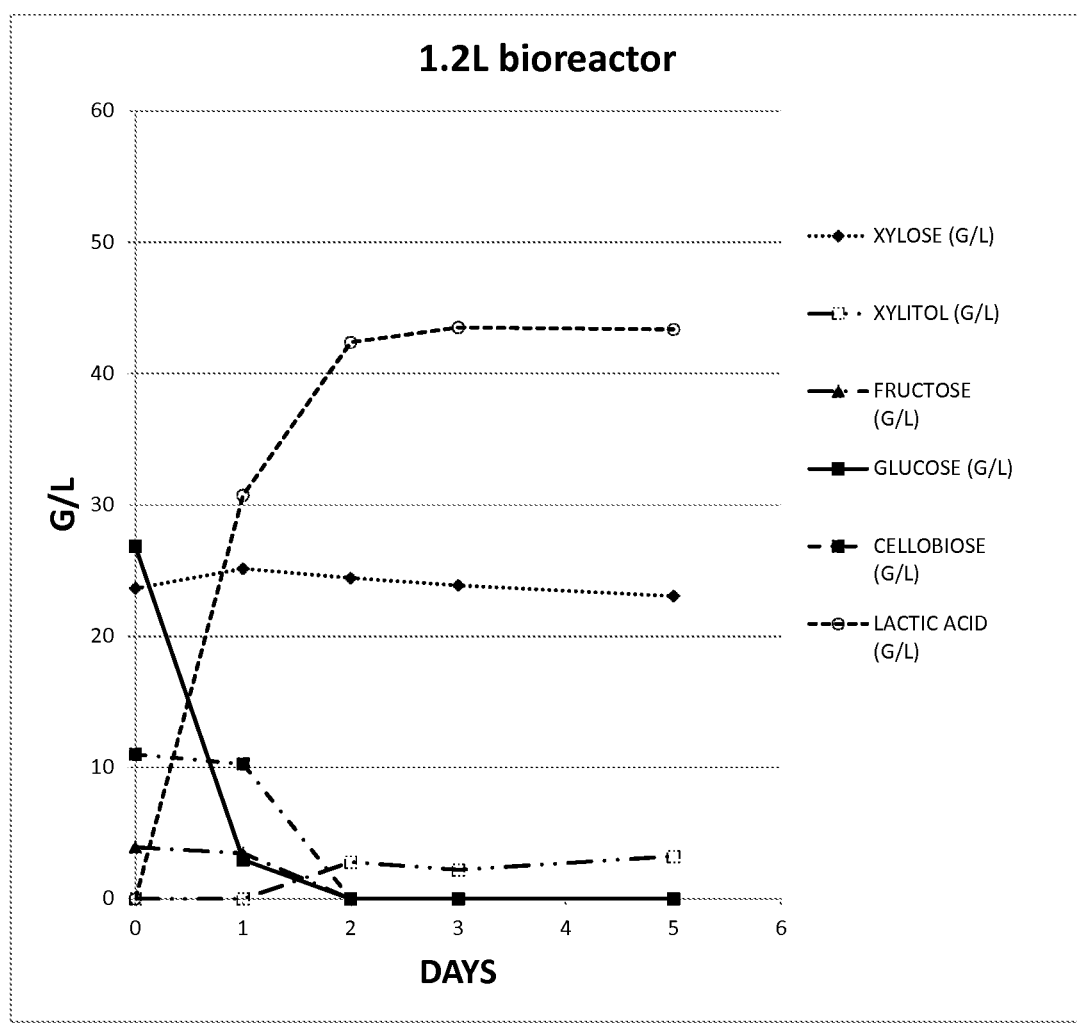
FIG. 7 is a plot of lactic acid production in a 1.2 L Bioreactor.

A plot of the sugar consumption and lactic acid production for the NRRL B-441 strain is shown in the 1.2 L bioreactor is shown in FIG. 7. After two days all of the glucose was consumed, while xylose was not consumed. Fructose and cellobiose were also consumed. Lactic acid was produced at a concentration of about 42 g/L. The consumed glucose, fructose and cellobiose (total 42 g/L) were about to same as produced lactic acid.

Figure 8:
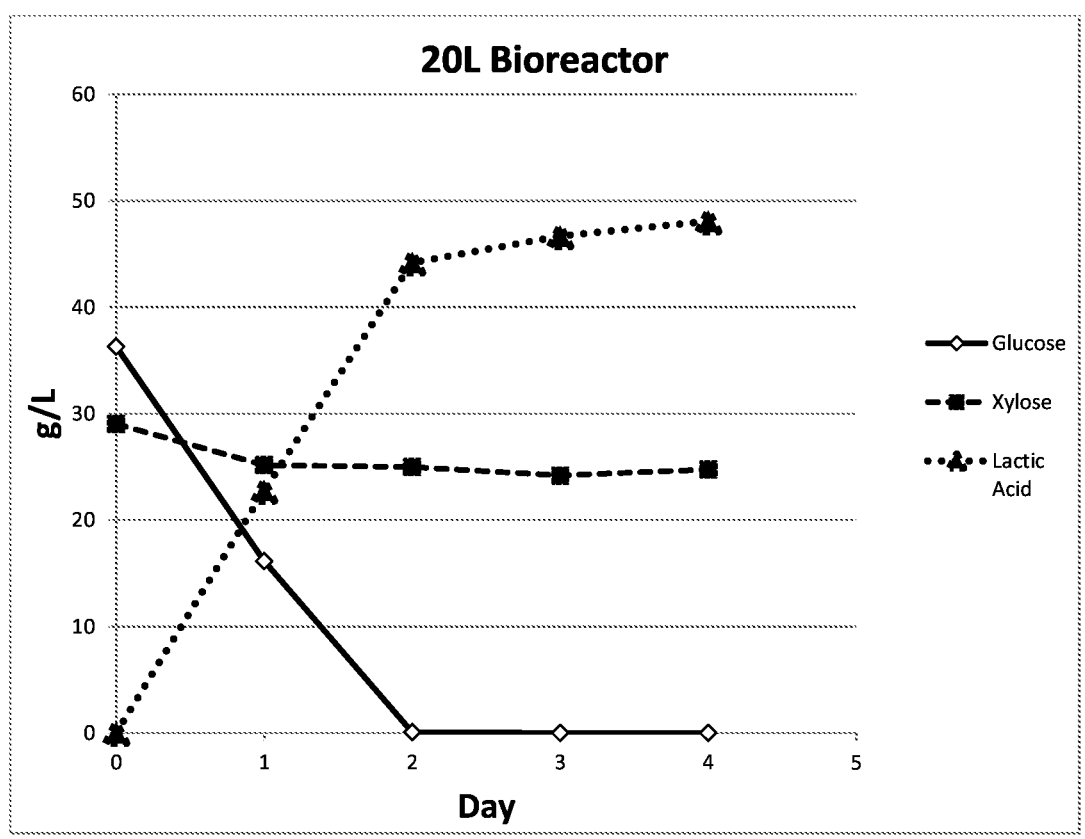
FIG. 8 is a plot of lactic acid production in a 20 L Bioreactor.

Similar data from results of the fermentation using the NRRL B-441 strain in the 20 L bioreactor are shown in FIG. 8. Glucose was completely consumed while xylose was not significantly consumed. Lactic acid was produced at a final concentration of about 47-48 g/L.

Enantiomer analysis is summarized for all strains tested in Table 4. *Lactobacillus casei* (NRRL-B-441) and *L. rhamnosus* (B-445) produced more than 96% L-lactic acid. *L. delbrueckii* sub. *Delbrueckii* (B-763) showed over 99% of the D-Lactic acid. The *L. plantarum* (ATCC 8014) showed an approximate equal mixture of each enantiomer.

TABLE 4

Ratio of L and D-Lactic Acid for Various Fermenting Organisms

| Strain | L-Lactic Acid | D-Lactic Acid |
|---|---|---|
| *L. casei* (B-441) | 96.1 | 3.9 |
| *L. rhamnosus* (B-445) | 98.3 | 1.7 |
| *L. delbrueckii* sub. *Delbrueckii* (B-763) | 0.6 | 99.4 |
| *L. plantarum* (ATCC 8014) | 52.8 | 47.2 |

Polymerization of Lactic Acid

A 250 ml three-necked flask was equipped with a mechanical stirrer and a condenser that was connected with a vacuum system through a cold trap. 100 grams of 90 wt. % aqueous L-lactic acid was dehydrated at 150° C., first at atmospheric pressure for 2 hours, then at a reduced pressure of 90 mmHg for 2 hours, and finally under a pressure of 20 mmHg for another 4 hours. A clear viscous liquid of oligo(L-lactic acid) was formed quantitatively.

400 mg (0.4 wt. %) of both tin(II) chloride dihydrate and para-toluene sulfonic acid was acid was added to the mixture and further heated to 180° C. for 5 hours at 8 mmHg With the reaction proceeding, the system became more viscous gradually. The reaction mixture was cooled down and then further heated at 150° C. in a vacuum oven another 19 hours.

Figure 9:
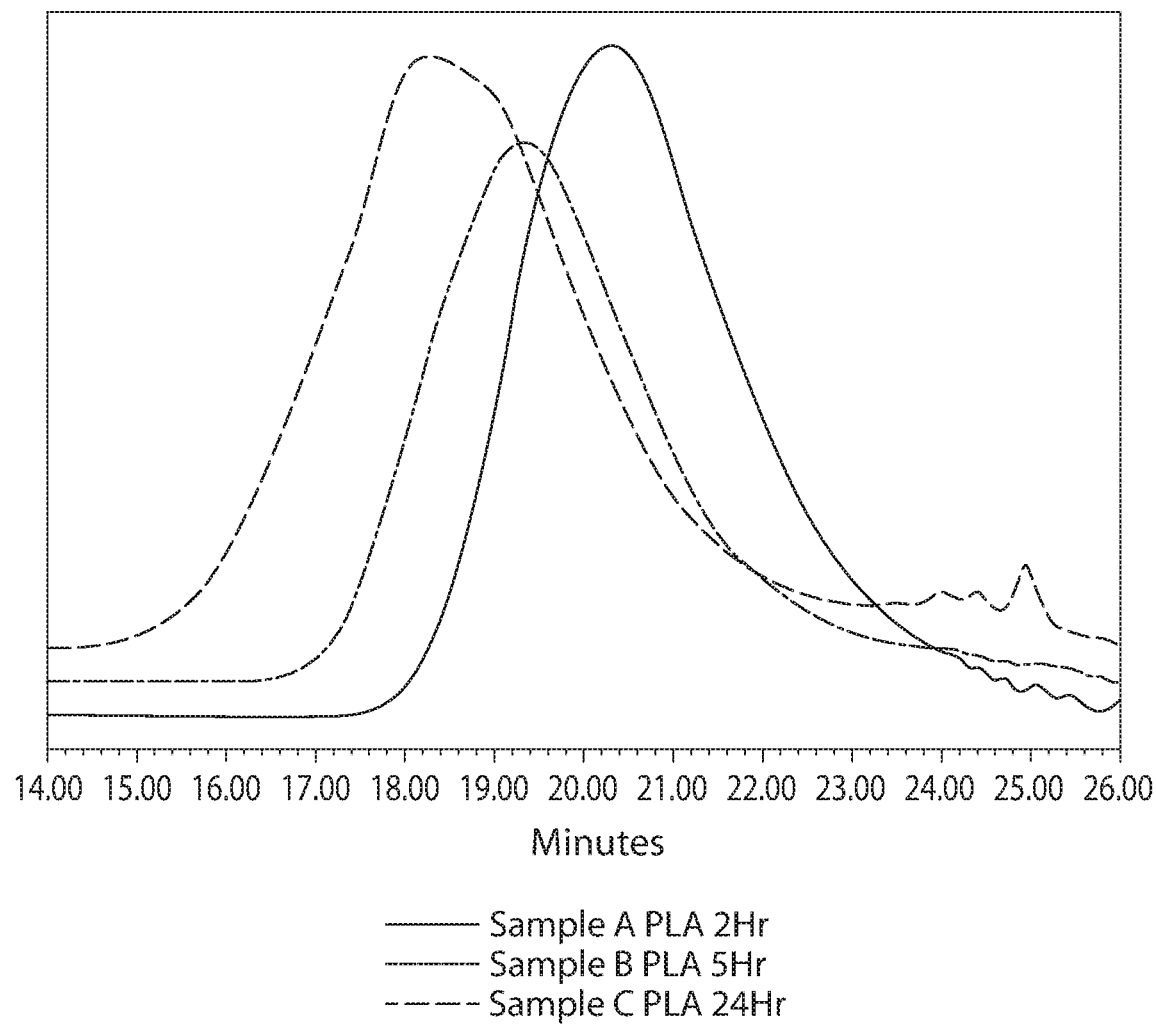
FIG. 9 is a plot of GPC data for poly lactic acid.

Samples were taken from the reaction mixture after 2 hours (A), 5 hours (B) and 24 hours (C) and the molecular weight was calculated using GPC using polystyrene standards in THF. FIG. 9 is a plot of GPC data for samples A, B and C.

| Sample | Reaction time (hours) | Molecular Weight | Retention Time |
|---|---|---|---|
| A | 2 | 8000 | 18.3 |
| B | 5 | 12000 | 19.3 |
| C | 24 | 35000 | 20.3 |

Other than in the examples herein, or unless otherwise expressly specified, all of the numerical ranges, amounts, values and percentages, such as those for amounts of materials, elemental contents, times and temperatures of reaction, ratios of amounts, and others, in the following portion of the specification and attached claims may be read as if prefaced by the word "about" even though the term "about" may not expressly appear with the value, amount, or range. Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains error necessarily resulting from the standard deviation found in its underlying respective testing measurements. Furthermore, when numerical ranges are set forth herein, these ranges are inclusive of the recited range end points (i.e., end points may be used). When percentages by weight are used herein, the numerical values reported are relative to the total weight.

Also, it should be understood that any numerical range recited herein is intended to include all sub-ranges subsumed therein. For example, a range of "1 to 10" is intended to include all sub-ranges between (and including) the recited minimum value of 1 and the recited maximum value of 10, that is, having a minimum value equal to or greater than 1 and a maximum value of equal to or less than 10. The terms "one," "a," or "an" as used herein are intended to include "at least one" or "one or more," unless otherwise indicated.

Any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

While this invention has been particularly shown and described with references to most preferred embodiments thereof, it will be understood by those skilled in the art that various changes in form and details may be made therein without departing from the scope of the invention encompassed by the appended claims.

The invention claimed is:
1. A method for processing biomass comprising:
   treating cellulosic or lignocellulosic material with an electron beam to provide a reduced recalcitrance lignocellulosic or cellulosic material;
   treating the reduced recalcitrance lignocellulosic or cellulosic material with one or more enzymes to obtain a sugar solution comprising xylose and glucose;
   fermenting the sugar solution with a thermophilic organism that selectively ferments glucose to lactic acid, while xylose is not significantly consumed, and
   converting the lactic acid to a product, wherein the product is an ester or polymer.

2. The method of claim 1, wherein converting comprises converting lactic acid to esters.

3. The method of claim 1, further comprising purifying the one or more sugars utilizing a method selected from the group consisting of one or more of electrodialysis, distillation, centrifugation, filtration, and cation exchange chromatography.

4. The method of claim 1, wherein converting comprises polymerizing the lactic acid to a polymer.

5. The method of claim 4, wherein a polymerizing method is selected from the group consisting of direct condensation of the lactic acid, azeotropic dehydrative condensation of the lactic acid, and dimerizing the lactic acid to lactide followed by ring opening polymerization of the lactide.

6. The method of claim 5, wherein the polymerization method is direct condensation and includes utilizing coupling agents and/or chain extenders to increase the molecular weight of the polymer.

7. The method of claim 6, wherein the coupling agents and/or chain extenders are selected from the group consisting of triphosgene, carbonyl diimidazole, dicyclohexylcarbodiimide, diisocyanate, acid chlorides, acid anhydrides, epoxides, thiirane, oxazoline, orthoester, and mixtures thereof.

8. The method of claim 5 wherein the polymerization method is azeotropic condensation.

9. The method of claim 4, wherein catalysts and/or promoters are utilized which are selected from the group consisting of Lewis acids, Bronsted acids, $H_3PO_4$, $H_2SO_4$, methane sulfonic acid, p-toluene sulfonic acid, polymerically supported sulfonic acids, metals, Mg, Al, Ti, Zn, Sn, metal oxides, $TiO_2$, ZnO, $GeO_2$, $ZrO_2$, SnO, $SnO_2$, $Sb_2O_3$, metal halides, $ZnCl_2$, $SnCl_2$, $SnCl_4$, $Mn(AcO)_2$, $Fe_2(LA)_3$, $Co(AcO)_2$, $Ni(AcO)_2$, $Cu(OA)_2$, $Zn(LA)_2$, $Y(OA)_3$, $Al(i-PrO)_3$, $Ti(BuO)_4$, $TiO(acac)_2$, $(Bu)_2SnO$, $Sn(octoate)_2$, solvates of any of these, and mixtures thereof.

10. The method of claim 8, further comprising conducting at least a portion of the polymerization at a temperature between about 100° C. and about 200° C.

11. The method of claim 8, wherein at least a portion of the polymerization is performed under vacuum.

12. The method of claim 5, wherein the polymerization method includes dimerizing the lactic acid to lactide followed by ring opening polymerization of the lactide.

13. The method of claim 12, wherein the dimerization includes heating the lactic acid to between 100° C. and 200° C. under a vacuum of about 0.1 mmHg to about 100 mmHg.

14. The method of claim 12, wherein the dimerization includes a catalyst selected from the group consisting of Sn octoate, Li carbonate, Zn diacetate dehydrate, Ti tetraisopropoxide, potassium carbonate, tin powder, and mixtures thereof.

15. The method of claim 12, wherein a ring opening polymerization catalyst is utilized which is selected from the group of Bronsted acids, HBr, HCl, triflic acid, Lewis acids, $ZnCl_2$, $AlCl_3$, anions, potassium benzoate, potassium phenoxide, potassium t-butoxide, and zinc stearate, metals, Tin, zinc, aluminum, antimony, bismuth, lanthanide and other heavy metals, Tin (II) oxide and tin (II) octoate, tetraphenyl tin, tin (II) and (IV) halogenides, tin (II) acetylacetonoate, distannoxanes, $Al(OiPr)_3$, other functionalized aluminium alkoxides, ethyl zinc, lead (II) oxide, antimony octoate, bismuth octoate, rare earth catalysts, yttrium tris(methyllactate), yttrium tris(2-N-N-dimethylamino ethoxide), samarium tris(2-N-N-dimethylamino ethoxide), yttrium tris (trimethylsilylmethyl), lanthanum tris(2,2,6,6-tetramethylheptanedionate), lanthanum tris(acetylacetonate), yttrium octoate, yttrium tris(acetylacetonate), yttrium tris(2,2,6,6-tetramethylheptanedionate), and mixtures thereof.

16. The method of claim 4, wherein converting further includes blending the polymer with a second polymer.

17. The method of claim 16, wherein the second polymer is selected from the group consisting of polyglycols, polyvinyl acetate, polyolefins, styrenic resins, polyacetals, poly(meth)acrylates, polycarbonate, polybutylene succinate, elastomers, polyurethanes, natural rubber, polybutadiene, neoprene, silicone, and combinations thereof.

18. The method of claim 4, wherein a co-monomer is co-polymerized with the lactic acid.

19. The method of claim 18, wherein the co-monomer is selected from the group consisting of elastomeric units, lactones, glycolic acid, carbonates, morpholinediones, epoxides, 1,4-benzodioxepin-2,5-(3H)-dione glycosalicylide, 1,4-benzodioxepin-2,5-(3H, 3-methyl)-dione lactosalicylide, dibenzo-1,5 dioxacin-6-12-dione disalicylide, morpholine-2,5-dione, 1,4-dioxane-2,5-dione glycolide, oxepane-2-one ε-caprolactone, 1,3-dioxane-2-one trimethylene carbonate, 2,2-dimethyltrimethylene carbonate, 1,5-dioxepane-2-one, 1,4-dioxane-2-one p-dioxanone, gamma-butyrolactone, beta-butyrolactone, beta-methyl-delta-valerolactone, 1,4-dioxane-2,3-dione ethylene oxalate, 3-[benzyloxycarbonyl methyl]-1,4-dioxane-2,5-dione, ethylene oxide, propylene oxide, 5,5'(oxepane-2-one), 2,4,7,9-tetraoxa-spiro[5,5]undecane-3,8-dione, and spiro-bis-dimethylene carbonate, and mixtures thereof.

20. The method of claim 4, comprising combining the polymer with fillers.

21. The method of claim 20, wherein the filler is selected from the group consisting of silicates, layered silicates, polymer and organically modified layered silicate, synthetic mica, carbon, carbon fibers, glass fibers, boric acid, talc, montmorillonite, clay, starch, corn starch, wheat starch, cellulose fibers, paper, rayon, non-woven fibers, wood flours, whiskers of potassium titanate, whiskers of aluminum borate, 4,4'-thiodiphenol, glycerol, and mixtures thereof.

22. The method of claim 20, wherein combining further includes extrusion and/or compression molding.

23. The method of claim 4, further comprising branching or cross linking the polymer.

24. The method of claim 23, wherein a cross linking agent is utilized to cross link the polymer and the cross-linking agent is selected from the group consisting of 5,5'-bis (oxepane-2-one)(bis-8-caprolactone)), spiro-bis-dimethylene carbonate, peroxides, dicumyl peroxide, benzoyl peroxide, unsaturated alcohols, hydroxyethyl methacrylate, 2-butene-1,4-diol, unsaturated anhydrides, maleic anhydride, saturated epoxides, glycidyl methacrylate, and combinations thereof.

25. The method of claim 4, further comprising processing the polymer by a method selected from injection molding, blow molding and thermoforming.

26. The method of claim 4, further comprising combining the polymer with a dye or pigment.

27. The method of claim 4, wherein converting further includes blending the polymer with a plasticizer.

28. The method of claim 27, wherein the plasticizer is selected from the group consisting of triacetin, tributyl citrate, polyethylene glycol, acetic acid ester of a monoglycerides, and diethyl bishydroxymethyl malonate, and mixtures thereof.

29. The method of claim 4, further comprising grafting a molecule to the polymer.

30. The method of claim 29, wherein the molecule is a monomer or a polymer.

31. The method of claim 29, further including treating the polymer with a peroxide, heating above about 120° C., irradiation, or combinations thereof.

32. The method of claim 4, further comprising shaping, molding, carving, extruding and/or assembling the polymer into a product.

33. The method of claim 32, wherein the product is selected from the group consisting of personal care items, tissues, towels, diapers, green packaging, compostable pots, consumer electronics, laptop casings, mobile phone casings, appliances, food packaging, disposable packaging, food containers, drink bottles, garbage bags, waste compostable bags, mulch films, controlled release matrices, controlled release containers, containers for fertilizers, containers for pesticides, containers for herbicides, containers for nutrients, containers for pharmaceuticals, containers for flavoring agents, containers for foods, shopping bags, general purpose film, high heat film, heat seal layer, surface coating, disposable tableware, plates, cups, forks, knives, spoons, sporks, bowls, automotive parts, panels, fabrics, under hood covers, carpet fibers, clothing fibers, fibers for garments, fibers for sportswear, fibers for footwear, surgical sutures, implants, scaffolding and drug delivery systems.

34. The method of claim 1, where prior to treating the cellulosic or lignocellulosic material with the electron beam the biomass size is reduced by cutting, grinding, shearing, pulverizing, and/or chopping.

35. The method of claim 1, wherein after treating the cellulosic or lignocellulosic material with the electron beam, and before saccharification, the biomass is heat treated at a temperature of 95° C. to 160° C.

36. The method of claim 35, wherein the biomass is heat treated at a temperature of 100° C. to 150° C.

37. The method of claim 35, wherein the biomass is heat treated at a temperature of 110° C. to 140° C.

38. The method of claim 35, where the heat treated biomass step comprises an aqueous mixture with the biomass 10 to 90 wt. % of the entire mixture.

39. The method of claim 1 where converting comprises chemically converting.

40. The method of claim 39, wherein converting comprises converting lactic acid to esters by treating with an alcohol and an acid catalyst.

41. The method of claim 1, wherein the fermenting step occurs at a temperature of above 50° C.

42. The method of claim 1, further comprising isolating the lactic acid from the xylose.

* * * * *